US009574004B2

(12) United States Patent
Ardeleanu et al.

(10) Patent No.: US 9,574,004 B2
(45) Date of Patent: Feb. 21, 2017

(54) METHODS FOR TREATING OR PREVENTING ASTHMA BY ADMINISTERING AN IL-4R ANTAGONIST

(71) Applicants: SANOFI, Paris (FR); REGENERON PHARMACEUTICALS, INC., Tarrytown, NY (US)

(72) Inventors: Marius Ardeleanu, White Plains, NY (US); Namita A. Gandhi, New York, NY (US); Neil Graham, Croton-on-Hudson, NY (US); Stephanie C. Kirkesseli, Paris (FR); Sudeep Kundu, New York, NY (US); Ross E. Rocklin, Basking Ridge, NJ (US); Allen Radin, New York, NY (US); Steven P. Weinstein, Hartsdale, NY (US); Jennifer Davidson Hamilton, Hopewell Junction, NY (US); Jeffrey Ming, Bridgewater, NJ (US)

(73) Assignees: Sanofi Biotechnology, Paris (FR); Regeneron Pharmaceuticals, Inc., Tarrytown, NY (US)

( * ) Notice: Subject to any disclaimer, the term of this patent is extended or adjusted under 35 U.S.C. 154(b) by 124 days.

(21) Appl. No.: 13/971,334

(22) Filed: Aug. 20, 2013

(65) Prior Publication Data

US 2014/0056920 A1    Feb. 27, 2014

Related U.S. Application Data

(60) Provisional application No. 61/805,797, filed on Mar. 27, 2013, provisional application No. 61/783,796, filed on Mar. 14, 2013, provisional application No. 61/761,279, filed on Feb. 6, 2013, provisional application No. 61/758,097, filed on Jan. 29, 2013, provisional application No. 61/691,625, filed on Aug. 21, 2012.

(30) Foreign Application Priority Data

Jul. 16, 2013  (FR) .................................... 13 56994

(51) Int. Cl.

| | | |
|---|---|---|
| A61K 39/395 | (2006.01) | |
| A61K 39/00 | (2006.01) | |
| A61K 45/06 | (2006.01) | |
| C07K 16/24 | (2006.01) | |
| C07K 16/28 | (2006.01) | |
| C12Q 1/68 | (2006.01) | |

(52) U.S. Cl.
CPC ....... *C07K 16/2866* (2013.01); *A61K 39/3955* (2013.01); *A61K 39/39541* (2013.01); *A61K 45/06* (2013.01); *C07K 16/247* (2013.01); *C12Q 1/6883* (2013.01); *A61K 2039/505* (2013.01); *A61K 2039/54* (2013.01); *C07K 2317/21* (2013.01); *C12Q 2600/106* (2013.01); *C12Q 2600/158* (2013.01)

(58) Field of Classification Search
CPC ................ A61K 39/3955; A61K 45/06; A61K 39/39541; A61K 2039/505; A61K 2039/54; C07K 16/2866; C07K 16/247; C07K 2317/21
See application file for complete search history.

(56) References Cited

U.S. PATENT DOCUMENTS

| | | | |
|---|---|---|---|
| 7,605,237 | B2 | 9/1993 | Gustafson et al. |
| 5,599,905 | A | 2/1997 | Mosley et al. |
| 5,714,146 | A | 2/1998 | Lewis et al. |
| 5,717,072 | A | 2/1998 | Mosley et al. |
| 5,856,296 | A | 1/1999 | Mosley et al. |
| 5,985,280 | A | 11/1999 | Ritter et al. |
| 6,156,877 | A | 12/2000 | Ritter et al. |
| 6,391,581 | B1 | 5/2002 | Mosley et al. |
| 6,716,587 | B2 | 4/2004 | Mosley et al. |
| 7,186,809 | B2 | 3/2007 | Pluenneke et al. |
| 7,317,090 | B2 | 1/2008 | Mosley et al. |
| 7,794,717 | B2 | 9/2010 | Stevens et al. |
| 8,075,887 | B2 | 12/2011 | Martin et al. |
| 8,092,802 | B2 | 1/2012 | Stevens et al. |
| 8,337,839 | B2 | 12/2012 | Rawlings et al. |
| 8,338,135 | B2 | 12/2012 | Stevens et al. |
| 2003/0124121 | A1 | 7/2003 | Pluenneke |
| 2005/0118176 | A1 | 6/2005 | Mosley et al. |

(Continued)

FOREIGN PATENT DOCUMENTS

| | | |
|---|---|---|
| EP | 0 604 693 | 7/1994 |
| EP | 0 367 566 A1 | 5/1997 |

(Continued)

OTHER PUBLICATIONS

Virchow, J-C., et al. Cellular and immunological markers of allergic and intrinsic bronchial asthma. Lung, 1994, vol. 172, p. 313-334.*
Bateman, E.D., et al. Can guideline-defined asthma control be achieved? Am. J. Respir. Crit. Care Med., 2004, vol. 170, p. 836-844.*
Sekiya, T., et al. Increased levels of a TH2-type CC chemokine thymus and activation-regulated chemokine (TARC) in serum and induced sputumm of asthmatics. Allergy, 2002, vol. 57, p. 173-177.*
Niranjan, R. et al. Pathogenesis of allergen-induced eosinophilic esophagitis is independent of interleukin (IL)-13. Immunology and Cell Biology, 2013, vol. 91, p. 408-415.*
Borish, L.C. et al, Efficacy of soluble IL-4 receptor for the treatment of adults with asthma. J. Clin. Allergy Clin. Immunol., 2001, vol. 107, p. 963-970).*
Wenzel, S., et al. Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial. Lancet, 2016, vol. 388, p. 31-44.*

(Continued)

*Primary Examiner* — Robert Landsman
*Assistant Examiner* — Bruce D Hissong
(74) *Attorney, Agent, or Firm* — Lathrop & Gage LLP; James H. Velema, Esq.

(57) ABSTRACT

The present invention provides methods for treating or preventing asthma and associated conditions in a patient. The methods of the present invention comprise administering to a subject in need thereof a therapeutic composition comprising an interleukin-4 receptor (IL-4R) antagonist, such as an anti-IL-4R antibody.

19 Claims, 31 Drawing Sheets

(56) References Cited

U.S. PATENT DOCUMENTS

| | | |
|---|---|---|
| 2005/0255532 A1 | 11/2005 | Ruben et al. |
| 2005/0282181 A1 | 12/2005 | Yan et al. |
| 2007/0041976 A1 | 2/2007 | Pluenneke et al. |
| 2007/0274996 A1 | 11/2007 | Carter et al. |
| 2009/0074793 A1 | 3/2009 | Martin et al. |
| 2009/0098142 A1 | 4/2009 | Kassalan et al. |
| 2010/0047254 A1* | 2/2010 | Martin et al. ............. 424/158.1 |
| 2012/0004205 A1 | 1/2012 | Rothenberg |
| 2012/0052072 A1 | 3/2012 | Martin et al. |
| 2013/0078675 A1 | 3/2013 | Martin et al. |

FOREIGN PATENT DOCUMENTS

| | | |
|---|---|---|
| EP | 2022507 A1 | 2/2009 |
| WO | WO 01/92340 | 12/2001 |
| WO | WO 2005/047331 | 5/2005 |
| WO | WO 2005/085284 | 9/2005 |
| WO | WO 2006/072564 | 7/2006 |
| WO | 2008054606 A2 | 5/2008 |
| WO | 2010053751 A1 | 5/2010 |
| WO | 2014039461 A1 | 3/2014 |

OTHER PUBLICATIONS

Burmeister-Getz et al: Human Pharmacokinetics/Pharmacodynamics of an Interleukin-4 and Interleukin-13 Dual Antagonist in Asthma; J Clin Pharmacol; 2009; vol. 49, pp. 1025-1036.

Corren et al: A Randomized, controlled, Phase 2 Study of AMG 317, an IL-4R-alpha antagonist, in Patients with Asthma; AJRCCM Articles in Press; Jan. 7, 2010; doi:10.1164/rccm.200909-1448OC; 34 pages.

Davies et al: Affinity improvement of single antibody VH domains: residues in all three hypervariable regions affect antigen binding; Immunotechnol. 1996, vol. 2, pp. 169-179.

Gavett et al: Interleukin-4 receptor blockade prevents airway responses induced by antigen challenge in mice; Am J Physiol; 1997, vol. 272, pp. L253-L261.

Holt et al: Domain antibodies: Proteins for Therapy; Trends Biotechnol; 2003, vol. 21, pp. 484-490.

Maliszewski et al: In Vivo Biological Effects of Recombinant Soluble Interleukin-4 Receptor; Proc Soc Exp Biol Med; 1994, vol. 206, pp. 233-237.

Oh et al: Investigational therapeutics targeting the IL-4/IL-13/STAT-6 pathway for the treatment of asthma; Eur Respir Rev; 2010; vol. 19, pp. 46-54.

Sato et al: Recombinant Soluble Murine IL-4 Receptor Can Inhibit or Enhance IgE Responses in Vivo; J Immunol; 1993, vol. 150, pp. 2717-2723.

Tomkinson et al: A Murine IL-4 Receptor Antagonist That Inhibits IL-4- and IL-13-Induced Responses Prevents Antigen-Induced Airway Eosinophilia and Airway Hyperresponsiveness; J Immunol 2001, vol. 166, pp. 5792-5800.

Wenzel et al: Effect of an interleukin-4 variant on late phase asthmatic response to allergen challenge in asthmatic patients: results of two phase 2a studies; Lancet; 2007, vol. 370, pp. 1422-1431.

Arron et al: Peripheral Biomarkers of an IL-13 Induced Bronchial Epithelial Gene Signature in Asthma; Am J Respir Crit Care Med; Online Abstracts Issue; 2009, B21 Airway Inflammation: New Information About Mediators and Biomarkers / Poster Discussion / Monday, May 18, 2009; 1 page.

Woodruff et al: T-helper Type 2-driven Inflammation Defines Major Subphenotypes of Asthma; Am J Respir Crit Care Med; 2009, vol. 180, pp. 388-395.

Zurawski et al: The primary binding subunit of the human interleukin-4 receptor is also a component of the Interleukin-13 Receptor; J. Biol. Chem.; 1995, vol. 270, pp. 13869-13878.

International Search Report, PCT/US2013/055747, Dated Feb. 13, 2014. 8 pages.

Corren et al. 'A Randomized, Controlled, Phase 2 Study of AMG 317, an IL-4R Antagonist, in Patients with Asthma'. American Journal of Respiratory and Critical Care Medicine. 2010, vol. 181, No. 8, pp. 788-796.

Wenzel et al. 'ERS—Programme'. European Respiratory Society, Annual Congress 2010, pp. 3980.

Otulana et al. 'A Phase 2b Study of Inhaled Pitrakinra, An IL-4R/IL-13 Antagonist, Successfully Identified Responder Subpopulations of Patients with Uncontrolled Asthma'. American Journal of Respiratory and Critical Care Medicine. 2011, vol. 183, pp. A6179.

Slager et al. 'IL-4 Receptor Polymorphisms Predict Reduction in Asthma Exacerbations During Response to an AntiIL-4Receptor Antagonist'. Journal of Allergy, Asthma and Immunology. 2012, vol. 130, No. 2, pp. 516-522.

International Preliminary Report on Patentability corresponding to International Patent Application No. PCT/US2013/055747, issued Feb. 24, 2015.

Groves et al., "Inhibition of IL-4 and IL-13 with an IL-4 mutein (Aeroderm) protects against flares in atopic eczema." Aeroderm in AD Poster at St. John's Institute of Dermatology. 2007.

Grunewald, et al., "An antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo." The Hournal of Immunology. 1998, 160(8):4004-4009.

Junitlla et al., "Tuning sensitivity to IL-4 and IL-13: differential expression of IL-4Ra, IL-13Ra1, and Yc regulates relative cytokine sensitivity." J. Exp. Med. 2008, 205(11):2595-2608.

Kakkar et al., "Population PK and IgE Pharmacodynamic Analysis of a Fully Human Monoclonal Antibody Against IL4 Receptor." Pharmaceutical Research, Kluwer Academic Publishers-Plenum Publishers. 2011, 28(10):2530-2542.

Kopf et al., "Disruption of the murine IL-4 gene blocks Th2 cytokine responses." Letters to Nature. 1993, 362:245-248.

Kostic et al., "A Fully Human IL4Ra Antibody for Inhibition of IL-4/IL-13-driven TH2 Responses in Allergic Disease." Clinical Immunology. 2010, 135:S105-S106.

Ludmila et al., "Poster 1013: IL-4R alpha antibody inhibits IgE production and airway remodeling in the mouse model of house dust mite-induced eosinophilic asthma." World Allergy Organization Journal. 2014, 7(1):P8.

Morioka et al., "IL-4/IL-13 antagonist DNA vaccination successfully suppresses Th2 type chronic dermatitis." British Journal of Dermatology. 2009, 160(6):1172-1179.

"Sanofi and Regeneron Report Positive Proof-of-Concept Data for Dupilumab, and IL-4R alpha Antibody, in Atopic Dermatitis." 71st Annual Meeting of the American Academy of Dermatology, 2013 http://files.shareholder.com/downloads/REGN/2689212012x0x640531/794a7e54-6904-416b-ba38-a4ccc1726852/REGN_News_2013_3_2_General_Releases.pdf>.

Schmidt-Weber, "Anti-IL-4 as a New Strategy in Allergy." Chem Immunol Allergy. 2012, 96:120-125.

Tazawa et al., "Relative importance of IL-4 and IL-13 in lesional skin of atopic dermatitis." Arch Dermatol Res. 2004, 295:459-464.

Walker et al., "Atopic dermatitis: correlation of peripheral blood T cell activation, eosinophilia and serum factors with clinical severity." Clinical and Experimental Allergy. 1993, 23:145-153.

Wils-Karp et al., "Untangling the Complex Web of IL-4 and IL-13 Mediated Signaling Pathways." Science Signaling. 2008, 1(51):1-5.

Wenzel et al., "Dupilumab in Persistent Asthma with Elevated Eosiniphil Levels." New England Journal of Medicine. 2013, 368(26):2455-2466.

Yamanaka et al., "The Role of Cytokines/Chemokines in the Pathogenesis of Atopic Dermatitis." Curr. Probl. Dermatol. 2011, 41:80-92.

Zuo et al., "IL-13 Induced Esophageal Remodeling and Gene Expression by an Eosinophil-Independent, IL-13R {alpha}2-Inhibited Pathway." Journal of Immunology. 2010, 185:660-669.

Newton et al., 'A Review of Nasal Polyposis'. Therapeutic and Clinical Risk Management, 2008, vol. 4 (2): 507-512.

Walker et al., 'Use of Biologics as Immunotherapy in Asthma and Related Diseases'. Expert Review of Clinical Immunology, 2008, vol. 4(6): 743-756.

\* cited by examiner

FEV1 vs. Blood Eosinophils

ACQ vs. YKL-40

IL-4$^{Hu/Hu}$ IL-4Ra$^{Hu/Hu}$ mice

METHODS FOR TREATING OR PREVENTING ASTHMA BY ADMINISTERING AN IL-4R ANTAGONIST

RELATED APPLICATIONS

This application claims the benefit of priority of U.S. Provisional Application No. 61/691,625, filed Aug. 21, 2012; U.S. Provisional Application No. 61/758,097 filed Jan. 29, 2013; U.S. Provisional Application No. 61/761,279, filed Feb. 6, 2013; U.S. Provisional Application No. 61/783,796, filed Mar. 14, 2013; U.S. Provisional Application No. 61/805,797, filed Mar. 27, 2013; and French Application No. 1356994, filed 16 Jul. 2013. The contents of each of the aforementioned applications are hereby incorporated by reference herein in their entireties.

FIELD OF THE INVENTION

The present invention relates to the treatment and/or prevention of asthma and related conditions. More specifically, the invention relates to the administration of an interleukin-4 receptor (IL-4R) antagonist to treat or prevent asthma in a patient in need thereof.

BACKGROUND

Asthma is a chronic inflammatory disease of the airways characterized by airway hyper responsiveness, acute and chronic bronchoconstriction, airway edema, and mucus plugging. The inflammation component of asthma is thought to involve many cell types, including mast cells, eosinophils, T lymphocytes, neutrophils, and epithelial cells, and their biological products. Patients with asthma most often present with symptoms of wheezing, shortness of breath, cough, and chest tightness. For most asthma patients, a regimen of controller therapy and bronchodilator therapy provides adequate long-term control. Inhaled corticosteroids (ICS) are considered the "gold standard" in controlling asthma symptoms, and inhaled beta2-agonists are the most effective bronchodilators currently available. Studies have shown that combination therapy of an ICS with an inhaled long-acting beta2-agonist (LABA) provides better asthma control than high doses of ICS alone. Consequently, combination therapy has been the recommended treatment for subjects who are not controlled on low doses of ICS alone.

Nonetheless, it is estimated that 5% to 10% of the population with asthma has symptomatic disease despite maximum recommended treatment with combinations of anti-inflammatory and bronchodilator drugs. Furthermore, this severe asthma population accounts for up to 50% of the total health cost through hospital admissions, use of emergency services, and unscheduled physician visits. There is an unmet need for a new therapy in this severe asthma population as many of these patients are poorly responsive to ICS due to a number of cellular and molecular mechanisms. In addition, the long term adverse effects of systemic and inhaled corticosteroids on bone metabolism, adrenal function, and growth in children lead to attempts to minimize the amount of corticosteroid usage. Although a large portion of asthma patients are managed reasonably well with current treatments, patients with severe corticosteroid-refractory asthma have few therapeutic treatment options that can adequately control the disease. The consequence of unresponsiveness to therapy or lack of compliance with therapy is loss of asthma control and ultimately asthma exacerbation.

One of the reasons for the poor response to medication in some patients with severe asthma may be the heterogeneity of the disease. Interest is increasing in understanding these distinct phenotypes because targeted therapy is more likely to be successful in patients with similar underlying pathobiological features. Recent therapeutic approaches in asthma have focused on trying to control the T helper cell-2 response. Up-regulation of interleukin-4 (IL-4) and interleukin-13 (IL-13) has been implicated as an important inflammatory component of asthma disease progression.

Accordingly, a need exists in the art for novel targeted therapies for the treatment and/or prevention of asthma.

BRIEF SUMMARY OF THE INVENTION

According to one aspect of the present invention, methods are provided for reducing the incidence of asthma exacerbations in a subject in need thereof. In a related aspect, methods are provided for improving one or more asthma-associated parameter(s) in a subject in need thereof. In yet another aspect of the present invention, methods are provided for treating asthma, e.g., moderate-to-severe eosinophilic asthma, in a subject in need thereof.

The methods featured in the invention comprise administering to a subject a therapeutically effective amount of a pharmaceutical composition comprising an interleukin-4 receptor (IL-4R) antagonist. According to certain embodiments, the IL-4R antagonist is an antibody or antigen-binding fragment thereof that specifically binds IL-4R. Exemplary anti-IL-4R antibodies that can be used in the context of the methods of the present invention are described elsewhere herein, including working Example 1. For example, in one embodiment, the IL-4R antagonist is an antibody or antigen-binding fragment thereof that specifically binds to an IL-4R, and comprises the heavy chain and light chain (complementarity determining region) CDR sequences from the heavy chain variable region (HCVR) and light chain variable region (LCVR) of SEQ ID NOs:162 and 164, respectively.

In one embodiment, a method for reducing the incidence of one or more asthma exacerbations in a subject in need thereof is provided by administering an antibody or antigen binding fragment thereof that specifically binds IL-4R. The asthma exacerbation can be one or more of the following: (a) a 30% or greater reduction from baseline in morning peak expiratory flow (PEF) on two consecutive days; (b) six or more additional reliever puffs of albuterol or levalbuterol in a 24 hour period (compared to baseline) on two consecutive days; and (c) a deterioration of asthma requiring: (i) systemic (oral and/or parenteral) steroid treatment, or (ii) an increase in inhaled corticosteroids to at least 4 times the last dose received prior to discontinuation, or hospitalization.

In various embodiments, methods for improving one or more asthma-associated parameters comprise administering to a subject in need thereof, a therapeutically effective amount of an IL-4R antagonist, wherein the improvement in an asthma-associated parameter is defined as one of the following: an increase from baseline of FEV1; an increase from baseline of AM PEF; an increase from baseline of PM PEF; a decrease from baseline of albuterol/levalbuterol use; a decrease from baseline of nighttime awakenings; and/or a decrease from baseline of SNOT-22 score. Examples of asthma-associated parameters include: (a) forced expiratory volume in 1 second (FEV1); (b) peak expiratory flow rate (PEF), including morning PEF (AM PEF) and evening PEF (PM PEF); (c) use of an inhaled bronchodilator, such as albuterol or levalbuterol; (d) five-item Asthma Control Questionnaire (ACQ5) score; (d) nighttime awakenings; and (e) 22-item Sino-Nasal Outcome Test (SNOT-22) score. In one embodiment, the improvement in an asthma-associated parameter is an increase of at least 0.10 L from baseline of FEV1. In one embodiment, the improvement in an asthma-associated parameter is an increase of at least 10.0 L/min from baseline of AM PEF. In one embodiment, the improvement in an asthma-associated parameter is an increase of at least 1.0 L/min from baseline of PM PEF. In one embodiment, the improvement in an asthma-associated parameter is a decrease in albuterol/levalbuterol use of at least 1 puff(s) per day from baseline. In one embodiment, the improvement in an asthma-associated parameter is a decrease of at least 0.5 points from baseline in ACQ5 score. In one embodiment, the improvement in an asthma-associated parameter is a decrease of at least 0.2 times per night from baseline of nighttime awakenings. In one embodiment, the improvement in an asthma-associated parameter is a decrease of at least 5 points from baseline in SNOT-22 score.

The invention also provides methods for reducing the incidence of asthma exacerbations, or improving one or more asthma-associated parameter(s) in a subject in need thereof, wherein the methods comprise sequentially administering to a subject in need thereof a single initial dose of a pharmaceutical composition comprising an IL-4R antagonist (e.g., an anti-IL-4R antibody or antigen-binding fragment thereof), followed by one or more secondary doses of the pharmaceutical composition comprising the IL-4R antagonist. The pharmaceutical composition comprising the IL-4R antagonist may be administered subcutaneously, intranasally or intravenously to the subject in need thereof.

According to certain embodiments, the invention provides methods for reducing the incidence of asthma exacerbations, or improving one or more asthma-associated parameter(s) in a subject in need thereof, wherein the methods comprise administering to the subject about 75 to about 300 mg of a pharmaceutical composition comprising an antibody or antigen-binding fragment thereof that specifically binds IL-4R. According to this aspect, the pharmaceutical composition may be administered to the subject at a dosing frequency of, e.g., once a week.

The invention further includes methods for treating asthma (e.g., eosinophilic asthma, moderate to severe eosinophilic asthma, etc.) by selecting a subject who exhibits one or more symptoms or indicia of asthma, and administering to the patient a pharmaceutical composition comprising an IL-4R antagonist (e.g., an anti-IL-4R antibody or antigen-binding fragment thereof), wherein the subject exhibits one or more of the following symptoms or indicia of asthma: (1) the subject has been treated with a stable dose of either fluticasone/salmeterol combination therapy (250/50 µg BID or 500/50 µg BID) or budesonide/formoterol combination therapy (160/9 µg BID or 320/9 µg BID) for at least 3 months prior to screening; (2) the subject has blood eosinophils greater than or equal to 300 cell/µL; (3) the subject has sputum eosinophils greater than or equal to 3%; (4) the subject has elevated levels of IgE, thymus and activation regulation chemokine (TARC), eotaxin-3, carcinoembryonic antigen (CEA), YKL-40, or periostin; (5) the subject has an elevated level of fractional exhaled nitric oxide (FeNO); and/or (6) the subject has an Asthma Control Questionnaire (ACQ5) score greater than or equal to 1.0.

Embodiments featured in the invention are directed to methods of treatment, as described above, further comprising administration of a second therapeutic agent in combination with the IL-4R antagonist. The second therapeutic agent may be administered to a subject in need thereof before, after or concurrent with IL-4R antagonist. Exemplary second therapeutic agents include, but are not limited to, one or more of the following in combination: IL-1 inhibitors, IL-5 inhibitors, IL-8 inhibitors, IgE inhibitors, tumor necrosis factor (TNF) inhibitors, corticosteroids, long acting beta2-agonists, and leukotriene inhibitors.

In another aspect, the invention provides methods to reduce or eliminate an asthma patient's dependence on background asthma therapy comprising selecting a patient who has moderate-to-severe asthma that is uncontrolled or partially controlled with background asthma therapy; administering to the patient a defined dose of an IL-4R antagonist while maintaining the patient's background therapy; and gradually reducing the dosage of one or more components of the background therapy over a subsequent treatment period while continuing to administer the IL-4R antagonist. In certain embodiments, the background therapy comprises an inhaled corticosteroid (ICS), a long-acting beta-agonist (LABA), or a combination of an ICS and a LABA. In some embodiments, the background therapy is gradually reduced or withdrawn over a period of 2-8 weeks. In some embodiments, one component of the background therapy is eliminated after an initial treatment period. In one embodiment, the background therapy is gradually reduced over a subsequent treatment period.

In yet another aspect, the invention provides a method for identifying a patient and treating moderate-to-severe asthma by selecting a patient with an elevated level of a biomarker, such as thymus and activation-regulated chemokine (TARC), IgE, eotaxin-3, periostin, carcinoembryonic antigen (CEA), or YKL-40, or having an increased level of fractional exhaled nitric oxide (FeNO); and administering to the patient a therapeutically effective amount of an IL-4R antagonist.

In another aspect, the invention features a method for monitoring effectiveness of treatment of moderate-to-severe asthma in a subject, such as by (a) determining the expression level of a biomarker, such as one or both of TARC or eotaxin-3, or the total serum level of IgE in a biological sample acquired from the subject before treatment with an IL-4R antagonist; (b) determining the expression level of the biomarker in a biological sample acquired from the subject after treatment with the IL-4R antagonist; (c) comparing the expression level determined in step (a) with the level in step (b), and (d) concluding that the treatment is effective when the level determined in step (b) is lower than the level determined in step (a), or concluding that the treatment is not effective when the level determined in step (b) is the same as or higher than the level determined in step (a).

In one embodiment, the biomarker is FeNO, and if FeNO levels decrease following administration of the antagonist, then treatment with the IL-4R antagonist is determined to be effective.

The expression level of the biomarker can be determined, for example, 1 week, 2 weeks, 3 weeks, 4 weeks, 5 weeks, or longer after administration of the IL-4R antagonist, and compared to the expression level prior to administration of the antagonist. The dose or the dosing regimen of the IL-4R antagonist (e.g., an anti-IL4R antibody) can be adjusted following the determination. For example, if the expression of the biomarker fails to decrease within 1 week, 2 weeks, 3 weeks, 4 weeks, 5 weeks, or longer following administration of the antagonist, then treatment with the antagonist can be stopped, or the dose of the antagonist can be increased. If expression of the biomarker decreases following administration of the antagonist, the dosage of the antagonist can be maintained or decreased, such as to identify a minimal effective dose. In some embodiments, treatment is maintained at the minimal effective dose.

In another aspect, the invention features a method for monitoring a subject's response to treatment with an IL-4R antagonist, wherein the subject has moderate-to-severe asthma, such as by acquiring information regarding expression level of a biomarker, such as one or both of TARC or eotaxin-3, or total serum level of IgE in a biological sample from the subject following administration of the IL-4R antagonist to the subject, and providing an indication that treatment should be continued if the expression level of the biomarker has decreased as compared to the level before treatment with the IL-4R antagonist. In one embodiment the biomarker is FeNO, and if FeNO levels are determined to decrease following administration of the antibody, then an indication is provided to continue treatment with the IL-4R antagonist.

The invention also includes an IL-4R antagonist as disclosed herein for use in the manufacture of a medicament for the treatment and/or prevention of asthma (e.g., eosinophilic asthma, moderate to severe eosinophilic asthma, etc.) or for treating any of the other indications or conditions disclosed herein.

The invention also includes an IL-4R antagonist as disclosed herein for use in the treatment and/or prevention of asthma (e.g., eosinophilic asthma, moderate to severe eosinophilic asthma, etc.) or for treating and/or prevention of any of the other indications or conditions disclosed herein.

The invention includes a pharmaceutical composition comprising an anti-IL4R antibody antagonist or an antigen binding fragment thereof for use in the treatment and/or prevention of asthma and related conditions.

The invention also includes a pharmaceutical composition comprising an anti-IL4R antibody antagonist or an antigen binding fragment thereof for use in reducing the incidence of one or more asthma exacerbations in a subject in need thereof.

In addition, the invention includes a pharmaceutical composition comprising an anti-IL4R antibody antagonist or an antigen binding fragment thereof for use in improving one or more asthma-associated parameter(s) in a subject in need thereof.

The invention includes a pharmaceutical composition comprising an anti-IL4R antibody antagonist or an antigen binding fragment thereof for use in the treatment of asthma and related conditions in a patient having an elevated level of a biomarker selected from the group consisting of thymus and activation-regulated chemokine (TARC), IgE, eotaxin-3, periostin, carcinoembryonic antigen (CEA), YKL-40, and fractional exhaled nitric oxide (FeNO).

The invention further includes a pharmaceutical composition comprising an anti-IL4R antibody antagonist or an antigen binding fragment thereof for use in the treatment of asthma or moderate to severe eosinophilic asthma in a subject in need thereof wherein the treatment comprises testing the patient for the presence of a blood eosinophil level of at least 300 cells per microliter and/or a sputum eosinophil level of at least 3% and beginning/continuing administration of the pharmaceutical composition if such blood eosinophil level and/or sputum eosinophil level is found.

Other embodiments of the invention will become apparent from a review of the ensuing detailed description.

DETAILED DESCRIPTION

Figure 1:
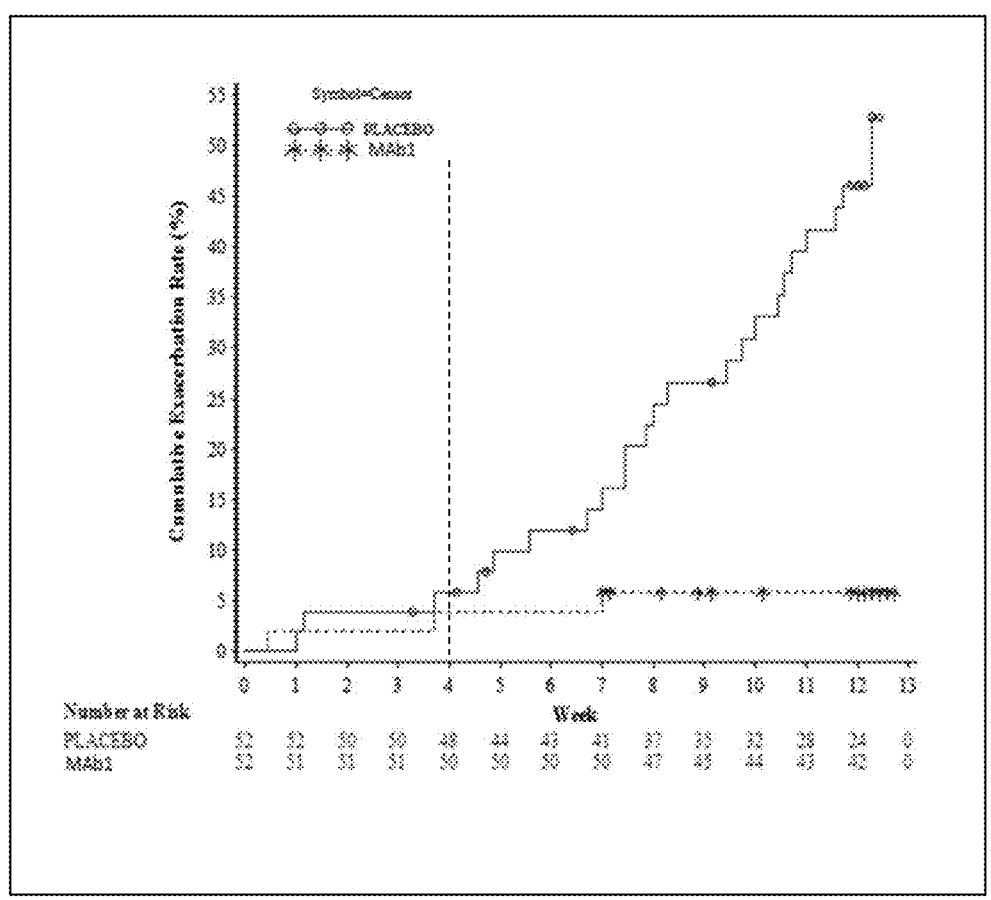
FIG. 1 is a graph that shows a Kaplan-Meier plot of time to asthma exacerbation in patients treated with placebo (open circles) as compared to patients treated with anti-IL-4R antibody mAb1 (asterisks). The effect of the treatment with an anti-IL-4R antibody mAb1 is sustained over time, including after 8 weeks, when patients are at higher risk of developing exacerbations due to steroid withdrawal. Broken vertical lines indicate withdrawal of LABA.
Figure 2:
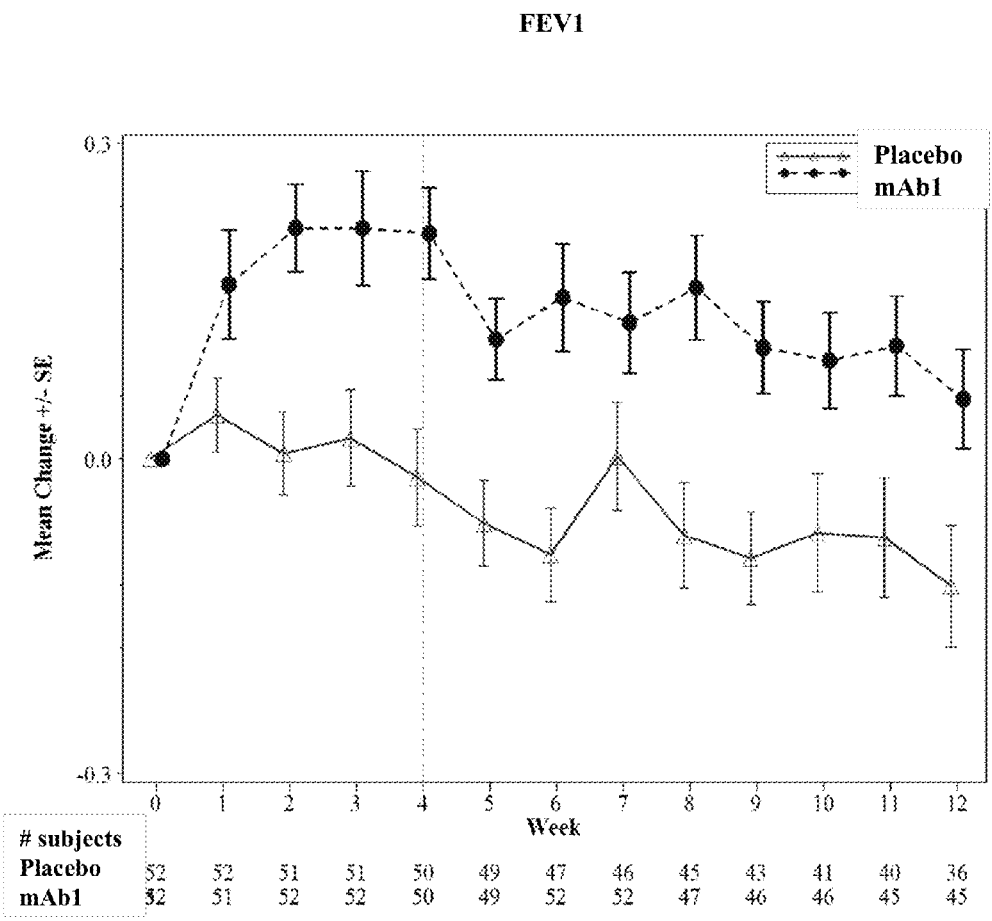
FIG. 2 is a graph that shows the mean change from baseline in forced expiratory volume in 1 second (FEV1) in liters in patients treated with placebo (open triangles) as compared to patients treated with anti-IL-4R antibody mAb1 (closed circles). Broken vertical lines indicate withdrawal of LABA.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, because the scope of the present invention will be limited only by the appended claims.

Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "treat", "treating", or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the present invention, the preferred methods and materials are now described. All publications mentioned herein are incorporated herein by reference in their entirety.

Methods for Reducing the Incidence of Asthma Exacerbations

The invention includes methods for reducing the incidence of asthma exacerbations in a subject in need thereof comprising administering a pharmaceutical composition comprising an interleukin-4 receptor (IL-4R) antagonist to the subject. As used herein, the expression "asthma exacerbation" means an increase in the severity and/or frequency and/or duration of one or more symptoms or indicia of asthma. An "asthma exacerbation" also includes any deterioration in the respiratory health of a subject that requires and or is treatable by a therapeutic intervention for asthma (such as, e.g., steroid treatment, inhaled corticosteroid treatment, hospitalization, etc.). According to certain embodiments of the invention, an asthma exacerbation is defined as one or more of the following: (a) a 30% or greater reduction from baseline in morning peak expiratory flow ("AM PEF," as defined elsewhere herein) on two consecutive days; (b) six or more additional reliever puffs of albuterol or levalbuterol in a 24 hour period (compared to baseline) on two consecutive days; and (c) a deterioration of asthma (e.g., as determined by a physician or other medical practitioner) requiring at least one of: (i) systemic (oral and/or parenteral) steroid treatment, or (ii) an increase in inhaled corticosteroids to at least 4 times the baseline level, or (iii) hospitalization.

In certain instances, an asthma exacerbation may be categorized as a "severe asthma exacerbation." A severe asthma exacerbation means an incident requiring immediate intervention in the form of treatment with either systemic corticosteroids or with inhaled corticosteroids at four or more times the dose taken prior to the incident. The general expression "asthma exacerbation" therefore includes and encompasses the more specific subcategory of "severe asthma exacerbations." Accordingly, the invention includes methods for reducing the incidence of severe asthma exacerbations in a patient in need thereof.

A "reduction in the incidence" of an asthma exacerbation means that a subject who has received a pharmaceutical composition of the present invention experiences fewer asthma exacerbations (i.e., at least one fewer exacerbation) after treatment than before treatment, or experiences no asthma exacerbations for at least 4 weeks (e.g., 4, 6, 8, 12, 14, or more weeks) following initiation of treatment with a pharmaceutical composition of the present invention. A "reduction in the incidence" of an asthma exacerbation alternatively means that, following administration of a pharmaceutical composition of the present invention, the likelihood that a subject experiences an asthma exacerbation is decreased by at least 10% (e.g., 10%, 15%, 20%, 25%, 30%, 35%, 40%, 45%, 50%, or more) as compared to a subject who has not received a pharmaceutical composition of the present invention.

Methods for Improving Asthma-Associated Parameters

The invention also includes methods for improving one or more asthma-associated parameters in a subject in need thereof, wherein the methods comprise administering a pharmaceutical composition comprising an interleukin-4 receptor (IL-4R) antagonist to the subject. For purposes of the invention, a reduction in the incidence of an asthma exacerbation (as described above) may correlate with an improvement in one or more asthma-associated parameters; however, such a correlation is not necessarily observed in all cases.

Examples of "asthma-associated parameters" include: (a) forced expiratory volume in 1 second (FEV1); (b) peak expiratory flow rate (PEF), including morning PEF (AM PEF) and evening PEF (PM PEF); (c) use of an inhaled bronchodilator such as albuterol or levalbuterol; (d) five-item Asthma Control Questionnaire (ACQ5) score; (d) nighttime awakenings; and (e) 22-item Sino-Nasal Outcome Test (SNOT-22) score. An "improvement in an asthma-associated parameter" means an increase from baseline of one or more of FEV1, AM PEF or PM PEF, and/or a decrease from baseline of one or more of daily albuterol/levalbuterol use, ACQ5 score, average nighttime awakenings or SNOT-22 score. As used herein, the term "baseline," with regard to an asthma-associated parameter, means the numerical value of the asthma-associated parameter for a patient prior to or at the time of administration of a pharmaceutical composition of the present invention.

To determine whether an asthma-associated parameter has "improved," the parameter is quantified at baseline and at a time point after administration of the pharmaceutical composition of the present invention. For example, an asthma-associated parameter may be measured at day 1, day 2, day 3, day 4, day 5, day 6, day 7, day 8, day 9, day 10, day 11, day 12, day 14, or at week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present invention. The difference between the value of the parameter at a particular time point following initiation of treatment and the value of the parameter at baseline is used to establish whether there has been an "improvement" in the asthma associated parameter (e.g., an increase or decrease, as the case may be, depending on the specific parameter being measured).

The terms "acquire" or "acquiring" as used herein, refer to obtaining possession of a physical entity, or a value, e.g., a numerical value, by "directly acquiring" or "indirectly acquiring" the physical entity or value, such as an asthma-associated parameter. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis").

Information that is acquired indirectly can be provided in the form of a report, e.g., supplied in paper or electronic form, such as from an online database or application (an "App"). The report or information can be provided by, for example, a healthcare institution, such as a hospital or clinic; or a healthcare provider, such as a doctor or nurse.

Forced Expiratory Volume in 1 Second (FEV1).

According to certain embodiments of the invention, administration of an IL-4R antagonist to a patient results in an increase from baseline of forced expiratory volume in 1 second (FEV1). Methods for measuring FEV1 are known in the art. For example, a spirometer that meets the 2005 American Thoracic Society (ATS)/European Respiratory Society (ERS) recommendations can be used to measure FEV1 in a patient. The ATS/ERS Standardization of Spirometry may be used as a guideline. Spirometry is generally performed between 6 and 10 AM after an albuterol withhold of at least 6 hours. Pulmonary function tests are generally measured in the sitting position, and the highest measure is recorded for FEV1 (in liters).

The invention includes therapeutic methods that result in an increase of FEV1 from baseline of at least 0.05 L at week 12 following initiation of treatment with a pharmaceutical composition comprising an anti-IL-4R antagonist. For example, according to the invention, administration of an IL-4R antagonist to a subject in need thereof causes an increase of FEV1 from baseline of about 0.05 L, 0.10 L, 0.12 L, 0.14 L, 0.16 L, 0.18 L, 0.20 L, 0.22 L, 0.24 L, 0.26 L, 0.28 L, 0.30 L, 0.32 L, 0.34 L, 0.36 L, 0.38 L, 0.40 L, 0.42 L, 0.44 L, 0.46 L, 0.48 L, 0.50 L, or more at week 12.

Morning and Evening Peak Expiratory Flow (AM PEF and PM PEF).

According to certain embodiments of the invention, administration of an IL-4R antagonist to a patient results in an increase from baseline of morning (AM) and/or evening (PM) peak expiratory flow (AM PEF and/or PM PEF). Methods for measuring PEF are known in the art. For example, according to one method for measuring PEF, patients are issued an electronic PEF meter for recording morning (AM) and evening (PM) PEF (as well as daily albuterol use, morning and evening asthma symptom scores, and number of nighttime awakenings due to asthma symptoms that require rescue medications). Patients are instructed on the use of the device, and written instructions on the use of the electronic PEF meter are provided to the patients. In addition, a medical professional may instruct the patients on how to record pertinent variables in the electronic PEF meter. AM PEF is generally performed within 15 minutes after arising (between 6 am and 10 am) prior to taking any albuterol. PM PEF is generally performed in the evening (between 6 pm and 10 pm) prior to taking any albuterol. Subjects should try to withhold albuterol for at least 6 hours prior to measuring their PEF. Three PEF efforts are performed by the patient and all 3 values are recorded by the electronic PEF meter. Usually the highest value is used for evaluation. Baseline AM PEF may be calculated as the mean AM measurement recorded for the 7 days prior to administration of the first dose of pharmaceutical composition comprising the IL-4R antagonist, and baseline PM PEF may be calculated as the mean PM measurement recorded for the 7 days prior to administration of the first dose of pharmaceutical composition comprising the IL-4R antagonist.

The invention includes therapeutic methods that result in an increase in AM PEF and/or PM PEF from baseline of at least 1.0 L/min at week 12 following initiation of treatment with a pharmaceutical composition comprising an anti-IL-4R antagonist. For example, according to the invention, administration of an IL-4R antagonist to a subject in need thereof causes an increase in PEF from baseline of about 0.5 L/min, 1.0 L/min, 1.5 L/min, 2.0 L/min, 2.5 L/min, 3.0 L/min, 3.5 L/min, 4.0 L/min, 4.5 L/min, 5.0 L/min, 5.5 L/min, 6.0 L/min, 6.5 L/min, 7.0 L/min, 7.5 L/min, 8.0 L/min, 8.5 L/min, 9.0 L/min, 9.5 L/min, 10.0 L/min, 10.5 L/min, 11.0 L/min, 12.0 L/min, 15 L/min, 20 L/min, or more at week 12.

Albuterol/Levalbuterol Use.

According to certain embodiments of the invention, administration of an IL-4R antagonist to a patient results in a decrease from baseline of daily albuterol or levalbuterol use. The number of albuterol/levalbuterol inhalations can be recorded daily by the patients in a diary, PEF meter, or other recording device. During treatment with the pharmaceutical composition of the invention, use of albuterol/levalbuterol typically may be on an as-needed basis for symptoms, not on a regular basis or prophylactically. The baseline number of albuterol/levalbuterol inhalations/day may be calculated based on the mean for the 7 days prior to administration of the first dose of pharmaceutical composition comprising the IL-4R antagonist.

The invention includes therapeutic methods that result in a decrease in albuterol/levalbuterol use from baseline of at least 0.25 puffs per day at week 12 following initiation of treatment with a pharmaceutical composition comprising an anti-IL-4R antagonist. For example, according to the invention, administration of an IL-4R antagonist to a subject in need thereof causes a decrease in albuterol/levalbuterol use from baseline of about 0.25 puffs per day, 0.50 puffs per day, 0.75 puffs per day, 1.00 puff per day, 1.25 puffs per day, 1.5 puffs per day, 1.75 puffs per day, 2.00 puffs per day, 2.25 puffs per day, 2.5 puffs per day, 2.75 puffs per day, 3.00 puffs per day, or more at week 12.

5-Item Asthma Control Questionnaire (ACQ) Score.

According to certain embodiments of the invention, administration of an IL-4R antagonist to a patient results in a decrease from baseline of five-item Asthma Control Questionnaire (ACQ5) score. The ACQ5 is a validated questionnaire to evaluate asthma control.

The invention includes therapeutic methods that result in a decrease in ACQ5 score from baseline of at least 0.10 points at week 12 following initiation of treatment with a pharmaceutical composition comprising an anti-IL-4R antagonist. For example, according to the invention, administration of an IL-4R antagonist to a subject in need thereof causes a decrease in ACQ score from baseline of about 0.10 points, 0.15 points, 0.20 points, 0.25 points, 0.30 points, 0.35 points, 0.40 points, 0.45 points, 0.50 points, 0.55 points, 0.60 points, 0.65 points, 0.70 points, 0.75 points, 0.80 points, 0.85 points, or more at week 12.

Night-Time Awakenings.

According to certain embodiments of the invention, administration of an IL-4R antagonist to a patient results in a decrease from baseline of average number of nighttime awakenings.

The invention includes therapeutic methods which that in a decrease in average number of nighttime awakenings from baseline of at least about 0.10 times per night at week 12 following initiation of treatment with a pharmaceutical composition comprising an anti-IL-4R antagonist. For example, according to the invention, administration of an IL-4R antagonist to a subject in need thereof causes a decrease in average number of nighttime awakenings from baseline of about 0.10 times per night, 0.15 times per night, 0.20 times per night, 0.25 times per night, 0.30 times per night, 0.35 times per night, 0.40 times per night, 0.45 times per night, 0.50 times per night, 0.55 times per night, 0.60 times per night, 0.65 times per night, 0.70 times per night, 0.75 times per night, 0.80 times per night, 0.85 times per night, 0.90 times per night, 0.95 times per night, 1.0 times per night, 2.0 times per night, or more at week 12.

22-Item Sinonasal Outcome Test (SNOT-22) Score.

According to certain embodiments of the invention, administration of an IL-4R antagonist to a patient results in a decrease from baseline of 22-item Sinonasal Outcome Test (SNOT-22). The SNOT-22 is a validated questionnaire to assess the impact of chronic rhinosinusitis on quality of life (Hopkins et al 2009, Clin. Otolaryngol. 34: 447-454).

The invention includes therapeutic methods that result in a decrease in SNOT-22 score from baseline of at least 1 point at week 12 following initiation of treatment with a pharmaceutical composition comprising an anti-IL-4R antagonist.

For example, according to the invention, administration of an IL-4R antagonist to a subject in need thereof causes a decrease in SNOT-22 score from baseline of about 1, 2, 3, 4, 5, 6, 7, 8, 9, 10, 11, 12, 13 points, or more at week 12.

Methods for Treating Asthma

The invention, according to certain embodiments, provides methods for treating asthma, including, e.g., eosinophilic asthma, in a subject in need thereof, wherein the methods comprise administering a pharmaceutical composition comprising an interleukin-4 receptor (IL-4R) antagonist to the subject. In certain embodiments, the methods of the invention are useful for treating moderate to severe eosinophilic asthma in a subject (e.g., persistent moderate to severe eosinophilic asthma).

According to the invention, a subject is identified as having moderate to severe eosinophilic asthma if the subject exhibits a blood eosinophil level of at least 300 cells per microliter, and/or a sputum eosinophil level of at least 3%. Any methods known and available in the art for measuring blood and/or sputum eosinophil level can be used in the context of the invention to identify a subject as having moderate to severe eosinophilic asthma and who is therefore a suitable subject for the therapeutic methods of the invention.

According to a related aspect of the invention, methods for treating asthma are provided comprising: (a) selecting a patient that exhibits a blood eosinophil level of at least 300 cells per microliter and/or a sputum eosinophil level of at least 3%; and (b) administering to the patient a pharmaceutical composition comprising an IL-4R antagonist.

In another aspect, methods for reducing or eliminating an asthma patient's dependence on inhaled corticosteroids (ICS) and/or long-acting beta-agonists (LABA) during the treatment of moderate-to-severe asthma are provided. In certain embodiments, the methods comprise: selecting a patient with moderate-to-severe asthma that is uncontrolled or partially controlled with a background therapy; administering to the patient a defined dose of an IL-4R antagonist, preferably an anti-IL-4R antibody, for an initial treatment period while maintaining the patient's background therapy for the initial treatment period; and gradually reducing the dosage of one or more components of the background therapy over a subsequent period of treatment while continuing to administer the IL-4R antagonist. The term "background therapy" refers to standard or conventional therapeutic agents known in the art that are used for treating asthma. In certain embodiments, the background therapy comprises an ICS, a LABA or a combination of both. In some embodiments, the dosage of ICS and/or LABA is eliminated or completely withdrawn upon the initial treatment period. For example, a LABA, such as salmeterol or formoterol is administered in an initial treatment period and completely stopped or withdrawn in the subsequent treatment period.

Figure 24:
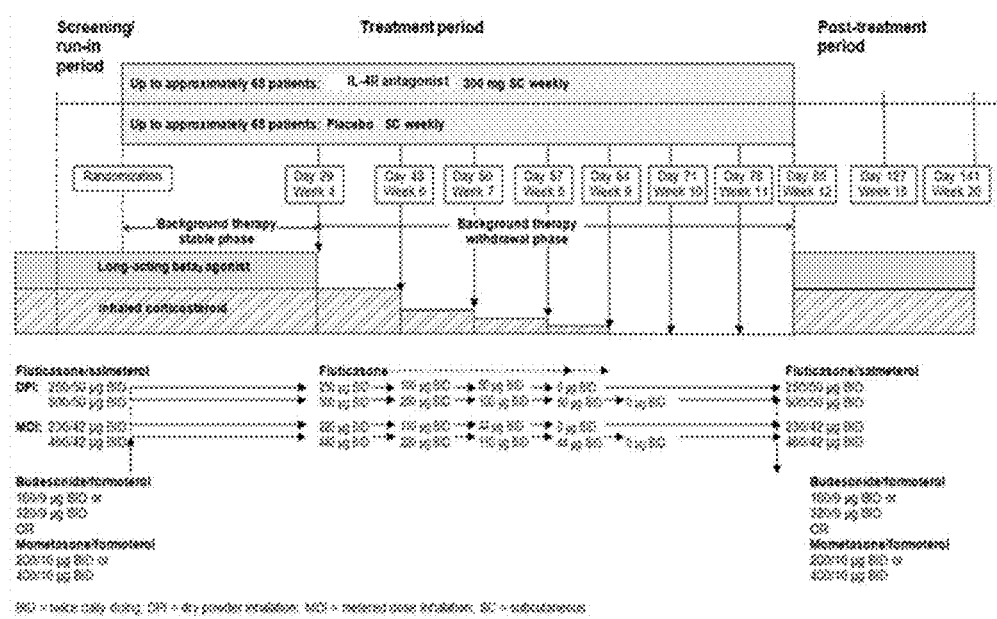
FIG. 24 is a schematic representation of timing and dosing regimens for treatment of asthma patients.

An example of a treatment regimen for a patient with moderate-to-severe asthma is shown in FIG. 24, wherein an IL-4R antagonist is administered to a patient with moderate-to-severe asthma. During an initial treatment period (also called the "stable phase"), a LABA and an ICS are administered to the patient as background therapy. During a subsequent treatment period (also called "withdrawal phase"), the administration of the LABA is stopped, i.e., the LABA is withdrawn or eliminated. The ICS is gradually reduced over the subsequent treatment period until it is eliminated.

In a related aspect, methods for treating asthma comprising an add-on therapy to background therapy with systematic background therapy withdrawal are provided. In certain embodiments, an IL-4R antagonist is administered as an add-on therapy to an asthma patient who is on background therapy for a certain period of time (e.g., 1 week, 2 weeks, 3 weeks, 1 month, 2 months, 5 months, 12 months, 18 months, 24 months, or longer) (also called the "stable phase"). In some embodiments, the background therapy comprises a ICS and/or a LABA. The stable phase is followed by a background therapy withdrawal phase, wherein one or more components comprising the background therapy are withdrawn, or reduced or eliminated, while the add-on therapy continues. In some embodiments, the background therapy may be reduced by about 5%, about 10%, about 20%, about 30%, about 40%, about 50% or by more during the withdrawal phase. The withdrawal phase may last 1 week, 2 weeks, 3 weeks, 4 weeks, 5 weeks, 6 weeks, 7 weeks, 8 weeks, 9 weeks, 10 weeks, 11 weeks, 12 weeks, or more. In a preferred embodiment the background therapy may be reduced by about 5% during the withdrawal phase and the withdrawal phase may last 1 week, 2 weeks, 3 weeks, 4 weeks, 5 weeks, 6 weeks, 7 weeks, 8 weeks, 9 weeks, 10 weeks, 11 weeks, 12 weeks, or more. In a preferred embodiment the background therapy may be reduced by about 10% during the withdrawal phase and the withdrawal phase may last 1 week, 2 weeks, 3 weeks, 4 weeks, 5 weeks, 6 weeks, 7 weeks, 8 weeks, 9 weeks, 10 weeks, 11 weeks, 12 weeks, or more. In a preferred embodiment the background therapy may be reduced by about 20% during the withdrawal phase and the withdrawal phase may last 1 week, 2 weeks, 3 weeks, 4 weeks, 5 weeks, 6 weeks, 7 weeks, 8 weeks, 9 weeks, 10 weeks, 11 weeks, 12 weeks, or more. In a preferred embodiment the background therapy may be reduced by about 30% during the withdrawal phase and the withdrawal phase may last 1 week, 2 weeks, 3 weeks, 4 weeks, 5 weeks, 6 weeks, 7 weeks, 8 weeks, 9 weeks, 10 weeks, 11 weeks, 12 weeks, or more. In a preferred embodiment the background therapy may be reduced by about 40% during the withdrawal phase and the withdrawal phase may last 1 week, 2 weeks, 3 weeks, 4 weeks, 5 weeks, 6 weeks, 7 weeks, 8 weeks, 9 weeks, 10 weeks, 11 weeks, 12 weeks, or more. In a preferred embodiment the background therapy may be reduced by about 50% or more during the withdrawal phase and the withdrawal phase may last 1 week, 2 weeks, 3 weeks, 4 weeks, 5 weeks, 6 weeks, 7 weeks, 8 weeks, 9 weeks, 10 weeks, 11 weeks, 12 weeks, or more.

In some other embodiments, the invention encompasses methods to treat or alleviate conditions or complications associated with asthma, such as chronic rhino sinusitis, allergic rhinitis, allergic fungal rhino sinusitis, allergic broncho-pulmonary aspergillosis, unified airway disease, Churg-Strauss syndrome, vasculitis, chronic obstructive pulmonary disease (COPD), and exercise-induced bronchospasm.

The invention also includes methods for treating persistent asthma. As used herein, the term "persistent asthma" means that the subject has symptoms at least once a week at day and/or at night, with the symptoms lasting a few hours to a few days. In certain alternative embodiments, the persistent asthma is "mildly persistent" (e.g., more than twice a week but less than daily with symptoms severe enough to interfere with daily activities or sleep and/or where pulmonary function is normal or reversible with inhalation of a bronchodilator), "moderately persistent" (e.g., symptoms occurring daily with sleep interrupted at least weekly and/or with pulmonary function moderately abnormal), or "severely persistent" (e.g., continuous symptoms despite the correct use of approved medications and/or where pulmonary function is severely affected).

Interleukin-4 Receptor Antagonists

The methods of the invention comprise administering to a subject in need thereof a therapeutic composition comprising an interleukin-4 receptor (IL-4R) antagonist. As used herein, an "IL-4R antagonist" is any agent that binds to or interacts with IL-4R and inhibits the normal biological signaling function of IL-4R when IL-4R is expressed on a cell in vitro or in vivo. Non-limiting examples of categories of IL-4R antagonists include small molecule IL-4R antagonists, anti-IL-4R aptamers, peptide-based IL-4R antagonists (e.g., "peptibody" molecules), and antibodies or antigen-binding fragments of antibodies that specifically bind human IL-4R.

The term "human IL4R" (hIL-4R) refers to a human cytokine receptor that specifically binds to interleukin-4 (IL-4), such as IL-4Rα (SEQ ID NO:274).

The term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$, and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody" also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds to an antigen to form a complex. Antigen-binding fragments of an antibody may be derived, e.g., from full antibody molecules using any suitable standard techniques, such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment".

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$, (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids that result in a flexible or semi-flexible linkage between adjacent variable and/or constant domains in a single polypeptide molecule, preferably the hinge region may consist of between 2 to 60 amino acids, preferably between 5 to 50, or preferably between 10 to 40 amino acids. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, may be adapted for use in the context of an antigen-binding fragment of an antibody of the invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody" includes antibodies having variable and constant regions derived from human germline immunoglobulin sequences. The human antibodies featured in the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$, or $C_H3$ region, which may be desirable, for example, in production, to improve the yield of the desired antibody form.

An "isolated antibody" means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4R, as used in the context of the present invention, includes antibodies that bind IL-4R or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM, or less than about 0.5 nM, as measured in a surface plasmon resonance assay. An isolated antibody that specifically binds human IL-4R may, however, have cross-reactivity to other antigens, such as IL-4R molecules from other (non-human) species.

The anti-IL-4R antibodies useful for the methods of the invention may comprise one or more amino acid substitutions, insertions, and/or deletions (e.g. 1, 2, 3, 4, 5, 6, 7, 8, 9, or 10 substitutions and/or 1, 2, 3, 4, 5, 6, 7, 8, 9, or 10 insertions and/or 1, 2, 3, 4, 5, 6, 7, 8, 9, or 10 deletions) in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The invention includes methods involving the use of antibodies, and antigen-binding fragments thereof, that are derived from any of the amino acid sequences disclosed herein, wherein one or more amino acids (e.g. 1, 2, 3, 4, 5, 6, 7, 8, 9, or 10 amino acids) within one or more framework and/or one or more (e.g. 1, 2, 3, 4, 5, 6, 7, 8, 9, 10, 11 or 12 with respect to the tetrameric antibody or 1, 2, 3, 4, 5 or 6 with respect to the HCVR and LCVR of an antibody) CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The invention also includes methods involving the use of anti-IL-4R antibodies comprising variants of any of the HCVR, LCVR, and/or CDR amino acid sequences disclosed herein having one or more conservative substitutions. For example, the invention includes the use of anti-IL-4R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance" refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$" refers to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Preparation of Human Antibodies

Methods for generating human antibodies in transgenic mice are known in the art. Any such known methods can be used in the context of the invention to make human antibodies that specifically bind to human IL-4R.

Using VELOCIMMUNE™ technology (see, for example, U.S. Pat. No. 6,596,541, Regeneron Pharmaceuticals) or any other known method for generating monoclonal antibodies, high affinity chimeric antibodies to IL-4R are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc, using standard procedures known to those skilled in the art. The mouse constant regions are replaced with a desired human constant region to generate a fully human antibody featured in the invention, for example wild-type or modified IgG1 or IgG4. While the constant region selected may vary according to specific use, high affinity antigen-binding and target specificity characteristics reside in the variable region.

In general, the antibodies that can be used in the methods of the invention possess high affinities, as described above, when measured by binding to antigen either immobilized on solid phase or in solution phase. The mouse constant regions are replaced with desired human constant regions to generate the fully human antibodies featured in the invention. While the constant region selected may vary according to specific use, high affinity antigen-binding and target specificity characteristics reside in the variable region.

Specific examples of human antibodies or antigen-binding fragments of antibodies that specifically bind IL-4R that can be used in the context of the methods of the present invention include any antibody or antigen-binding fragment that comprises the three heavy chain CDRs (HCDR1, HCDR2 and HCDR3) contained within a heavy chain variable region (HCVR) having an amino acid sequence selected from the group consisting of SEQ ID NOs: 2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258, and 262. The antibody or antigen-binding fragment may comprise the three light chain CDRs (LCVR1, LCVR2, LCVR3) contained within a light chain variable region (LCVR) having an amino acid sequence selected from the group consisting of SEQ ID NOs: 10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260, and 264. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches.

See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In certain embodiments of the invention, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, and 262/264.

In certain embodiments of the invention, the antibody or antigen-binding fragment thereof comprises six CDRs (HCDR1/HCDR2/HCDR3/LCDR1/LCDR2/LCDR3) having the amino acid sequences selected from the group consisting of SEQ ID NOs: 4/6/8/12/14/16; 28/30/32/36/38/40; 52/54/56/60/62/64; 76/78/80/84/86/88; 100/102/104/108/110/112; 124/126/128/132/134/136; 148/150/152/156/158/160; 172/174/176/180/182/184; 196/198/200/204/206/208; 220/222/224/228/230/232; and 244/246/248/252/254/256.

In certain embodiments of the invention, the antibody or antigen-binding fragment thereof comprises HCVR/LCVR amino acid sequence pairs selected from the group consisting of SEQ ID NOs: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, and 262/264.

Pharmaceutical Compositions

The invention includes methods that comprise administering an IL-4R antagonist to a patient, wherein the IL-4R antagonist is contained within a pharmaceutical composition. The pharmaceutical compositions featured in the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient according to the methods of the invention may vary depending upon the age and the size of the patient, symptoms, conditions, route of administration, and the like. The preferred dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical compositions featured in the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, intra-tracheal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the invention can be delivered subcutaneously or intravenously with a standard needle and syringe. In addition, with respect to subcutaneous delivery, a pen delivery device readily has applications in delivering a pharmaceutical composition of the invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN™ (Dey, L. P.), and the HUMIRA™ Pen (Abbott Labs, Abbott Park Ill.), to name only a few.

For direct administration to the sinuses, the pharmaceutical compositions of the invention may be administered using, e.g., a microcatheter (e.g., an endoscope and microcatheter), an aerosolizer, a powder dispenser, a nebulizer or an inhaler. The methods include administration of an IL-4R antagonist to a subject in need thereof, in an aerosolized formulation. For example, aerosolized antibodies to IL-4R may be administered to treat asthma in a patient. Aerosolized antibodies can be prepared as described in, for example, U.S. Pat. No. 8,178,098, incorporated herein in its entirety.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the invention are disclosed, e.g., in US Patent Application Publication No. 2012/0097565.

Dosage

The amount of IL-4R antagonist (e.g., anti-IL-4R antibody) administered to a subject according to the methods of the invention is, generally, a therapeutically effective amount. As used herein, the phrase "therapeutically effective amount" means an amount of IL-4R antagonist that results in one or more of: (a) a reduction in the incidence of asthma exacerbations; (b) an improvement in one or more asthma-associated parameters (as defined elsewhere herein); and/or (c) a detectable improvement in one or more symptoms or indicia of an upper airway inflammatory condition. A "therapeutically effective amount" also includes an amount of IL-4R antagonist that inhibits, prevents, lessens, or delays the progression of asthma in a subject.

In the case of an anti-IL-4R antibody, a therapeutically effective amount can be from about 0.05 mg to about 600 mg, e.g., about 0.05 mg, about 0.1 mg, about 1.0 mg, about 1.5 mg, about 2.0 mg, about 3.0 mg, about 5.0 mg, about 7.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 300 mg of an anti-IL-4R antibody is administered.

The amount of IL-4R antagonist contained within the individual doses may be expressed in terms of milligrams of antibody per kilogram of patient body weight (i.e., mg/kg). For example, the IL-4R antagonist may be administered to a patient at a dose of about 0.0001 to about 10 mg/kg of patient body weight.

Combination Therapies

The methods of the invention, according to certain embodiments, comprise administering to the subject one or more additional therapeutic agents in combination with the IL-4R antagonist. As used herein, the expression "in combination with" means that the additional therapeutic agents are administered before, after, or concurrent with the pharmaceutical composition comprising the IL-4R antagonist. In some embodiments, the term "in combination with" includes sequential or concomitant administration of an IL-4R antagonist and a second therapeutic agent. The present invention includes methods to treat asthma or an associated condition or complication or to reduce at least one exacerbation, comprising administration of an IL-4R antagonist in combination with a second therapeutic agent for additive or synergistic activity.

For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes, or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, or about 72 hours after the administration of the pharmaceutical composition comprising the IL-4R antagonist. Administration "concurrent" with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

The additional therapeutic agent may be, e.g., another IL-4R antagonist, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), a TNF antagonist, an IL-8 antagonist, an IL-9 antagonist, an IL-17 antagonist, an IL-5 antagonist, an IgE antagonist, a CD48 antagonist, a leukotriene inhibitor, an anti-fungal agent, an NSAID, a long-acting beta$_2$ agonist (e.g., salmeterol or formoterol), an inhaled corticosteroid (e.g., fluticasone or budesonide), a systemic corticosteroid (e.g., oral or intravenous), methylxanthine, nedocromil sodium, cromolyn sodium, or combinations thereof. For example, in certain embodiments, the pharmaceutical composition comprising an IL-4R antagonist is administered in combination with a combination comprising a long-acting beta$_2$ agonist and an inhaled corticosteroid (e.g., fluticasone+salmeterol [e.g., Advair® (GlaxoSmithKline)]; or budesonide+formoterol [e.g., Symbicort® (Astra Zeneca)]).

Administration Regimens

According to certain embodiments of the invention, multiple doses of an IL-4R antagonist may be administered to a subject over a defined time course. Such methods comprise sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks, or months). The present invention includes methods that comprise sequentially administering to the patient a single initial dose of an IL-4R antagonist, followed by one or more secondary doses of the IL-4R antagonist, and optionally followed by one or more tertiary doses of the IL-4R antagonist.

The invention includes methods comprising administering to a subject a pharmaceutical composition comprising an IL-4R antagonist at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of a pharmaceutical composition comprising an anti-IL-4R antibody, once a week dosing of an amount of about 75 mg, 150 mg, or 300 mg, can be employed. In other embodiments involving the administration of a pharmaceutical composition comprising an anti-IL-4R antibody, once every two weeks dosing of an amount of about 75 mg, 150 mg, or 300 mg, can be employed. In other embodiments involving the administration of a pharmaceutical composition comprising an anti-IL-4R antibody, once every three weeks dosing of an amount of about 75 mg, 150 mg, or 300 mg, can be employed. In other embodiments involving the administration of a pharmaceutical composition comprising an anti-IL-4R antibody, once every four weeks dosing of an amount of about 75 mg, 150 mg, or 300 mg, can be employed. In other embodiments involving the administration of a pharmaceutical composition comprising an anti-IL-4R antibody, once every five weeks dosing of an amount of about 75 mg, 150 mg, or 300 mg, can be employed. In other embodiments involving the administration of a pharmaceutical composition comprising an anti-IL-4R antibody, once every six weeks dosing of an amount of about 75 mg, 150 mg, or 300 mg, can be employed. In other embodiments involving the administration of a pharmaceutical composition comprising an anti-IL-4R antibody, once every eight weeks dosing of an amount of about 75 mg, 150 mg, or 300 mg, can be employed. In other embodiments involving the administration of a pharmaceutical composition comprising an anti-IL-4R antibody, once every twelve weeks dosing of an amount of about 75 mg, 150 mg, or 300 mg, can be employed. A preferred route of administration is subcutaneous.

The term "week" or "weeks" refers to a period of (n×7 days)±2 days, preferably (n×7 days)±1 day, more preferably (n×7 days), wherein "n" designates the number of weeks, e.g. 1, 2, 3, 4, 5, 6, 8, 12 or more.

The terms "initial dose," "secondary doses," and "tertiary doses," refer to the temporal sequence of administration of the IL-4R antagonist. Thus, the "initial dose" is the dose that is administered at the beginning of the treatment regimen (also referred to as the "baseline dose"); the "secondary doses" are the doses that are administered after the initial dose; and the "tertiary doses" are the doses that are administered after the secondary doses. The initial, secondary, and tertiary doses may all contain the same amount of IL-4R antagonist, but generally may differ from one another in terms of frequency of administration. In certain embodiments, however, the amount of IL-4R antagonist contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses"). In one embodiment, the maintenance dose may be lower than the loading dose. For example, one or more loading doses of 600 mg of IL-4R antagonist may be administered followed by maintenance doses of about 75 mg to about 300 mg.

In one exemplary embodiment of the invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose" means, in a sequence of multiple administrations, the dose of IL-4R antagonist that is administered to a patient prior to the administration of the very next dose in the sequence with no intervening doses.

The methods may comprise administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The invention includes methods comprising sequential administration of an IL-4R antagonist and a second therapeutic agent, to a patient to treat asthma or an associated condition. In some embodiments, the methods comprise administering one or more doses of an IL-4R antagonist followed by one or more doses (e.g., 2, 3, 4, 5, 6, 7, 8, or more) of a second therapeutic agent. For example, one or more doses of about 75 mg to about 300 mg of the IL-4R antagonist may be administered after which one or more doses (e.g., 2, 3, 4, 5, 6, 7, 8, or more) of a second therapeutic agent (e.g., an inhaled corticosteroid or a beta2-agonist or any other therapeutic agent, as described elsewhere herein) may be administered to treat, alleviate, reduce or ameliorate one or more symptoms of asthma. In some embodiments, the IL-4R antagonist is administered at one or more doses (e.g., 2, 3, 4, 5, 6, 7, 8, or more) resulting in an improvement in one or more asthma-associated parameters followed by the administration of a second therapeutic agent to prevent recurrence of at least one symptom of asthma. Alternative embodiments pertain to concomitant administration of an IL-4R antagonist and a second therapeutic agent. For example, one or more doses (e.g., 2, 3, 4, 5, 6, 7, 8, or more) of an IL-4R antagonist are administered and a second therapeutic agent is administered at a separate dosage at a similar or different frequency relative to the IL-4R antagonist. In some embodiments, the second therapeutic agent is administered before, after or concurrently with the IL-4R antagonist.

Treatment Populations

The methods of the invention comprise administering to a subject in need thereof a therapeutic composition comprising an IL-4R antagonist. The expression "a subject in need thereof" means a human or non-human animal that exhibits one or more symptoms or indicia of asthma (e.g., eosinophilic asthma, including moderate to severe eosinophilic asthma), or who has been diagnosed with asthma. For example, "a subject in need thereof" may include, e.g., subjects who, prior to treatment, exhibit (or have exhibited) one or more asthma-associated parameter such as, e.g., impaired FEV1 (e.g., less than 2.0 L), impaired AM PEF (e.g., less than 400 L/min), impaired PM PEF (e.g., less than 400 L/min), an ACQ5 score of at least 2.5, at least 1 nighttime awakenings per night, and/or a SNOT-22 score of at least 20. In various embodiments, the methods may be used to treat mild, moderate-to-severe, and severe asthma in patients in need thereof.

In a related embodiment, a "subject in need thereof" may be a subject who, prior to receiving an IL-4R antagonist, has been prescribed or is currently taking a combination of inhaled corticosteroid (ICS)/long-acting beta$_2$-adronergic antagonist (LABA). Examples of ICS/LABA therapies include fluticasone/salmeterol combination therapy and budesonide/formotorol combination therapy. For example, the invention includes methods that comprise administering an IL-4R antagonist to a patient who has been taking a regular course of ICS/LABA for two or more weeks immediately preceding the administration of the IL-4R antagonist (such prior treatments are referred to herein as "background treatments"). The invention includes therapeutic methods in which background treatments are discontinued at the time of, or just before (e.g., 1 day to 2 weeks prior to) the first administration of the IL-4R antagonist. Alternatively, background treatments may be continued in combination with administration of the IL-4R antagonist. In yet other embodiments, the amount of the ICS component, the LABA component, or both, is gradually decreased prior to or after the start of IL-4R antagonist administration. In some embodiments, the invention includes methods to treat patients with persistent asthma for at least 12 months. In one embodiment, a patient with persistent asthma may be resistant to treatment by a therapeutic agent, such as a corticosteroid, and may be administered an IL-4R antagonist according to the present methods.

In some embodiments, a "subject in need thereof" may be a subject with elevated levels of an asthma-associated biomarker. Examples of asthma-associated biomarkers include, but are not limited to, IgE, thymus and activation regulated chemokine (TARC), eotaxin-3, CEA, YKL-40, and periostin. In some embodiments, a "subject in need thereof" may be a subject with blood eosinophils≥300/µl or with sputum eosinophil level≥3%. In one embodiment, a "subject in need thereof" may be a subject with elevated level of bronchial or airway inflammation as measured by the fraction of exhaled nitric oxide (FeNO).

For purposes of the invention, a normal IgE level in healthy subjects is less than about 100 kU/L (e.g., as measured using the ImmunoCAP® assay [Phadia, Inc. Portage, Mich.]). Thus, the invention involves methods comprising selecting a subject who exhibits an elevated serum IgE level, which is a serum IgE level greater than about 100 kU/L, greater than about 150 kU/L, greater than about 500 kU/L, greater than about 1000 kU/L, greater than about 1500 kU/L, greater than about 2000 kU/L, greater than about 2500 kU/L, greater than about 3000 kU/L, greater than about 3500 kU/L, greater than about 4000 kU/L, greater than about 4500 kU/L, or greater than about 5000 kU/L, and administering to the subject a pharmaceutical composition comprising a therapeutically effective amount of an IL-4R antagonist.

TARC levels in healthy subjects are in the range of 106 ng/L to 431 ng/L, with a mean of about 239 ng/L. (An exemplary assay system for measuring TARC level is the TARC quantitative ELISA kit offered as Cat. No. DDN00 by R&D Systems, Minneapolis, Minn.) Thus, the invention involves methods comprising selecting a subject who exhibits an elevated TARC level, which is a serum TARC level greater than about 431 ng/L, greater than about 500 ng/L, greater than about 1000 ng/L, greater than about 1500 ng/L, greater than about 2000 ng/L, greater than about 2500 ng/L, greater than about 3000 ng/L, greater than about 3500 ng/L, greater than about 4000 ng/L, greater than about 4500 ng/L, or greater than about 5000 ng/L, and administering to the subject a pharmaceutical composition comprising a therapeutically effective amount of an IL-4R antagonist.

Eotaxin-3 belongs to a group of chemokines released by airway epithelial cells, which is up regulated by the Th2 cytokines IL-4 and IL-13 (Lilly et al 1999, J. Allergy Clin. Immunol. 104: 786-790). The invention includes methods comprising administering an IL-4R antagonist to treat patients with elevated levels of eotaxin-3, such as more than about 100 pg/ml, more than about 150 pg/ml, more than about 200 pg/ml, more than about 300 pg/ml, or more than about 350 pg/ml. Serum eotaxin-3 levels may be measured, for example, by ELISA.

Periostin is an extracellular matrix protein involved in the Th2-mediated inflammatory processes. Periostin levels are found to be up regulated in patients with asthma (Jia et al 2012 J Allergy Clin Immunol. 130:647-654.e10. doi: 10.1016/j.jaci.2012.06.025. Epub 2012 Aug. 1). The present invention includes methods comprising administering an IL-4R antagonist to treat patients with elevated levels of periostin.

Fractional exhaled NO (FeNO) is a biomarker of bronchial or airway inflammation. FeNO is produced by airway epithelial cells in response to inflammatory cytokines including IL-4 and IL-13 (Alwing et al 1993, Eur. Respir. J. 6: 1368-1370). FeNO levels in healthy adults range from 2 to 30 parts per billion (ppb). An exemplary assay for measuring FeNO is by using a NIOX instrument by Aerocrine AB, Solna, Sweden. The assessment may be conducted prior to spirometry and following a fast of at least an hour.

The invention includes methods comprising administering an IL-4R antagonist to patients with elevated levels of exhaled NO (FeNO), such as more than about 30 ppb, more than about 31 ppb, more than about 32 ppb, more than about 33 ppb, more than about 34 ppb, or more than about 35 ppb.

Carcinoembryogenic antigen (CEA) is a tumor marker that is found correlated to non-neoplastic diseases of the lung (Marechal et al 1988, Anticancer Res. 8: 677-680). CEA levels in serum may be measured by ELISA. The invention includes methods comprising administering an IL-4R antagonist to patients with elevated levels of CEA, such as more than about 1.0 ng/ml, more than about 1.5 ng/ml, more than about 2.0 ng/ml, more than about 2.5 ng/ml, more than about 3.0 ng/ml, more than about 4.0 ng/ml, or more than about 5.0 ng/ml.

YKL-40 [named for its N-terminal amino acids tyrosine (Y), lysine (K) and leucine (L) and its molecular mass of 40 kD] is a chitinase-like protein found to be up regulated and correlated to asthma exacerbation, IgE, and eosinophils (Tang et al 2010 Eur. Respir. J. 35: 757-760). Serum YKL-40 levels are measured by, for example, ELISA. The invention includes methods comprising administering an IL-4R antagonist to patients with elevated levels of YKL-40, such as more than about 40 ng/ml, more than about 50 ng/ml, more than about 100 ng/ml, more than about 150 ng/ml, more than about 200 ng/ml, or more than about 250 ng/ml.

Induced sputum eosinophils and neutrophils are well-established direct markers of airway inflammation (Djukanovic et al 2002, Eur. Respire. J. 37: 1S-2S). Sputum is induced with inhalation of hypertonic saline solution and processed for cell counts according to methods known in the art, for example, the guidelines of European Respiratory Society. The invention includes methods comprising administering an IL-4R antagonist to patients with elevated levels of sputum eosinophils, such as more than about 2.5% or more than about 3%.

Methods for Assessing Pharmacodynamic Asthma-Associated Parameters

The invention also includes methods for assessing one or more pharmacodynamic asthma-associated parameters a subject in need thereof, caused by administration of a pharmaceutical composition comprising an interleukin-4 receptor (IL-4R) antagonist. A reduction in the incidence of an asthma exacerbation (as described above) or an improvement in one or more asthma-associated parameters (as described above) may correlate with an improvement in one or more pharmacodynamic asthma-associated parameters; however, such a correlation is not necessarily observed in all cases.

Examples of "pharmacodynamic asthma-associated parameters" include, for example, the following: (a) biomarker expression levels; (b) serum protein and RNA analysis; (c) induced sputum eosinophils and neutrophil levels; (d) exhaled nitric oxide (FeNO); and (e) blood eosinophil count. An "improvement in a pharmacodynamic asthma-associated parameter" means, for example, a decrease from baseline of one or more biomarkers, such as TARC, eotaxin-3 or IgE, a decrease in sputum eosinophils or neutrophils, FeNO, or blood eosinophil count. As used herein, the term "baseline," with regard to a pharmacodynamic asthma-associated parameter, means the numerical value of the pharmacodynamic asthma-associated parameter for a patient prior to or at the time of administration of a pharmaceutical composition featured in the invention.

To assess a pharmacodynamic asthma-associated parameter, the parameter is quantified at baseline and at a time point after administration of the pharmaceutical composition of the present invention. For example, a pharmacodynamic asthma-associated parameter may be measured at day 1, day 2, day 3, day 4, day 5, day 6, day 7, day 8, day 9, day 10, day 11, day 12, day 14, or at week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present invention. The difference between the value of the parameter at a particular time point following initiation of treatment and the value of the parameter at baseline is used to establish whether there has been change, such as an "improvement", in the pharmacodynamic asthma-associated parameter (e.g., an increase or decrease, as the case may be, depending on the specific parameter being measured).

In certain embodiments, administration of an IL-4R antagonist to a patient causes a change, such as a decrease or increase, in expression of a particular biomarker. Asthma associated biomarkers include the following: (a) total IgE; (b) thymus and activation-regulated chemokine (TARC); (c) YKL-40; and (d) carcinoembryonic antigen (CEA, also known as CEA cell adhesion molecule 5 [CEACAM5]) in serum and (e) eotaxin-3 in plasma. For example, administration of an IL-4R antagonist to an asthma patient can cause one or more of a decrease in TARC or eotaxin-3 levels, or a decrease in total serum IgE levels. The decrease can be detected at week 1, week 2, week 3, week 4, week 5, or longer following administration of the IL-4R antagonist. Biomarker expression can be assayed by methods known in the art. For example, protein levels can be measured by ELISA (Enzyme Linked Immunosorbent Assay), or RNA levels can be measured by reverse transcription coupled to polymerase chain reaction (RT-PCR).

Biomarker expression, as discussed above, can be assayed by detection of protein or RNA in serum. The serum samples can also be used to monitor additional protein or RNA biomarkers related to response to treatment with an IL-4R antagonist, IL-4/IL-13 signaling, asthma, atopy or eosinophilic diseases (e.g., by measuring soluble IL-4Rα, IL-4, IL-13, periostin). In some embodiments, RNA samples are used to determine RNA levels (non-genetic analysis), e.g., RNA levels of biomarkers; and in other embodiments, RNA samples are used for transcriptome sequencing (e.g., genetic analysis).

EXAMPLES

The following examples are put forth so as to provide those of ordinary skill in the art with a complete disclosure and description of how to make and use the methods and compositions featured in the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human IL-4R

Human anti-hIL-4R antibodies were generated as described in U.S. Pat. No. 7,608,693. Table 1 sets forth the sequence identifiers for the heavy and light chain variable region amino acid sequence pairs, and CDR amino acid sequences, of selected anti-IL-4R antibodies and their corresponding antibody designations.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H095-a | 2 | 4 | 6 | 8 | 10 | 12 | 14 | 16 |
| H1H095-b | 18 | 4 | 6 | 8 | 20 | 12 | 14 | 16 |
| H1H095-c | 22 | 4 | 6 | 8 | 24 | 12 | 14 | 16 |
| H1H097-a | 26 | 28 | 30 | 32 | 34 | 36 | 38 | 40 |
| H1H097-b | 42 | 28 | 30 | 32 | 44 | 36 | 38 | 40 |
| H1H097-c | 46 | 28 | 30 | 32 | 48 | 36 | 38 | 40 |
| H1H093-a | 50 | 52 | 54 | 56 | 58 | 60 | 62 | 64 |
| H1H093-b | 66 | 52 | 54 | 56 | 68 | 60 | 62 | 64 |
| H1H093-c | 70 | 52 | 54 | 56 | 72 | 60 | 62 | 64 |
| H1H093-d | 74 | 76 | 78 | 80 | 82 | 84 | 86 | 88 |
| H1H093-e | 90 | 76 | 78 | 80 | 92 | 84 | 86 | 88 |
| H1H093-f | 94 | 76 | 78 | 80 | 96 | 84 | 86 | 88 |
| H1H094-a | 98 | 100 | 102 | 104 | 106 | 108 | 110 | 112 |
| H1H094-b | 114 | 100 | 102 | 104 | 116 | 108 | 110 | 112 |
| H1H094-c | 118 | 100 | 102 | 104 | 120 | 108 | 110 | 112 |
| H1H096-a | 122 | 124 | 126 | 128 | 130 | 132 | 134 | 136 |
| H1H096-b | 138 | 124 | 126 | 128 | 140 | 132 | 134 | 136 |
| H1H096-c | 142 | 124 | 126 | 128 | 144 | 132 | 134 | 136 |
| H1H098-a | 146 | 148 | 150 | 152 | 154 | 156 | 158 | 160 |
| H1H098-b | 162 | 148 | 150 | 152 | 164 | 156 | 158 | 160 |
| H1H098-c | 166 | 148 | 150 | 152 | 168 | 156 | 158 | 160 |
| H1H099-a | 170 | 172 | 174 | 176 | 178 | 180 | 182 | 184 |
| H1H099-b | 186 | 172 | 174 | 176 | 188 | 180 | 182 | 184 |
| H1H099-c | 190 | 172 | 174 | 176 | 192 | 180 | 182 | 184 |
| H4H083-a | 194 | 196 | 198 | 200 | 202 | 204 | 206 | 208 |
| H4H083-b | 210 | 196 | 198 | 200 | 212 | 204 | 206 | 208 |
| H4H083-c | 214 | 196 | 198 | 200 | 216 | 204 | 206 | 208 |
| H4H121-a | 218 | 220 | 222 | 224 | 226 | 228 | 230 | 232 |
| H4H121-b | 234 | 220 | 222 | 224 | 236 | 228 | 230 | 232 |
| H4H121-c | 238 | 220 | 222 | 224 | 240 | 228 | 230 | 232 |
| H4H118-a | 242 | 244 | 246 | 248 | 250 | 252 | 254 | 256 |
| H4H118-b | 258 | 244 | 246 | 248 | 260 | 252 | 254 | 256 |
| H4H118-c | 262 | 244 | 246 | 248 | 264 | 252 | 254 | 256 |

The exemplary IL-4R antagonist used in the following Examples is the human anti-IL-4R antibody designated in Table 1 as H1H098-b (also referred to herein as "mAb1").

Example 2

Clinical Trial of Subcutaneously Administered Anti-IL-4R Antibody (mAb1) in Patients with Persistent Moderate-to-Severe Eosinophilic Asthma, Including Asthma Patients with Chronic Hyperplastic Eosinophilic Sinusitis A. Study Objectives and Overview A randomized, placebo-controlled, double-blind, parallel group study was conducted with once-a-week subcutaneous administration of either 300 mg mAb1 or placebo for 12 weeks to patients with persistent moderate-to-severe eosinophilic asthma who were partially controlled/uncontrolled by inhaled corticosteroid (ICS) and long-acting beta2 agonist (LABA) therapy. The primary objective of the study was to investigate the effects of mAb1 administered subcutaneously once weekly for 12 weeks as compared to placebo on reducing the incidence of asthma exacerbations in patients with persistent moderate-to-severe eosinophilic asthma. The secondary objectives of the study were to assess the safety and tolerability of mAb1 administered subcutaneously once weekly for 12 weeks in patients with persistent moderate to severe eosinophilic asthma, and to assess mAb1 serum concentrations following once weekly subcutaneous dosing for 12 weeks in patients with persistent moderate to severe eosinophilic asthma.

Prior to screening, patients were required to be on a stable dose of any of the following doses and formulations of ICS/LABA combination therapy (also called "background therapy") for at least 1 month:

Fluticasone/Salmeterol Combination Therapy
  Advair® Diskus—dry powder inhaler (DPI): 250/50 ug BID or 500/50 ug BID; or
  Advair® HFA—metered dose inhaler (MDI): 230/42 ug BID or 460/42 ug BID; or
Budesonide/formoterol combination therapy (Symbicort® 160/9 ug BID or 320/9 ug BID); or
Mometasone/formoterol combination therapy (Dulera® 200/10 ug BID or 400/10 ug BID)

Patients who were on budesonide/formoterol or mometasone/formoterol were switched to an equivalent dose of fluticasone/salmeterol at randomization (Day 1) and patients who had been on fluticasone/salmeterol remained on the same as background therapy.

Patients who satisfied the inclusion and exclusion criteria (see below) were randomized to one of the following treatments: 300 mg of mAb1 administered subcutaneously once weekly for 12 weeks; or placebo administered subcutaneously once weekly for 12 weeks.

The study comprised a 2-week screening period, a 12-week treatment period comprising a 4-week background therapy stable phase and an 8-week background therapy withdrawal phase post-randomization, followed by an 8-week post-treatment follow-up period.

Algorithm for Background Therapy (ICS/LABA) Withdrawal:

Patients remained on BID fluticasone/salmeterol background therapy for 4 weeks after starting add-on therapy or treatment of 300 mg mAb1 (or placebo). At 4 weeks post-randomization, patients were switched from the BID fluticasone/salmeterol combination therapy to an equivalent ICS dose of fluticasone monotherapy (comprising either Flovent® Diskus—DPI formulation of 250 ug or 500 ug BID; or Flovent® HFA—MDI formulation of 220 ug or 440 ug BID). The LABA component (i.e., salmeterol) was discontinued. At subsequent visits, beginning with week 6, the fluticasone dose was reduced by approximately 50%, provided the patient did not meet any of the criteria for an asthma exacerbation (as defined below). If no asthma exacerbations occurred, the ICS withdrawal proceeded according to the following dosing schedule:

| Background therapy stable phase | Background therapy withdrawal phase | | | | |
|---|---|---|---|---|---|
| | Week 4 | Week 6 | Week 7 | Week 8 | Week 9 |
| Fluticasone/salmeterol (DPI): 250/50 μg BID | Fluticasone (DPI): 250 μg BID | 100 μg BID | 50 μg BID | 0 μg BID | 0 μg BID |
| Fluticasone/salmeterol (DPI): 500/50 μg BID | Fluticasone (DPI): 500 μg BID | 250 μg BID | 100 μg BID | 50 μg BID | 0 μg BID |
| Fluticasone/salmeterol (MDI): 230/42 μg BID | Fluticasone (MDI): 220 μg BID | 110 μg BID | 44 μg BID | 0 μg BID | 0 μg BID |
| Fluticasone/salmeterol (MDI): 460/42 μg BID | Fluticasone (MDI): 440 μg BID | 220 μg BID | 110 μg BID | 44 μg BID | 0 μg BID |

Upon completing 12 weeks of treatment with investigational product (or after early discontinuation), patients were placed on their original dose of fluticasone/salmeterol, budesonide/formoterol, or mometasone/formoterol (dose at study entry) and albuterol or levalbuterol as-needed to control their symptoms for an additional 8 weeks off study medication before a final safety evaluation.

Adult patients were included in the study based on the following criteria: (1) physician's diagnosis of persistent asthma for at least ≥12 months based on the Global Initiative for Asthma (GINA) 2009 Guidelines, whose airway inflammation is likely to be eosinophilic; and (2) whose asthma is partially controlled or uncontrolled in inhaled corticosteroids/long acting beta-agonists combination therapy according to the following criteria: (i) stable dose of either fluticasone/salmeterol combination therapy (DPI formulation: 250/50 μg BID or 500/50 μg BID or MDI formulation: 230/42 μg BID or 460/42 μg BID), or budesonide/formoterol combination therapy (160/9 μg BID or 320/9 μg BID), or mometasone/formoterol combination therapy (200/10 μg BID or 400/10 μg BID) for at least 1 month prior to screening; (ii) blood eosinophils 300 cells/μl or sputum eosinophils≥3% during the screening phase; (iii) Juniper asthma control questionnaire (5-question version, ACQ) score of ≥1.5 and ≤3.0 at screening; (iv) FEV1≥50% predicted normal during the screening phase (3 attempts maximum) and on the randomization day prior to the first dose (3 attempts maximum); (v) has had within the 2 years prior to screening either treatment with one or more systemic (oral and/or parenteral) steroid bursts for worsening asthma or in-patient hospitalization or an emergency care visit for worsening asthma; and (vi) documented history of reversibility within 12 months of screening that meets the criterion—at least 12% and 200 mL in FEV1 after 200 μg to 400 μg (2 to 4 inhalations) of albuterol during the screening phase (3 attempts maximum), or documented history of a positive methacholine challenge (PD20 methacholine≤8 mg) within 12 months prior to screening. Patients with moderate-to-severe asthma that is partially controlled or uncontrolled with moderate to high doses of combination therapy with inhaled corticosteroids and long-acting beta agonists (ADVAIR®, SYMBICORT® or DULERA®) and with blood eosinophils greater than or equal to 300 cells per microliter, or sputum eosinophils greater than or equal to 3% during the screening phase, were included in the study.

Patients who met all the inclusion criteria were screened for the following exclusion criteria: (1) patients less than 18 years of age or greater than 65 years of age; (2) clinically relevant abnormal laboratory values suggesting an unknown disease and requiring further evaluation; (3) chronic obstructive pulmonary disease (COPD) and/or other lung diseases impairing pulmonary function tests; (4) patients requiring beta-adrenergic receptor blockers for any reason; (5) current smoker or cessation of smoking within the 6 months prior to screening; (6) previous smoking with a smoking history>10 cigarette pack-years; (7) in-patient hospitalization or emergency care visit due to asthma exacerbation in the 2 months prior to screening; (8) plans to begin allergen immunotherapy within the study period; (9) exposure to another investigative antibody within a time period prior to screening that is less than 5 half-lives of the antibody but not less than 30 days, or if the half life of the antibody is not known, then a time period prior to screening that is at least 6 months; (10) previous enrollment into the current study; (11) patient was the investigator, his/her family member or an employee at the investigational site; (12) known or suspected non-compliance, alcohol or drug abuse; (13) inability to follow the procedures of the study (e.g., due to language problems or psychological disorders); (14) reversal of sleep pattern (e.g., night shift worker); (15) treatment with drugs known to prolong QTc interval; (16) concomitant severe disease(s) for which the use of ICS (e.g., active or inactive pulmonary tuberculosis) or LABA (e.g., diabetes, cardiovascular diseases, hypertension, hyperthyroidism, thyrotoxicosis, etc) are contra-indicated; (17) use of injectable glucocorticosteroids or oral systemic glucocorticosteroids within 2 months prior to screening or more than 3 courses within the 6 months prior to screening; (18) pre-treatment with variable doses of ICS, either alone or in combination with a non-steroidal controller (other than fluticasone/salmeterol combination therapy, budesonide/formoterol combination therapy, or mometasone/formoterol combination therapy); (19) patients receiving prohibited concomitant medications (listed below); (20) known allergy to doxycycline or related compounds; (21) pregnancy or intention to become pregnant during the course of the study, breast feeding or unwillingness to use an effective method of contraception; and (22) recent history of a parasitic infection or travel to a parasitic endemic area within 6 months prior to screening.

Patients remained on a constant dose of the background asthma therapy for the first four weeks of the study after which the dose of background therapy was reduced gradually. First, the long-acting beta agonist component of the background therapy was withdrawn at week 4, and then the inhaled corticosteroid dose was reduced by half every 2 weeks until week 12. Patients continued on study treatment until the end of the study or until they were withdrawn due to an asthma exacerbation or for any other reason.

B. Study Treatments

Investigational Product: Sterile mAb1 150 mg/mL solution for SC injection was provided in a 5 mL glass vial. Each vial contained a withdrawable volume of 2 mL. A 300 mg dose was administered subcutaneously at the study site once weekly in the morning for 12 weeks. Placebo: Sterile placebo for SC injection was provided in an identically matched 5 mL glass vial. Each vial contained a withdrawable volume of 2 mL. Placebo was administered subcutaneously at the study site once weekly in the morning for 12 weeks.

The following concomitant medications were not allowed during the duration of the study: any other inhaled steroid other than fluticasone/salmeterol combination therapy or fluticasone administered per the protocol (or budesonide/formoterol or mometasone/formoterol during the screening period); systemic or ocular steroids; LABAs other than the salmeterol component of the fluticasone/salmeterol combination therapy administered per the protocol; any other ICS/LABA combination products other than those given above; any inhaled anti-cholinergic agents (e.g., Ipratropium bromide or tiotropium); methylxanthines (theophylline, aminophyllines); cromones; anti-IgE therapy; lipoxygenase inhibitors; and leukotriene receptor antagonists or leukotriene synthesis inhibitors.

C. Efficacy of Treatment

The primary endpoint of this study was the occurrence of an exacerbation of asthma as defined by any of the following: (1) A 30% or greater reduction from baseline in morning peak expiratory flow (PEF) on two consecutive days; or (2) Six or more additional reliever puffs of albuterol or levalbuterol in a 24 hour period (compared to baseline) on 2 consecutive days; or (3) Deterioration of asthma, as determined by the Investigator, requiring: (a) systemic (oral and/or parenteral) steroid treatment, or (b) An increase in ICS≥4 times the last dose received prior to discontinuation from the study, or (c) Hospitalization.

Secondary endpoints of the study included mean changes from baseline of the following parameters: (1) Forced expiratory volume in 1 second (FEV1) in liters measured at every visit; (2) Morning and evening peak expiratory flow rate (AM PEF and PM PEF) in liters/minute measured daily; (3) Daily Albuterol/Levalbuteral use in inhalations/day; (4) Five-item Asthma Control Questionnaire (ACQ5) score at every visit; and (5) Nighttime awakenings (no. of times per night) measured daily and (6) a 22-item Sino-Nasal Outcome Test (SNOT-22), evaluated at baseline and end of treatment (at Week 12), to assess upper airway symptoms. Secondary endpoints also included proportion of patients with a composite asthma event defined by a 30% or greater reduction from baseline in morning PEF on two consecutive days together with 6 additional reliever puffs of albuterol or levalbuterol in a 24-hour period compared to baseline) on 2 consecutive days. PEF, ACQ5, asthma symptoms scores, nocturnal awakenings, and reliever medication use were captured in an electronic daily diary. Mean daily nocturnal awakenings, ranging from 0-10, were averaged from the previous 7 days. Morning and evening asthma symptom scores consisted of a non-validated patient-reported outcome assessed on a 5-point Likert-type scale, with higher scores indicating worse outcomes (Table 2). Patients recorded overall symptom scores twice a day prior to measuring PEF. Data are described as the average for the 7 days prior to the specified time point (see, e.g., FIGS. 26A and 26B).

TABLE 2

Asthma Symptom Score Assessment

A) Morning symptom score:

0 = No asthma symptoms, slept through the night
1 = Slept well, but some complaints in the morning. No nighttime awakenings
2 = Woke up once because of asthma (including early awakening)
3 = Woke up several times because of asthma (including early awakening)
4 = Bad night, awake most of the night because of asthma B) Evening symptom score:

0 = Very well, no asthma symptoms
1 = One episode of wheezing, cough, or breathlessness
2 = More than one episode of wheezing, cough, or breathlessness without interference of normal activities
3 = Wheezing, cough, or breathlessness most of the day, which interfered to some extent with normal activities
4 = Asthma very bad. Unable to carry out daily activities as usual D. Adverse Events Monitoring Safety was assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

E. Statistical Methods

For the primary analysis of proportion of patients experiencing an asthma exacerbation, a logistic regression model was used to compare the SAR group with placebo. The model included terms for treatment and stratification factor (prior ICS/LABA combination therapy dose). The primary analysis was performed based on modified intent-to-treat (mITT) population, which included all randomized patients who received at least one dose of investigational medicinal product (IMP). A stratified chi-square test was also used to corroborate the primary analysis.

For secondary efficacy endpoints, except SNOT-22, the change from baseline was analyzed using a mixed-effect model with repeated measures (MMRM) approach. The model included change from baseline values up to week 12 as response variables, and factors (fixed effects) for treatment, stratification factor, visit, treatment-by-visit interaction, baseline value, and baseline-by-visit interaction. Statistical inferences on treatment comparisons for the change from baseline at week 12 were derived from the mixed-effect model. Change from baseline in SNOT-22 was analyzed using an analysis of covariance (ANCOVA), with end of treatment measurements used to impute missing data. Pharmacodynamic effects were evaluated using MMRM models in a post hoc fashion. No adjustments were made for multiplicity, since there was only one primary endpoint and analysis. Safety variables including AEs, laboratory parameter, vital signs, ECG, clinical laboratory observations and physical examinations were summarized using descriptive statistics.

Demographic and clinical characteristics were summarized using descriptive characteristics. Plots of secondary and pharmacodynamic variables are presented as mean change from baseline over time with standard error. Comparison of treatment effects from the MMRM analyses are based on least square mean change (95% confidence intervals [CI]) from baseline at Week 12.

F. Results

Figure 25:
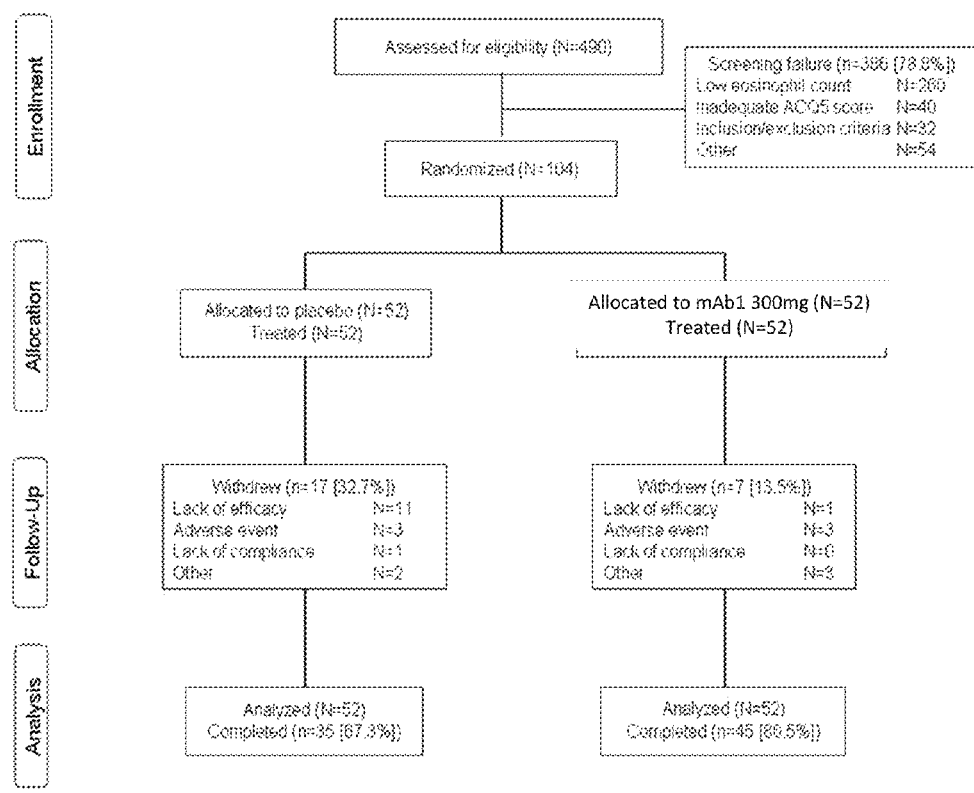
FIG. 25 is a diagram describing the patient disposition of a randomized, placebo-controlled, double-blind, parallel group study conducted with once-a-week subcutaneous administration of either 300 mg mAb1 or placebo for 12 weeks to patients with persistent moderate-to-severe eosinophilic asthma who were partially controlled/uncontrolled by inhaled corticosteroid (ICS) and long-acting beta2 agonist (LABA) therapy.

The results observed with all 104 randomized patients (from 491 screened) who either completed or discontinued the treatment phase of the study are summarized below. All randomized patients were exposed to study treatment and included in the mITT population. Baseline characteristics were similar between groups. The demographic and clinical characteristics were also similar between the two groups (Table 3). As noted above, patients were treated either with 300 mg subcutaneous mAb1 once a week, or with placebo. The study treatment period was completed by 86.5% and 67.3% of the mAb1 and placebo patients, respectively (FIG. 25). The most common cause of discontinuation was lack of efficacy, which was more frequent with placebo (21.2%) than with mAb1 (1.9%).

TABLE 3

Baseline Demographic and Clinical Characteristics of Treatment Groups.*

| Variable | Placebo (N = 52) | mAb1 300 mg (N = 52) |
|---|---|---|
| Age (yr) | 41.6 ± 13.1 | 37.8 ± 13.2 |
| Male sex, no. (%) | 26 (50.0) | 26 (50.0) |
| Race or ethnic group, no. (%) | | |
| White | 38 (73.1) | 45 (86.5) |
| Black or African American | 9 (17.3) | 5 (9.6) |
| Asian | 3 (5.8) | 1 (1.9) |
| Other | 2 (3.8) | 1 (1.9) |
| Body mass index | | |
| Mean (kg/m$^2$) | 31.6 ± 7.0 | 31.3 ± 8.0 |
| ≥30, no. (%) | 25 (48.1) | 24 (46.2) |
| Duration of asthma (yr) | 26.9 ± 14.8 | 24.2 ± 12.6 |
| Number of asthma exacerbations in prior 2 years | 1.4 ± 1.3 | 1.4 ± 1.0 |
| Prior ICS/LABA combination therapy dose, no. (%) | | |
| High Dose | 41 (78.8) | 42 (80.8) |
| Low Dose | 11 (21.2) | 10 (19.2) |
| Blood eosinophils (×10$^{-9}$/l) | 0.47 ± 0.21 | 0.55 ± 0.19 |
| FEV$_1$ (l) | 2.54 ± 0.66 | 2.47 ± 0.65 |
| FEV$_1$ (% of predicted value) | 72.0 ± 12.7 | 72.0 ± 12.6 |
| PEF (l/min) | | |
| Morning | 406.9 ± 110.7 | 393.0 ± 101.1 |
| Evening | 416.6 ± 116.8 | 414.6 ± 102.3 |
| ACQ5 score | 2.1 ± 0.5 | 2.1 ± 0.5 |
| Asthma symptom score | | |
| Morning | 0.73 ± 0.63 | 0.75 ± 0.81 |
| Evening | 1.12 ± 0.73 | 0.92 ± 0.71 |
| Nocturnal awakenings per day | 0.21 ± 0.50 | 0.44 ± 0.80 |
| SNOT-22 | 26.2 ± 15.6 | 30.9 ± 14.8 |
| Inhalations of albuterol or levalbuterol/24-hour period | 2.0 ± 1.8 | 2.2 ± 2.4 |
| FeNO (ppb) | 35.0 ± 27.1 | 37.6 ± 28.1 |
| TARC (pg/ml) | 470.5 ± 204.7 | 496.1 ± 342.4 |
| Eotaxin-3 (pg/ml) | 117.3 ± 349.2 | 75.4 ± 44.0 |
| IgE (IU/ml) | 694.7 ± 1837.8 | 657.7 ± 1482.3 |

*Plus-minus values are means ± SD, except as otherwise noted. ACQ5 denotes the Asthma Control Questionnaire (5 question version), FeNO fraction of exhaled nitric oxide, FEV$_1$ forced expiratory volume in 1 second, IgE immunoglobulin E, PEF peak expiratory volume, SNOT-22 the 22-item Sinonasal Outcome Test, and TARC thymus and activation regulated chemokine.

(i) Primary Efficacy Endpoint

The incidence of asthma exacerbations in the placebo and mAb1 treatment groups is presented in Table 4.

TABLE 4

Incidence of Asthma Exacerbations in mITT population

| | Placebo (N = 52) | mAb1 (N = 52) |
|---|---|---|
| Patients With No Asthma Exacerbations | 29 (55.8%) | 49 (94.2%) |
| Patients With Asthma Exacerbations | 23 (44.2%) | 3 (5.8%) |
| Odds Ratio vs Placebo (95% CI) | — | 0.077 (0.021, 0.279) |

There were a total of 26 asthma exacerbations during the treatment period, and no patients were hospitalized for asthma exacerbations. There were 23 patients (44.2%) who experienced an asthma exacerbation in the placebo group, whereas only 3 patients (5.8%) experienced an asthma exacerbation in the mAb1 treatment group. The odds ratio is 0.077 ($p<0.0001$) and the relative risk reduction is approximately 87%.

Out of the 26 asthma exacerbations experienced during this study, 9 were considered severe, as demonstrated by a need for immediate intervention in the form of treatment with either systemic corticosteroids or with inhaled corticosteroids at 4 or more times the dose taken prior to the event. A summary of the incidence of severe asthma exacerbations is presented in Table 5.

TABLE 5

Incidence of Severe Asthma Exacerbations in mITT population

| | Placebo (N = 52) | mAb1 (N = 52) |
|---|---|---|
| Patients With No Asthma Exacerbations | 29 (55.8%) | 49 (94.2%) |
| Patients With Severe Asthma Exacerbations | 8 (15.4%) | 1 (1.9%) |
| Patients With Non-Severe Asthma Exacerbations | 15 (28.8%) | 2 (3.8%) |

As shown in Table 5, eight severe asthma exacerbations were observed in the placebo group, and only 1 severe asthma exacerbation was observed in the mAb1 treatment group. The remaining 15 asthma exacerbations in the placebo group and 2 in the mAb1 group met the protocol definition of exacerbation based on decreased morning PEF and/or increased albuterol/levalbuterol use. As shown in Table 6, within the active treatment group, a sustained improvement versus baseline was observed during the course of the study for all parameters, despite steroid withdrawal.

TABLE 6

Exacerbation Events

| Outcome | Placebo (N = 52) | mAb1 (N = 52) |
|---|---|---|
| ≥30% reduction from baseline in morning PEF in a 24-hr period on 2 consecutive days | 10* (19.2) | 1 (1.9) |
| ≥6 additional inhalations of albuterol/levalbuterol in a 24-hr period on 2 consecutive days | 10 (19.2) | 1 (1.9) |
| Systemic steroid treatment | 5 (9.6) | 1 (1.9) |
| ≥4-fold increase in ICS from the previous dose | 3 (5.8) | 0 |
| Hospitalization | 0 | 0 |

*4 Placebo patients met both PEF and systemic steroid treatment criteria, and 1 placebo patient met both PEF and additional albuterol/levalbuterol use.

With mAb1, the time to exacerbation was longer (FIG. 1), and the risk of exacerbation was reduced relative to placebo (hazard ration 0, 10; 95% CI 0.03, 0.34; P<0.001). An analysis of the time to asthma exacerbation by Kaplan-Meier Plot revealed that the effect of treatment with mAb1 is sustained over time, including after 8 weeks when patients are at higher risk of developing exacerbations due to steroid withdrawal (FIG. 1).

Only 1 patient from the placebo group had a composite asthma event. A composite asthma event is defined as a 30% or greater reduction from baseline in morning PEF on 2 consecutive days together with ≥6 additional reliever puffs of albuterol or levalbuterol in a 24-hour period (compared to baseline) on 2 consecutive days.

(ii) Other Efficacy Endpoints

Lung function parameters (FEV1, AM PEF and PM PEF), asthma symptom-based endpoints (ACQ score, nighttime awakenings), and albuterol use were assessed for each patient at each visit. Results observed for these parameters (weekly change from baseline) are depicted in FIGS. 2-7, respectively. In addition, the SNOT-22 score was assessed at baseline and at the end of treatment. For all parameters, the baseline and Week 12 (LOCF) mean values along with the mean difference between treatment groups (ANOVA model for SNOT-22) are summarized in Table 7. In Table 7, the column labeled "Difference vs. Placebo" reflects the placebo-corrected value from baseline that takes into account changes that are observed in the value of the parameter as compared to the changes that were observed for that parameter in the placebo-treated group.

TABLE 7

Secondary Parameters of Lung Function and Symptom Scores

| | N | Baseline Mean (SD) | Least-Squared Mean Change (SD) | Difference vs. Placebo | p value |
|---|---|---|---|---|---|
| FEV1 (L) | | | | | |
| Placebo | 52 | 2.54 (0.66) | −0.22 (0.06) | — | |
| mAb1 | 52 | 2.47 (0.65) | 0.05 (0.06) | 0.27 (0.11, 0.42) | 0.0009 |
| AM PEF (L/min) | | | | | |
| Placebo | 52 | 406.9 (110.7) | −20.7 (9.1) | — | |
| mAb1 | 51 | 393.0 (101.1) | 13.9 (8.8)† | 34.6 (10.6, 58.5) | 0.0051 |
| PM PEF (L/min) | | | | | |
| Placebo | 51 | 416.6 (116.8) | −18.4 (8.9)† | — | |
| mAb1 | 52 | 414.6 (102.3) | 4.3 (8.5) | 22.7 (−0.7, 46.0) | 0.0567 |
| Albuterol Use (Puffs/Day) | | | | | |
| Placebo | 52 | 2.0 (1.8) | 0.7 (0.3) | — | |
| mAb1 | 50 | 2.2 (2.4) | −1.3 (0.3)‡ | −2.0 (−2.9, −1.2) | <0.0001 |
| ACQ Score | | | | | |
| Placebo | 52 | 2.08 (0.52) | −0.27 (0.16) | — | |
| mAb1 | 52 | 2.09 (0.46) | −1.00 (0.16) | −0.73 (−1.15, −0.30) | 0.0011 |
| Night-time Awakenings (No. of times/night) | | | | | |
| Placebo | 52 | 0.2 (0.5) | 0.1 (0.1) | — | |
| mAb1 | 52 | 0.4 (0.8) | −0.2 (0.1) | −0.2 (−0.5, −0.0) | 0.0518 |
| SNOT22 Average Score | | | | | |
| Placebo | 51 | 26.24 (15.62) | 0.23 (2.15)† | — | |
| mAb1 | 50 | 30.92 (14.77) | −8.26 (2.20)‡ | −8.49 (−13.96, −3.03) | 0.0027 |

†51 patients with at least 1 post-baseline assessment.
‡50 patients with at least 1 post-baseline assessment.

Figure 3:
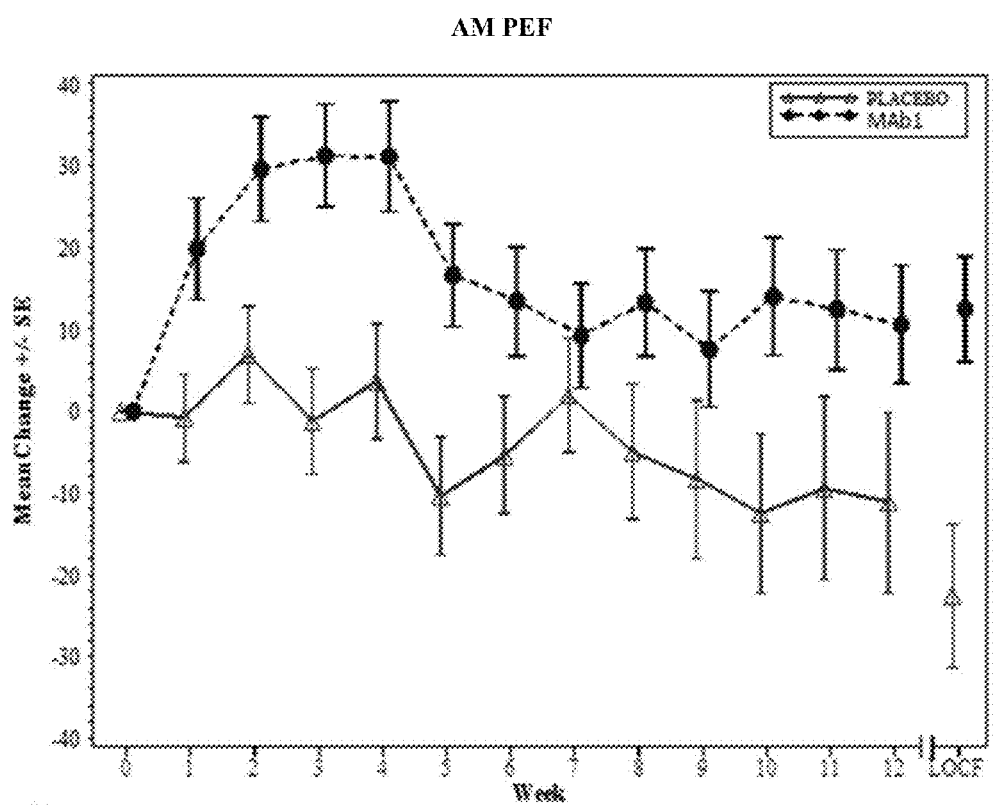
FIG. 3 is a graph that shows the mean change from baseline in morning peak expiratory flow rate (AM PEF) in liters per minute in patients treated with placebo (open triangles) as compared to patients treated with anti-IL-4R antibody mAb1 (closed circles).
Figure 4:
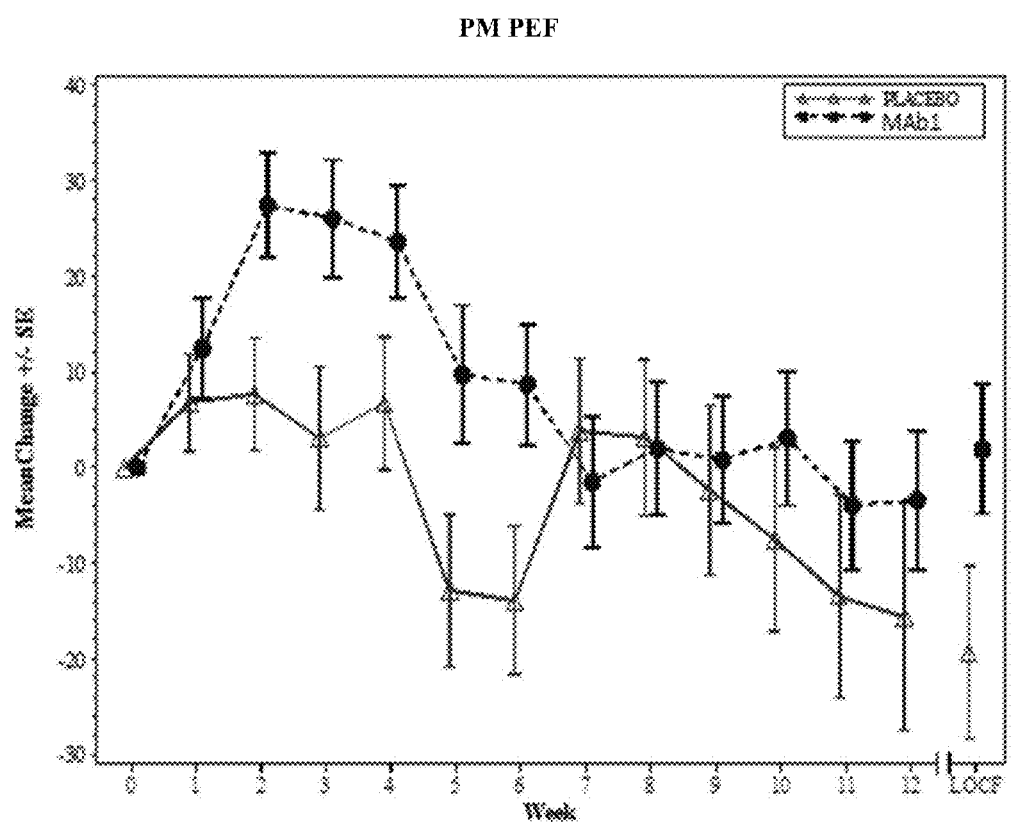
FIG. 4 is a graph that shows the mean change from baseline in evening peak expiratory flow rate (PM PEF) in liters per minute in patients treated with placebo (open triangles) as compared to patients treated with anti-IL-4R antibody mAb1 (closed circles).
Figure 5:
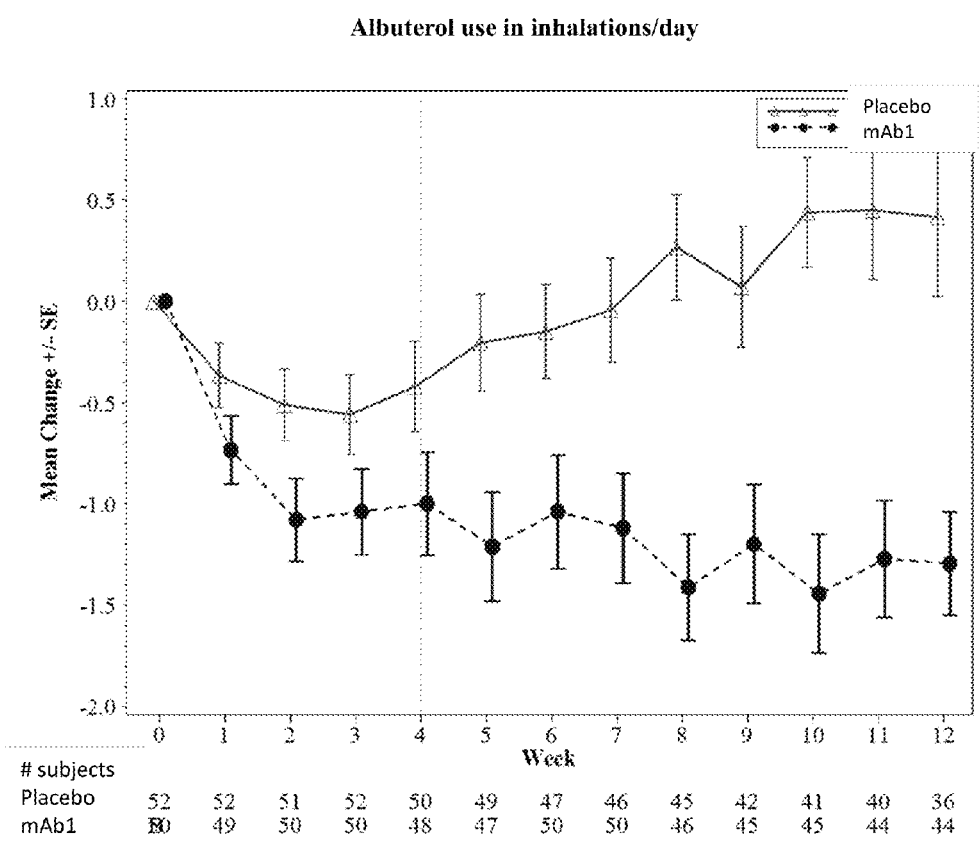
FIG. 5 is a graph that shows the mean change from baseline in albuterol use in inhalations per day in patients treated with placebo (open triangles) as compared to patients treated with anti-IL-4R antibody mAb1 (closed circles). Broken vertical lines indicate withdrawal of LABA.

Treatment with mAb1 resulted in a significant change from baseline in FEV1 at Week 1, which was maintained through Week 12 (FIG. 2) despite LABA and ICS withdrawal, with a small decrease in FEV1 at Week 5 coinciding with LABA withdrawal. Similar improvements were observed in morning PEF, but less so in evening PEF (FIGS. 3 and 4). The least-squared (LS) mean change from baseline to week 12 in FEV1 was −0.22 L for placebo and 0.05 L for the mAb1 group. (p=0.0009).

Figure 6:
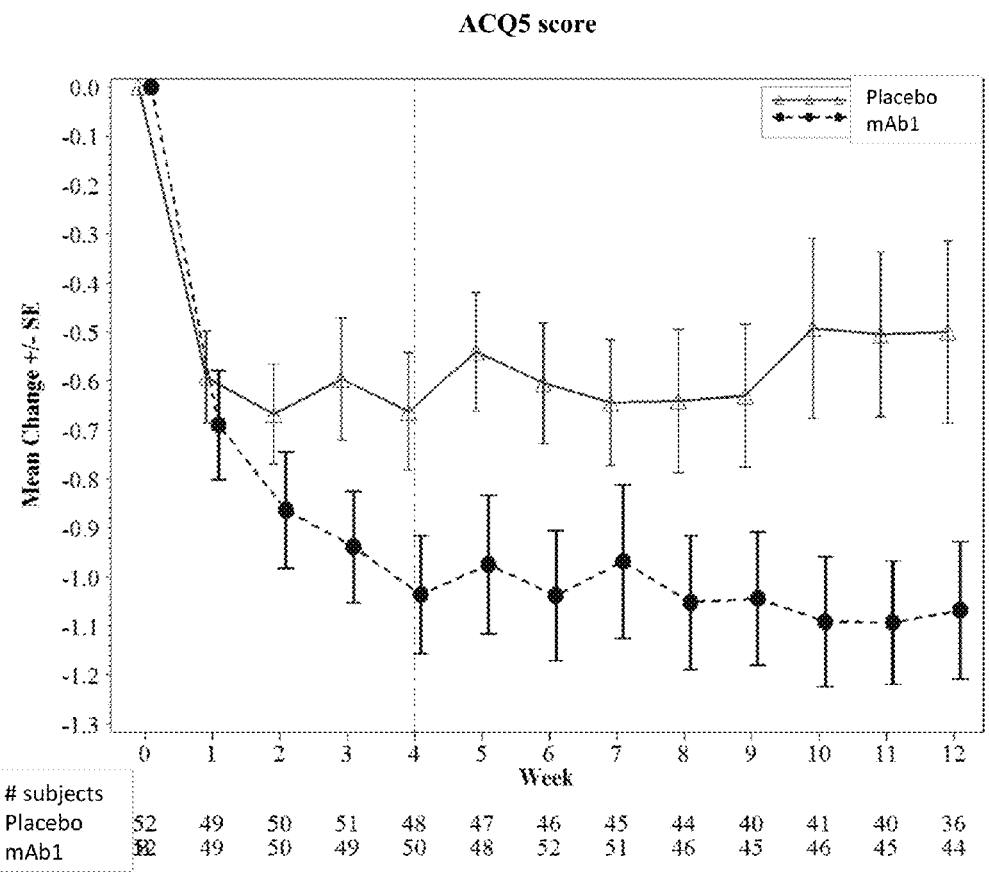
FIG. 6 is a graph that shows the mean change from baseline in five-item asthma control questionnaire (ACQ5) score in patients treated with placebo (open triangles) as compared to patients treated with anti-IL-4R antibody mAb1 (closed circles). Broken vertical lines indicate withdrawal of LABA.

ACQ5 score improved in both treatment groups at Week 1 (FIG. 6). However, while ACQ5 improved further with mAb1 between Weeks 1 and 4, the placebo effect stabilized, maintaining the difference through Week 12.

Figure 26A:
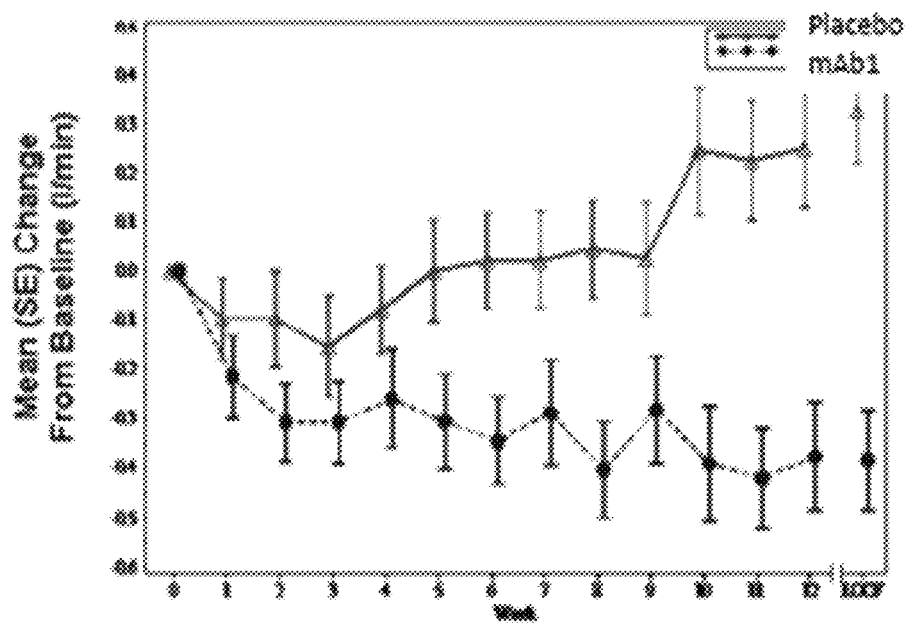
FIGS. 26A and 26B are scatter plots of morning (A) and evening (B) asthma symptoms measured over 12 weeks following administration of placebo (open triangles) or mAb1 (closed circles).
Figure 26B:
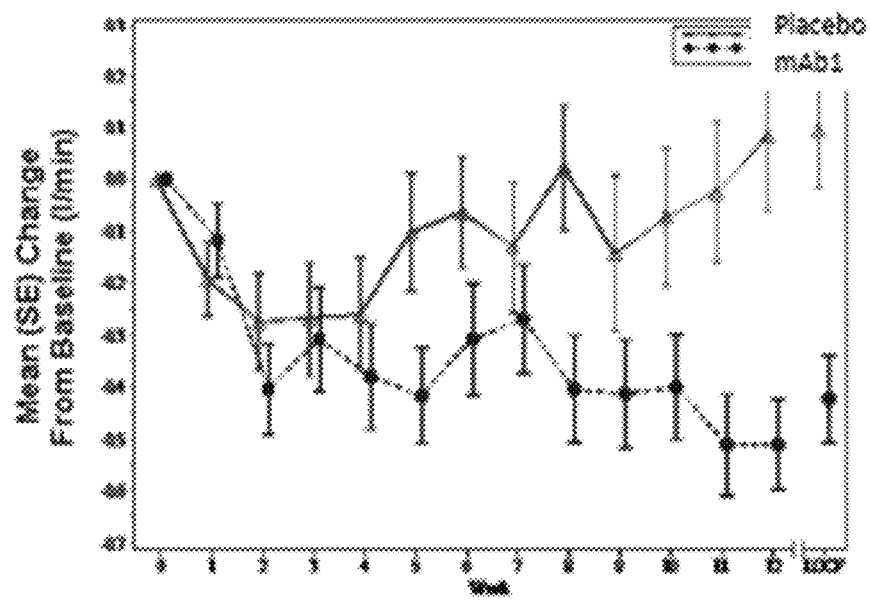

Morning symptom scores increased from baseline to Week 12 with placebo. With mAb1, there was an initial decrease that remained below baseline through Week 12 (FIG. 26A). A similar pattern (with greater variability) was observed for evening asthma symptom scores (FIG. 26B).

Figure 7:
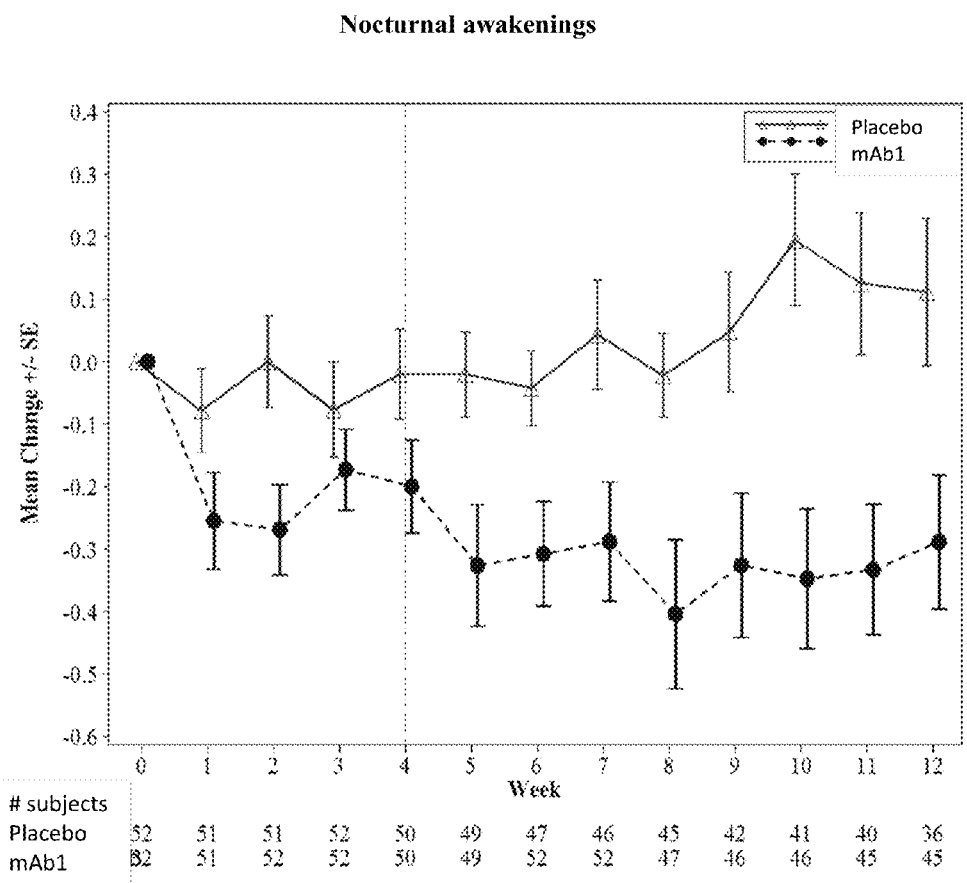
FIG. 7 is a graph that shows the mean change from baseline in nocturnal awakenings in number of times per night in patients treated with placebo (open triangles) as compared to patients treated with anti-IL-4R antibody mAb1 (closed circles). Broken vertical lines indicate withdrawal of LABA.

Nocturnal awakenings were stable from the placebo group through Week 6, then increased from Weeks 6 to 12. In contrast, nocturnal awakenings decreased in the mAb1 group by Week 1 and remained improved versus baseline through Week 12 (FIG. 7).

Changes in albuterol/levalbuterol use (FIG. 5) were similar to other secondary endpoints: an initial decrease followed by a return towards baseline with placebo. With mAb1, the initial decrease was maintained over time.

There was a non-significant difference at baseline between the SNOT-22 values, with the mean placebo score at 26.24 and the mean mAb1 score at 39.02. At week 12, the LS mean change was a slight increase of 0.23 points for the placebo group and a mean decrease (improvement) of 8.26 points for the mAb1 group. This represented a magnitude of improvement of 8.49 points for the mAb1 group (p=0.0027).

TABLE 8

Secondary Endpoints

| Outcome | Placebo (N = 52) | mAb1 (N = 52) | Difference vs Placebo (95% CI)** | P Value |
|---|---|---|---|---|
| Kaplan-Meier estimate at 12 weeks | 46.0 (31.8, 60.2) | 5.8 (0.0, 2.1) | 0.10 (0.03 to 0.34) | <0.001 |
| Change in morning asthma symptom scores, baseline to week 12 | 0.3 ± 0.1 | −0.4 ± 0.1 | −0.7 (−0.9 to −0.4) | <0.001 |
| Change in evening asthma symptom scores, baseline to week 12 | 0.1 ± 0.1 | −0.6 ± 0.1 | −0.7 (−0.9 to −0.4) | <0.001 |

TABLE 9

Change From Baseline at Week 12 in SNOT-22 Items Relevant to Upper Airway Disease.

| | Least-Squares Mean Change ± Standard Error | | | |
|---|---|---|---|---|
| SNOT-22 Subscale | Placebo (N = 52) | mAb1 (N = 52) | Difference vs Placebo (95% CI) | P Value |
| Need to blow nose | −0.25 ± 0.17* | 0.95 ± 0.17† | −0.70 (−1.13, −0.26) | 0.002 |
| Nasal blockage | −0.20 ± 0.19* | −0.94 ± 0.19† | 0.75 (−1.22, −0.28) | 0.002 |
| Decreased sense of smell/taste | 0.04 ± 0.18* | −1.13 ± 0.18† | −1.16 (−1.62, −0.71) | <0.001 |

*51 and †50 patients with at least 1 post-baseline assessment respectively

For all secondary endpoints, Week 12 measurements favored mAb1 treatment and were significant, except for evening PEF and nocturnal awakenings (Table 7 and 8). Significant improvements with mAb1 were also observed for the three SNOT-22 items relevant to upper airway disease (Table 9)

(iii) Safety mAb1 was generally safe and well tolerated. Treatment-emergent adverse events (TEAEs) were reported similarly by 40 (76.9%) placebo-treated patients and by 42 (80.8%) mAb1-treated patients (Table 10). TEAEs were non-specific, generally mild to moderate in intensity, and the majority recovered by the end of the study. An increased reporting of the following TEAEs was observed for mAb1 in comparison with placebo: injection site reactions were reported by 15 (28.8%) mAb1 patients and by 5 (9.6%) placebo patients; nasopharyngitis was reported by 7 (13.5%) mAb1 patients and 2 (3.8%) placebo patients; headache was reported by 6 (11.5%) mAb1 patients and 3 (5.85) placebo patients and nausea was reported by 4 (7.7%) mAb1 patients and 1 (1.9%) placebo patients.

TABLE 10

Adverse Events.

| Adverse event | Placebo (N = 52) no. of patients (%) | mAb1 300 mg (N = 52) no. of patients (%) |
| --- | --- | --- |
| Any adverse event | 40 (76.9) | 42 (80.8) |
| Any serious adverse event | 3 (5.8) | 1 (1.9) |
| Study discontinuation owing to adverse event | 3 (5.8) | 3 (5.8) |
| Death | 0 | 0 |
| Most common AEs* | | |
| Injection site reactions† | 5 (9.6) | 15 (28.8) |
| Nasopharyngitis | 2 (3.8) | 7 (13.5) |
| Upper respiratory tract infection | 9 (17.3) | 7 (13.5) |
| Headache | 3 (5.8) | 6 (11.5) |
| Nausea | 1 (1.9) | 4 (7.7) |
| Arthropod bite | 0 | 3 (5.8) |
| Muscle spasms | 0 | 3 (5.8) |
| Nasal congestion | 1 (1.9) | 3 (5.8) |
| Rash | 1 (1.9) | 3 (5.8) |
| Urticaria | 0 | 3 (5.8) |
| Viral upper respiratory tract infection | 0 | 3 (5.8) |

*≥3 patients in any treatment group by Preferred Term
†Injection site reaction includes events reported as: injection site pain, injection site reaction, injection site erythema, injection site rash, injection site haematoma, injection site urticaria, injection site dermatitis, injection sites inflammation, injection site nodule, injection site pruritus and injection site swelling.

There were no deaths reported during the study period. Of the 4 treatment emergent serious adverse events (SAEs) reported: 1 mAb1 patient experienced bipolar disorder and 3 placebo patients experienced SAEs of asthma with pneumonia, gunshot wound with left pneumothorax, and right ankle fracture. None of these SAEs were considered as related to the IMP and all but the recent ankle fracture were recovered by the end of the study. There were no deaths.

A total of 6 patients discontinued the study due to a TEAE: 3 patients in the mAb1 group (bipolar disorder, asthma with wheezing, and angioedema) and 3 patients in the placebo group (upper respiratory tract infection, psoriasis and asthma). The TEAE of angioedema occurred in a 42-year old African-American female after the ninth study treatment dose as a pruritic, popular rash observed at, and distant to, the injection site. It persisted for one week, resolved after study treatment discontinuation, and prednisome and diphenhydramine treatment. It was deemed treatment-related. This AE was subsequent to milder rashes at the injection site after the first and sixth study treatment doses.

Among the most common AEs occurring in ≥3 patients in any treatment group (Table 10), injection site reactions, nasopharyngitis, nausea, and headache occurred more frequently with mAb1 than placebo. No clinically significant changes in vital signs, physical examination, clinical laboratory or ECG findings were reported in either group.

G. Conclusion

Significant improvements were observed for lung function and other asthma control parameters. Efficacy was observed early and sustained despite background therapy withdrawal. A relative reduction of approximately 87% (p<0.0001) in the primary endpoint of the incidence of asthma exacerbations in persistent, moderate-to-severe asthma patients with eosinophilia was observed after 12-week treatment with 300 mg of mAb1 once weekly (5.8%) compared with placebo (44.2%). As shown in Table 7, clinically meaningful and statistically significant (without multiplicity adjustment) improvements with treatment compared with placebo were observed in lung function parameters (FEV1, PEF AM), asthma symptom scores (ACQ) and albuterol use. Positive trends were observed for PEF PM (p=0.0567) and nocturnal awakenings (p=0.0518). A statistically significant (without multiplicity adjustment) improvement was also observed for the SNOT-22 score. Within the active treatment group, a sustained improvement versus baseline was observed during the course of study for all parameters, despite LABA and ICS withdrawal. mAb1 was generally safe and well tolerated.

Example 3

Biomarker Studies

Biomarker analysis was conducted on samples taken from subjects who participated in clinical trials of mAb1 (see Example 2 above). In particular, serum/plasma biomarkers associated with TH2 inflammation, such as thymus and activation chemokine (TARC; CCL17), Immunoglobulin E (IgE), eotaxin-3, periostin, carcinoembryonic antigen (CEA), YKL-40 and blood eosinophils were measured in samples from patients at baseline and at different time points following initiation of study treatment(s). Baseline levels of these biomarkers were assessed for potential predictive value for treatment response. In addition, the fraction of exhaled NO (FeNO) and induced sputum eosinophils and neutrophils were measured as biomarkers of bronchial inflammation. Exhaled nitric oxide assessment was conducted prior to spirometry and following a fast of at least 1 hour using a NIOX instrument (Aerocrine AB, Solna, Sweden). Biomarkers were analyzed using a mixed model and the least square mean derived from the model are reported below.

Asthma subjects (N=104) were administered either mAb1 (300 mg) or placebo subcutaneously, on days 1, 8, 15, 22, 29, 36, 43, 50, 57, 64, 71, and 78 of the study (i.e., 12 weekly doses) (see Example 2 herein). Samples for biomarker analysis were collected from the antibody- and placebo-treated subjects at week 0, 1, 4, 8 and 12. Antigen-specific IgE was detected using the Phadiatop® test.

Figure 8:
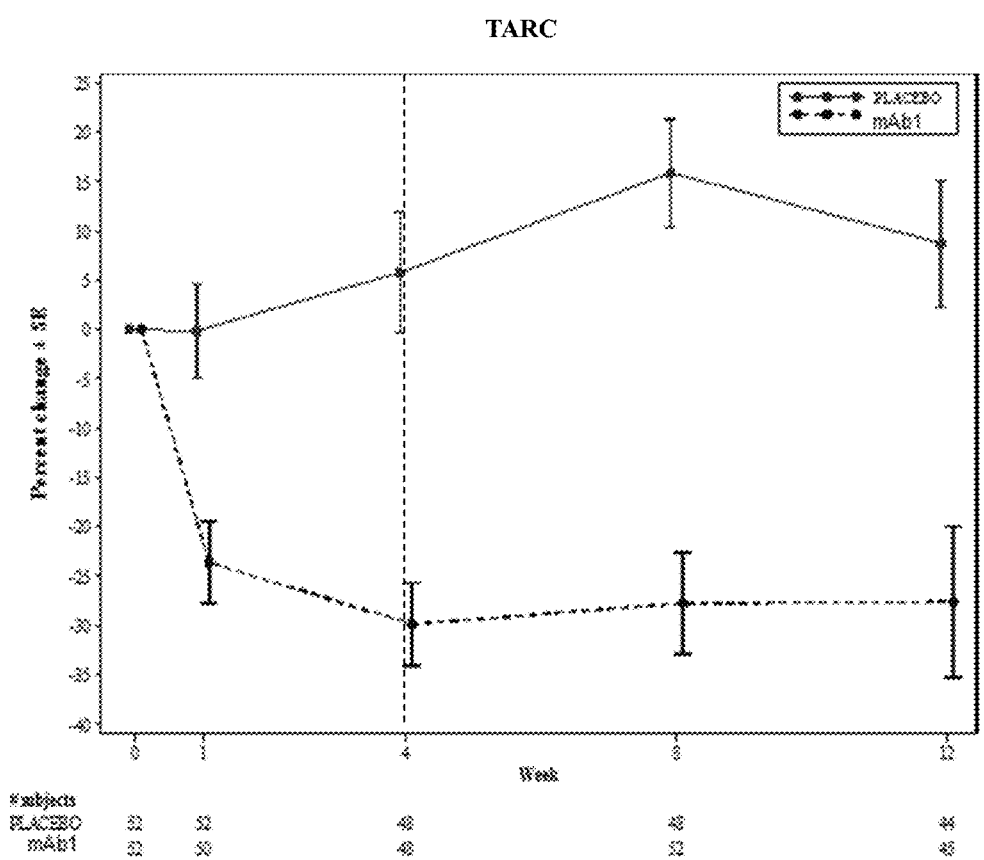
FIG. 8 is a graph that shows the mean percentage change from baseline in TARC by visit at week 0, 1, 4, 8, and 12 of the mITT population treated with placebo (closed circles) as compared to patients treated with anti-IL-4R antibody mAb1 (closed squares). Broken vertical lines indicate withdrawal of LABA.
Figure 9:
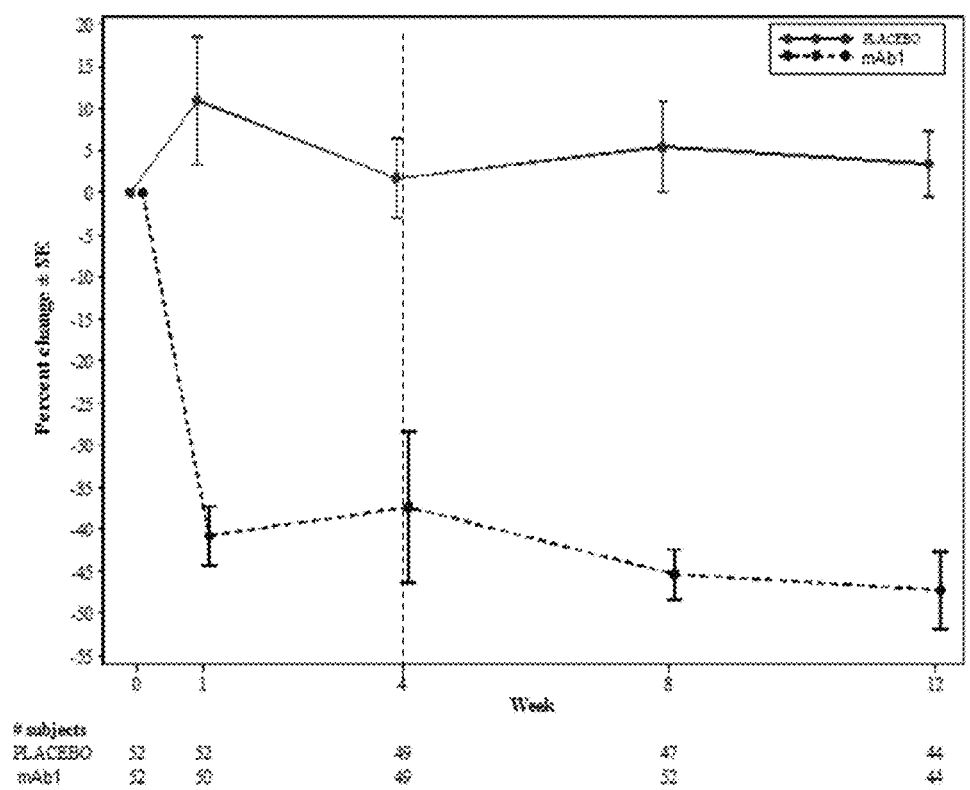
FIG. 9 is a graph that shows the mean percentage change from baseline in Eotaxin-3 by visit at week 0, 1, 4, 8, and 12 of the mITT population treated with placebo (closed circles) as compared to patients treated with anti-IL-4R antibody mAb1 (closed squares). Broken vertical lines indicate withdrawal of LABA.
Figure 10:
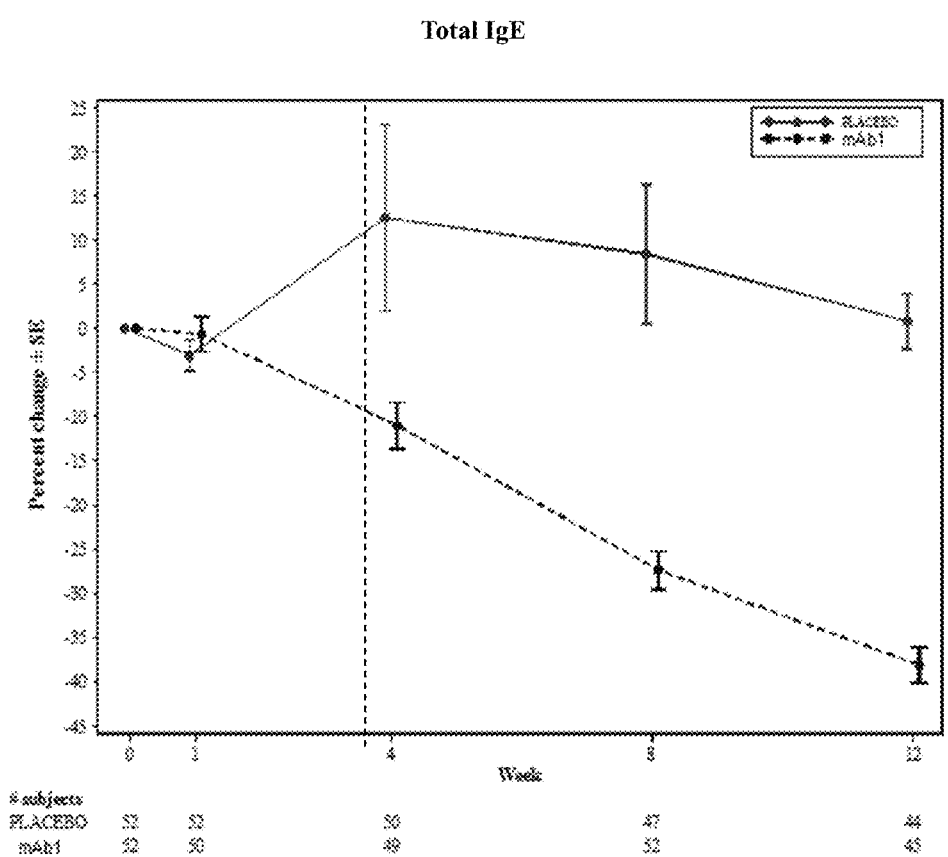
FIG. 10 is a graph that shows the mean percentage change from baseline in total IgE by visit at week 0, 1, 4, 8, and 12 in the mITT population treated with placebo (closed circles) as compared to patients treated with anti-IL-4R antibody mAb1 (closed squares). Broken vertical lines indicate withdrawal of LABA.

TARC, eotaxin-3, and IgE remained unchanged in response to placebo (FIGS. 8, 9 and 10). In contrast, a rapid reduction in TARC (mean % change−22.7% vs+0.3%; p=0.0003) (FIG. 8) and eotaxin-3 (mean % change−39.62% vs 12.69%; p<0.0001) (FIG. 9) was observed within one week in patients treated with mAb1 and persisted until week 12: TARC: −26.0% vs+7.6% placebo (p=0.0005); Eotaxin-3: −45.67% vs+5.13% placebo (p<0.0001).

TARC levels responded within a week following exposure to mAb1 at 300 mg administered subcutaneously. TARC levels plateau at approximately 50% of the baseline level in mAb1-treated subjects, regardless of ICS withdrawal. The data suggest that TARC expression is more directly linked to IL-4R signaling, than FEV1 changes (which drop in parallel to ICS withdrawal [after Week 4]) and that IL-4R blockage induces a shift towards a TH1 signature, as observed with, for example, IFNgamma administration. It might be possible to titrate the mAb1 dose using TARC (and for example CXCL10) in particular in patients requiring long term treatment and at risk for TH1 type immune diseases.

Total serum IgE also decreased following mAb1 treatment. Total serum IgE response was more heterogenous and delayed compared to TARC response. Mean (SD) baseline IgE levels were 694.68 IU/L (1837.82) for the placebo group (n=52) and 657.66 (1482.25) for the mAb1 group (n=52), whereas the median was 169.95 for the placebo group and 206.15 for the mAb1 group. Despite this heterogeneity, a trend towards IgE decrease in mAb1-exposed patients compared with placebo was observed—however, starting at week 4 only. Serum IgE was significantly reduced in the mAb1 group compared with placebo (mean % change, −10.1% vs+13.5%; p=0.0325) starting from week 4 and continued to decrease until week 12 (mean % change, −36.8% for REGN668/SAR231893 vs −5.5% for placebo; p<0.0001) (FIG. 10).

Changes from baseline and placebo at Week 12 for FeNO, TARC, eotaxin-3, and IgE all favored mAb1 (all P<0.001) (Table 11). No differences from baseline or between treatments were observed in YKL-40 or CEA.

TABLE 11

Percent Change From Baseline at Week 12 in Pharmacodynamic Endpoints.

| Outcome | Least-Squares Mean Percent Change ± Standard Error | | P Value |
| --- | --- | --- | --- |
| | Placebo (N = 52) | mAb1 (N = 52) | |
| FeNO | 35.0 ± 10.8 | 28.7 ± 11.2 | <0.001 |
| TARC | 7.6 ± 6.9 | −26.0 ± 6.9 | <0.001 |
| Eotaxin-3 | 5.1 ± 4.7 | −45.7 ± 4.7 | <0.001 |
| IgE | 5.5 ± 3.6 | −36.8 ± 3.6 | <0.001 |
| Blood eosinophils | 2.7 ± 15.8 | 41.6 ± 15.7 | 0.078 |

Figure 11:
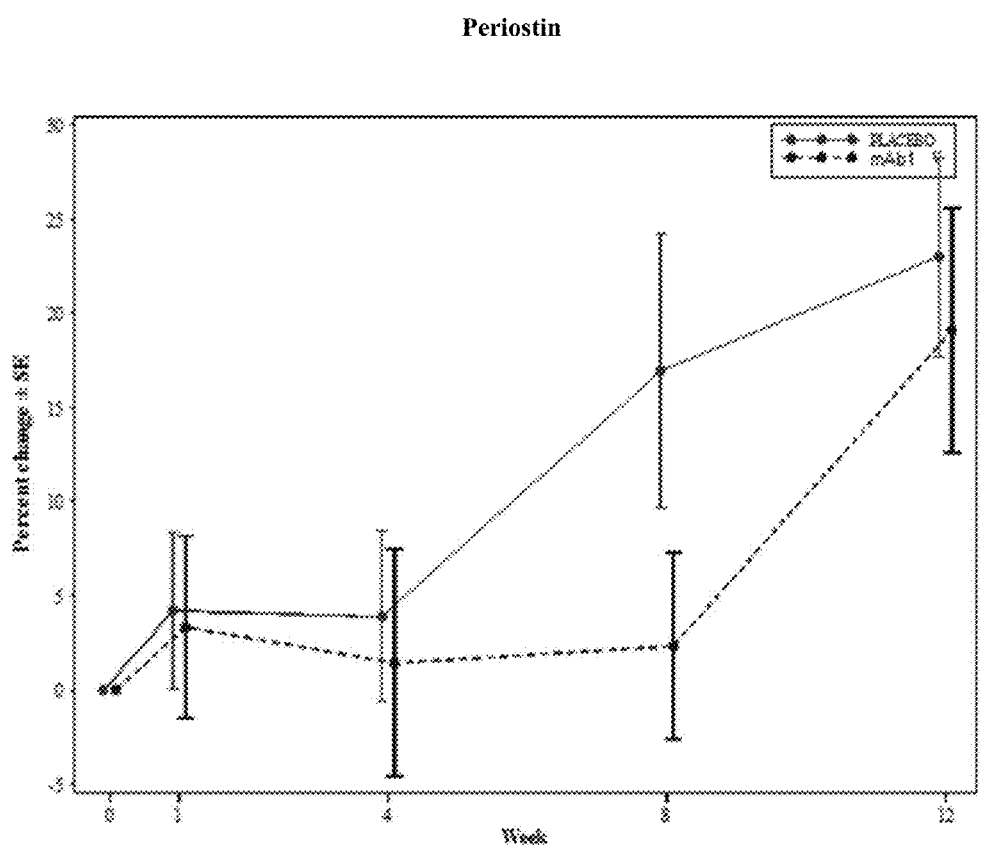
FIG. 11 is a graph that shows the mean percentage change from baseline in periostin by visit at week 0, 1, 4, 8, and 12 in the mITT population treated with placebo (closed circles) as compared to patients treated with anti-IL-4R antibody mAb1 (closed squares).
Figure 12:
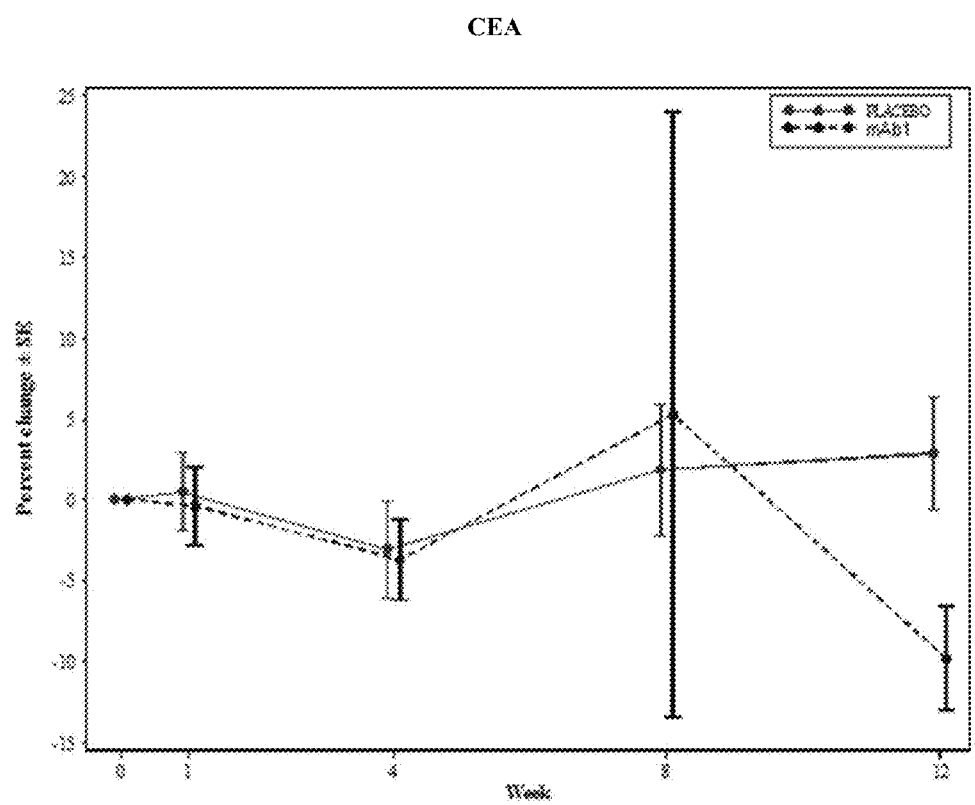
FIG. 12 is a graph that shows the mean percentage change from baseline in carcinoembryogenic antigen (CEA) by visit at week 0, 1, 4, 8, and 12 in the mITT population treated with placebo (closed circles) as compared to patients treated with anti-IL-4R antibody mAb1 (closed squares).
Figure 13:
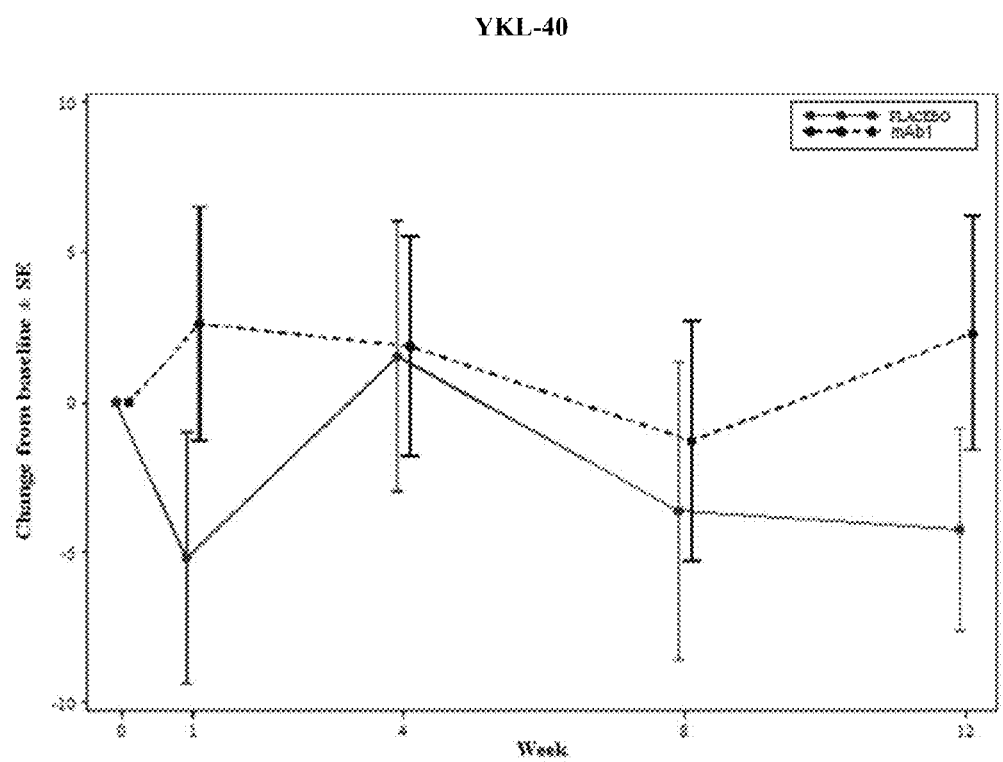
FIG. 13 is a graph that shows the mean percentage change from baseline in YKL-40 by visit at week 0, 1, 4, 8, and 12 in the mITT population treated with placebo (closed circles) as compared to patients treated with anti-IL-4R antibody mAb1 (closed squares).
Figure 14:
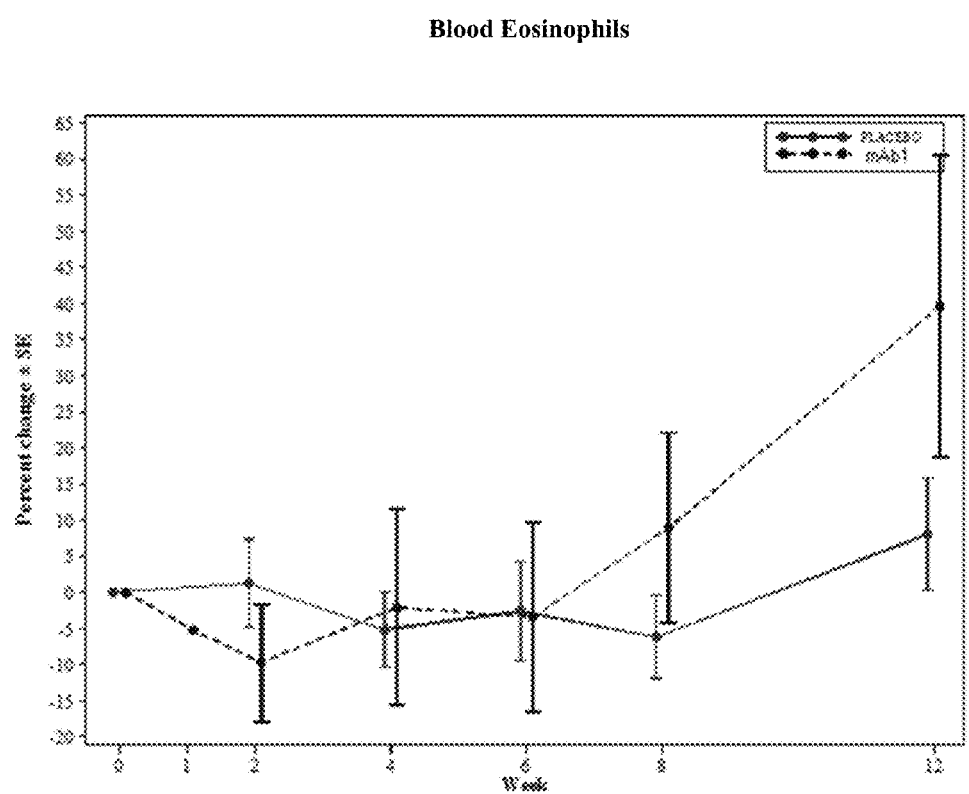
FIG. 14 is a graph that shows the mean percentage change from baseline in blood eosinophils by visit at week 0, 1, 2, 4, 6, 8, and 12 in the mITT population treated with placebo (closed circles) as compared to patients treated with anti-IL-4R antibody mAb1 (closed squares).

There was a transient decrease in periostin levels, followed by an increase with LABA/ICS withdrawal (FIG. 11). Administration of mAb1 delayed the increase, but did not prevent the increase above baseline. No consistent treatment effect was observed with CEA (FIG. 12) and YKL-40 (FIG. 13). The number of blood eosinophils remained unchanged through Week 6, but then increased at Weeks 8 and 12 (FIG. 14). Peripheral blood eosinophil numbers were unchanged on placebo throughout treatment. The difference between the treatments was not significant, with the borderline increase driven by larger blood eosinophil elevations in only a few patients treated with mAb1. Little or no increases were observed in the majority of patients (Table 12).

TABLE 12

Proportions of Patients Achieving Thresholds of Change in Blood Eosinophil Levels.

| | Number (%) of patients | |
| --- | --- | --- |
| Change in eosinophils | Placebo (n = 52) | mAb1 (n = 52) |
| >15% Decrease | 13 (30.2) | 21 (47.7) |
| 15% Decrease-0% change | 7 (16.3) | 6 (13.6) |
| 0%-15% Increase | 8 (18.6) | 4 (9.1) |
| 15%-100% Increase | 13 (30.2) | 6 (13.6) |
| 100%-200% increase | 2 (4.7) | 3 (6.8) |
| >200% increase | 0 | 4 (9.1) |

Figure 15:
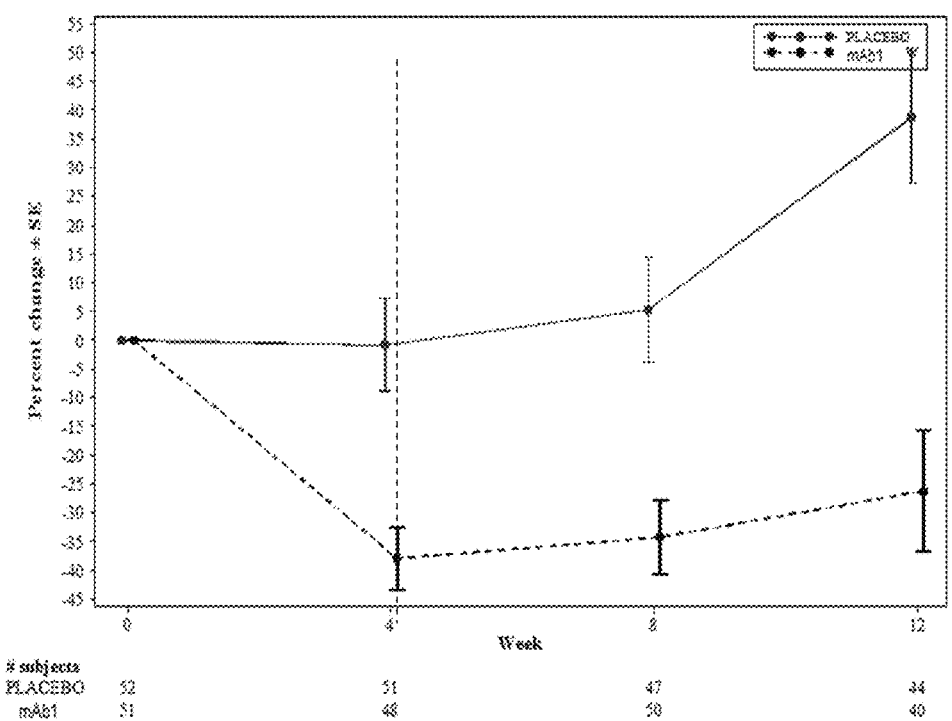
FIG. 15 is a graph that shows the mean percent change in fractional exhaled nitric oxide (NO) level from baseline by visit at week 0, 4, 8, and 12 in the mITT population treated with placebo (closed circles) as compared to patients treated with anti-IL-4R antibody mAb1 (closed squares). Broken vertical lines indicate withdrawal of LABA.

Because only 3 mAb1 patients experienced asthma exacerbation during the study, no conclusion could be drawn regarding the association between baseline biomarker levels and asthma exacerbations.

mAb1 treatment was also associated with a significant decrease from baseline in FeNO at Week 4, and FeNo remained below baseline through Week 12, regardless of ICS withdrawal (mean % change at week 12: −28.7 for mAb1 vs 35.0 for placebo; p<0.0001) (FIG. 15). In contrast, placebo FeNo values remained stable through Week 8, followed by an increase at Week 12 coincident with ICS withdrawal.

Figure 16:
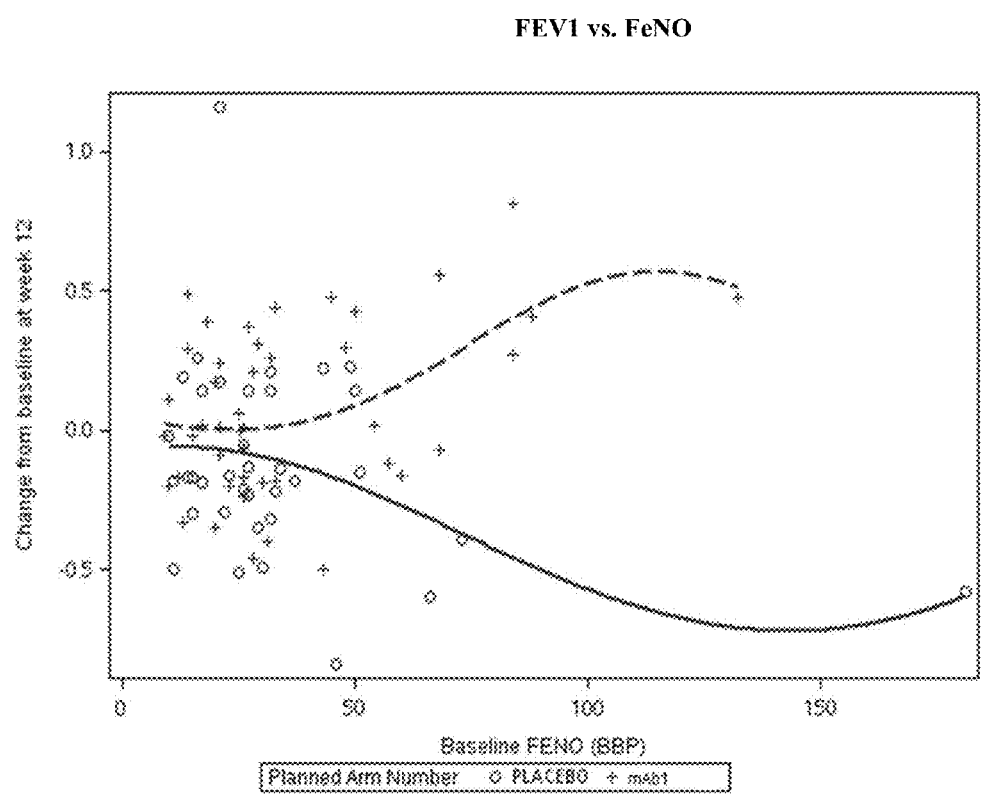
FIG. 16 is a scatter plot of the change in FEV1 (L) from baseline at week 12 versus baseline fraction of exhaled nitric oxide (FeNO) (PPB) in the mITT population treated with placebo (open circles and full line) as compared to patients treated with anti-IL-4R antibody mAb1 (plus sign and dashed line).
Figure 17:
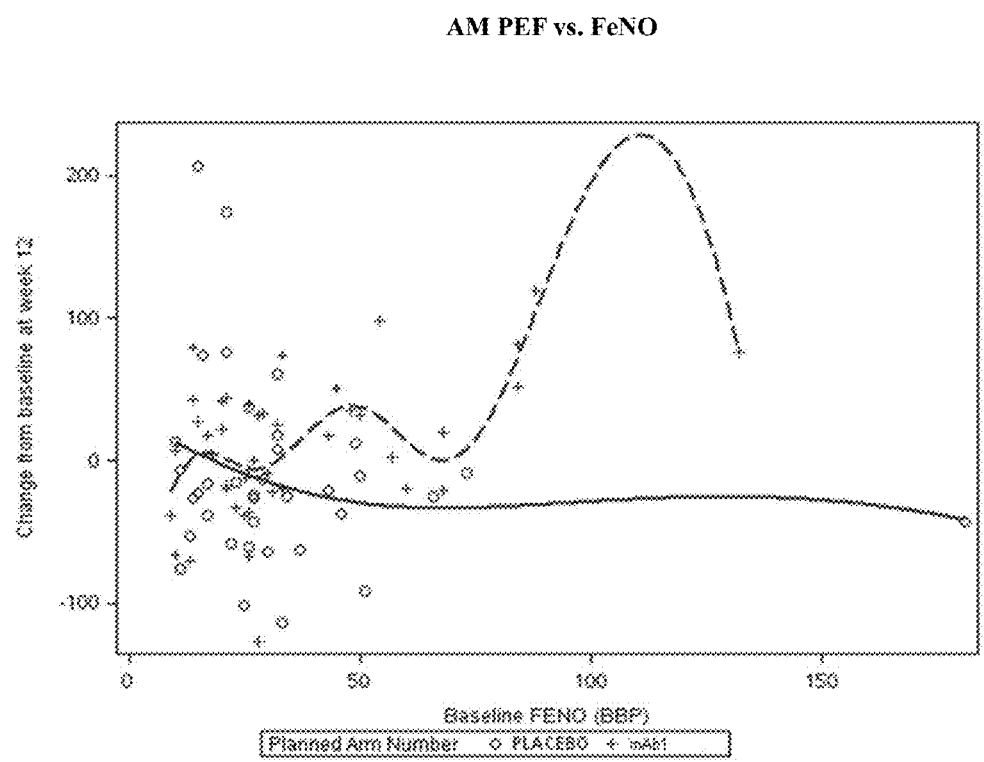
FIG. 17 is a scatter plot of the change in AM-PEF (L/min) from baseline at week 12 versus baseline FeNO (PPB) in the mITT population treated with placebo (open circles and full line) as compared to patients treated with anti-IL-4R antibody mAb1 (plus sign and dashed line).
Figure 18:
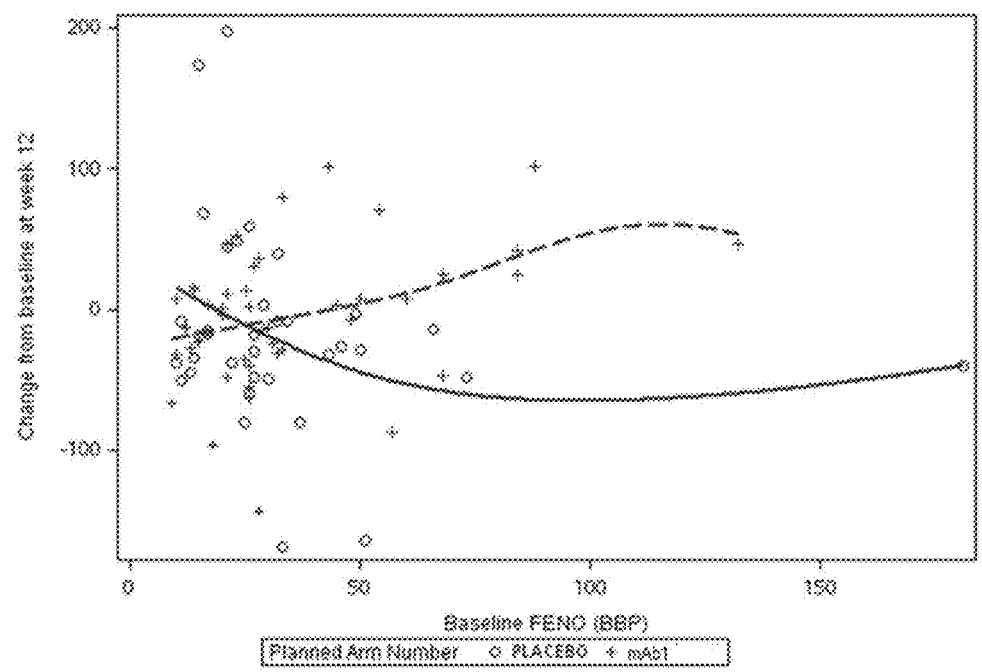
FIG. 18 is a scatter plot of the change in PM-PEF (L/min) from baseline at week 12 versus baseline FeNO (PPB) in the mITT population treated with placebo (open circles and full line) as compared to patients treated with anti-IL-4R antibody mAb1 (plus sign and dashed line).

Forced expiratory volume in 1 second ($FEV_1$) improvement significantly correlated with FeNO reduction (r=−0.408, p=0.009) at week 12 (FIG. 16). Similarly, improvements in AM-PEF and PM-PEF correlated with FeNO reduction (FIGS. 17 and 18). Other correlations with FeNO were not significant. See Table 13.

TABLE 13

Correlation between $FEV_1$ and PD Endpoints.

| Outcome | Correlation | P Value |
| --- | --- | --- |
| FeNO | −0.408 | <0.009 |
| TARC | −0.248 | 0.10 |
| Eotaxin-3 | −0.146 | 0.34 |
| IgE | −0.279 | 0.06 |
| Blood eosinophils | 0.165 | 0.28 |

Figure 19:
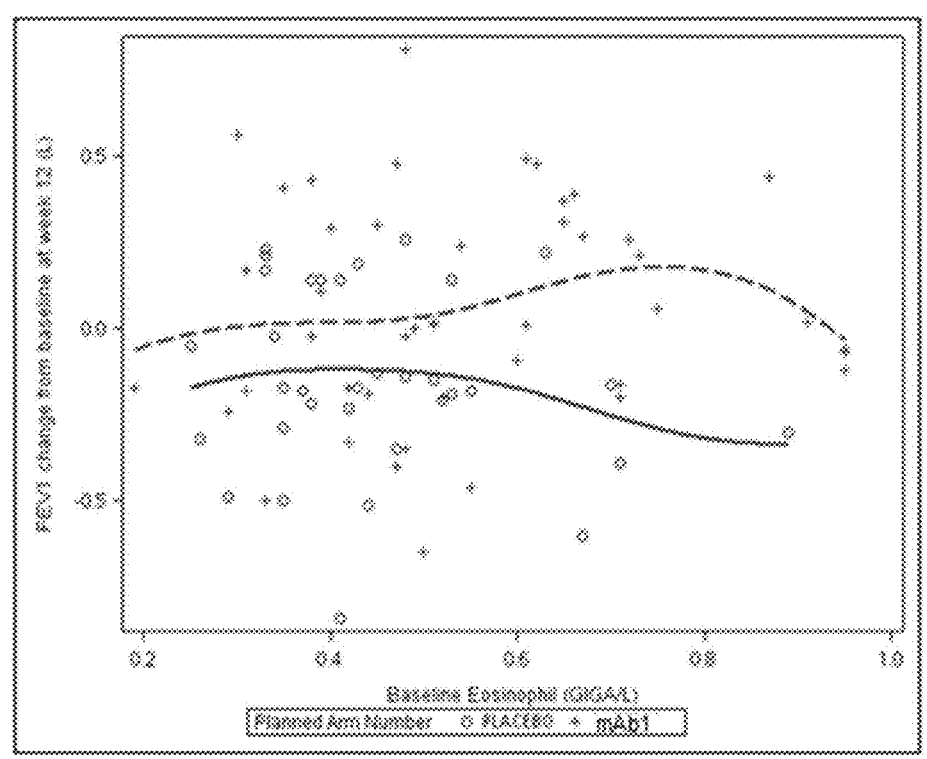
FIG. 19 is a scatter plot of the change in FEV1 from baseline at week 12 (L) versus blood eosinophils count (GIGA/L) in the mITT population treated with placebo (open circles and full line) as compared to patients treated with anti-IL-4R antibody mAb1 (plus sign and dashed line).
Figure 20:
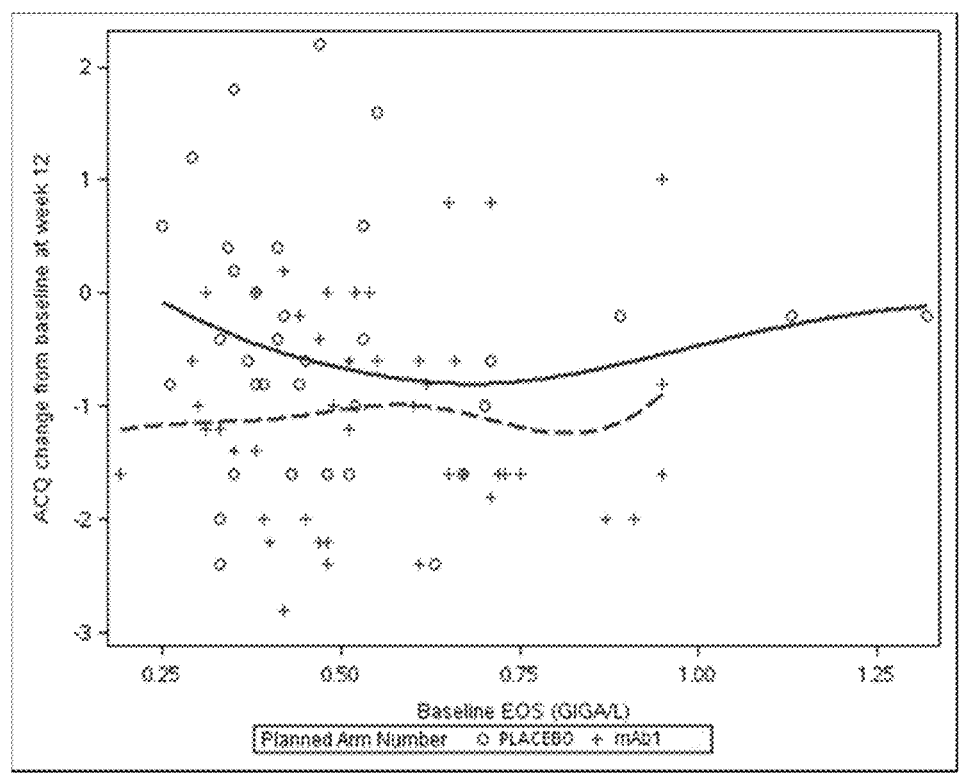
FIG. 20 is a scatter plot of the change in ACQ from baseline at week 12 versus blood eosinophils count (GIGA/L) in the mITT population treated with placebo (open circles and full line) as compared to patients treated with anti-IL-4R antibody mAb1 (plus sign and dashed line).
Figure 21:
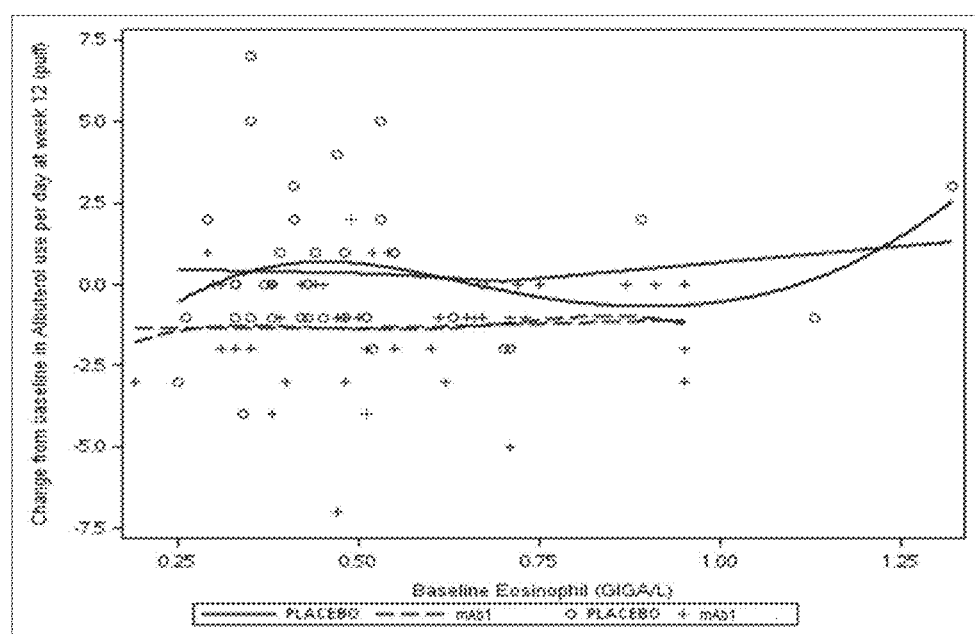
FIG. 21 is a scatter plot of the change in albuterol/levalbuterol use per day from baseline at week 12 versus blood eosinophils count (GIGA/L) in the mITT population treated with placebo (open circles and full line) as compared to patients treated with anti-IL-4R antibody mAb1 (plus sign and dashed line).
Figure 22:
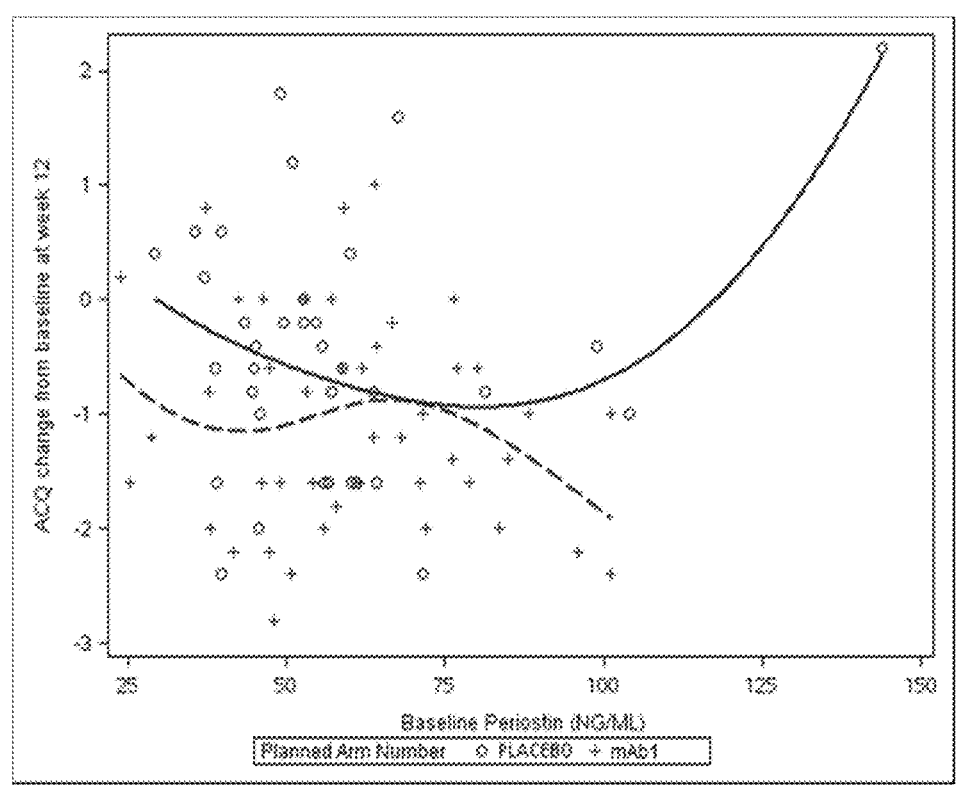
FIG. 22 is a scatter plot of the change in ACQ from baseline at week 12 versus baseline periostin in the mITT population treated with placebo (open circles and full line) as compared to patients treated with anti-IL-4R antibody mAb1 (plus sign and dashed line).
Figure 23:
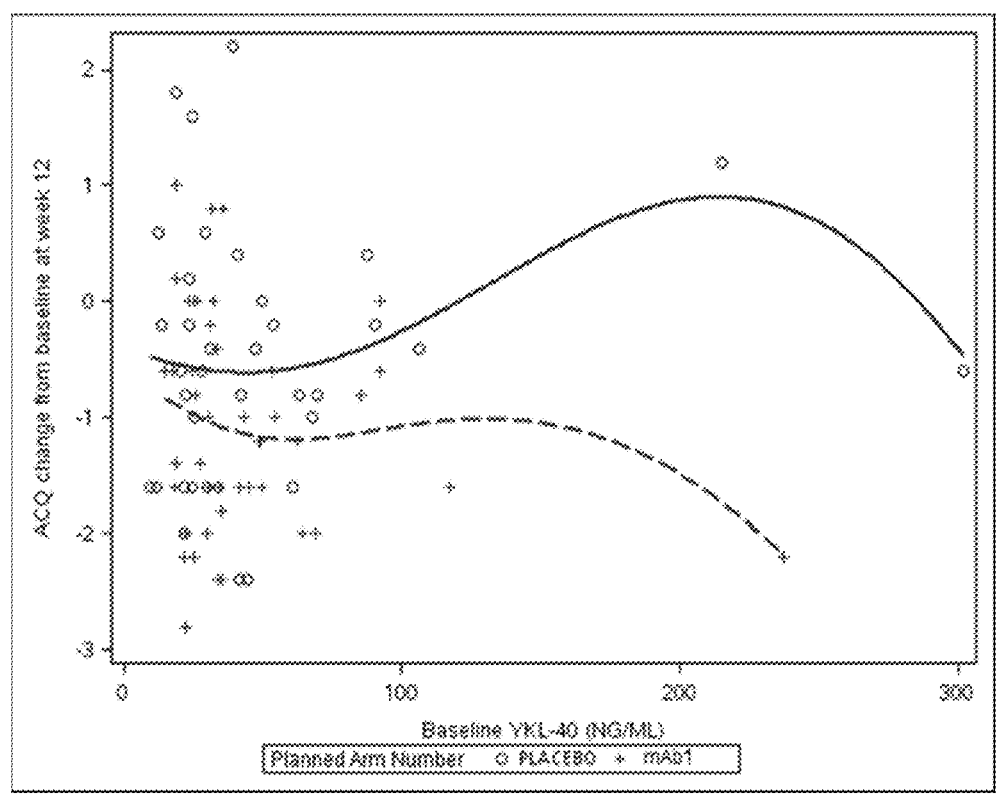
FIG. 23 is a scatter plot of the change in ACQ from baseline at week 12 versus YKL-40 in the mITT population treated with placebo (open circles and full line) as compared to patients treated with anti-IL-4R antibody mAb1 (plus sign and dashed line).

Scatter plot analysis of baseline eosinophils versus change from baseline in FEV1 at week 12 did not seem to suggest association of baseline eosinophils and treatment effect, as measured by change from baseline in FEV1 at week 12 in the study population (baseline eosinophils 0.3 Giga/L) (FIG. 19). Baseline eosinophils correlated with decreased ACQ (FIG. 20) and decreased albuterol/levalbuterol use (FIG. 21). Periostin and YKL-40 at baseline correlated with decreased ACQ (FIGS. 22 and 23).

The FEV1 change from baseline at week 12 was compounded by the withdrawal of ICS (starting at week 4). Similar analyses did not suggest association between baseline TARC or IgE and change from baseline in FEV1 at week 12 in the study population (baseline eosinophils 0.3 Giga/L).

Summary

These results show that mAb1 significantly reduced serum biomarkers associated with Th2 inflammation (TARC, eotaxin-3 and IgE) and bronchial inflammation (FeNO) in adult asthma patients. The correlation between FeNO reduction and $FEV_1$ improvement suggests a relationship between IL-4/IL-13 mediated anti-inflammatory activity and improvement in pulmonary function in moderate-to-severe, uncontrolled asthma.

The present invention is not to be limited in scope by the specific embodiments described herein. Indeed, various modifications in addition to those described herein will become apparent to those skilled in the art from the foregoing description and the accompanying figures. Such modifications are intended to fall within the scope of the appended claims.

Example 4

Blockade of the IL-4/IL-13 Signaling Pathway Inhibits IgE Production and Airway Remodeling in a Mouse Model of House Dust Mite-Induced Eosinophilic Asthma Introduction House dust mite allergen (HDM) has been shown to induce the Th2 immune response, including an influx of Th2 cells into the lung, and IL-4-induced trans-endothelial migration of eosinophils into the lungs. Eosinophils are the predominant effector cells in allergic reactions and the release of granule contents (including IL-4) from eosinophils contributes to inflammation. In asthmatic patients, Th2 driven production of IL-4 promotes eosinophil migration from blood into lungs via eotaxin, a potent eosinophil chemoattractant (Mochizuki et al., *J. Immunol.*, 1998, 160 (1):60-68). Moreover, when localized at the inflammatory site, eosinophils produce and secrete IL-4, thus contributing to ongoing Th2-driven inflammation (Bjerke et al., *Respir. Med.*, 1996, 90(5):271-277). In patients with allergic asthma, a challenge with HDM increased the level of IgE and Th2 cytokines in serum for up to 5 weeks after the allergen challenge (van de Pol et al., *Allergy*, 2012, 67(1): 67-73).

In this Example, an HDM-induced model of chronic asthma was used to evaluate the pharmacodynamic effects of anti-IL-4R antibodies on markers of airway inflammation in mice. Further, the effects of anti-IL-4R antibodies on collagen deposition in airways were evaluated in this model, since collagen deposition correlates with the extent of airway remodeling.

Materials and Methods

Two different anti-IL-4Rα antibodies were used in the experiments of this Example: "mAb1", a fully human monoclonal antibody specific for human IL-4Rα (i.e., the anti-IL-4R antibody used in the other working examples set forth herein); and "anti-mIL-4Rα", a mouse monoclonal antibody specific for the mouse IL-4Rα protein. mAb1 does not cross-react with mouse IL-4Rα; therefore, mAb1 was evaluated in humanized mice in which both human IL-4 and the ectodomain of IL-4Rα were engineered to replace their corresponding murine sequences in the mice (IL-4$^{hu/hu}$ IL-4Rα$^{hu/hu}$). The mouse anti-mouse IL-4Rα antibody "anti-mIL-4Rα," on the other hand, was tested in wild-type (Balb/c) mice. Also tested in these experiments was a mouse IL-13Rα2-mFc fusion protein that acts as a decoy receptor, blocking IL-13 signaling by sequestration of the IL-13 cytokine.

For the HDM-induced asthma model, mice were sensitized by daily intranasal application of HDM (50 μg per mouse in 20 μL of PBS) for 10 days, followed by rest (resolution period of 2 weeks). Allergen challenge was administered by intranasal application of HDM (50 μg per mouse in 20 μL of PBS) three times a week for 8 weeks. For each administration of HDM, either during sensitization or challenge period, the mice were lightly anesthetized with isoflurane.

Mice were acclimated in the experimental facility for a minimum of 5 days before initiating the experimental procedure. For the entire duration of the experiment, animals remained housed in the experimental facility under standard conditions in a 12-hour day/night cycle with access to food and water ad libitum. The number of mice per cage was limited to a maximum of 5 mice.

A total number of 48 humanized mice in which the human IL-4 ligand and the human ectodomain of IL-4Rα, were engineered to replace their corresponding murine sequences (IL-4$^{hu/hu}$ IL-4Rα$^{hu/hu}$) were used for two experiments. IL-4$^{hu/hu}$ IL-4Rα$^{hu/hu}$ mice were of a mixed background C57Bl/6NTac (75%)/129S6SvEvTac (25%). In addition, 20 wild type littermate mice on an identical mixed background were used in one of the three experiments. In each experiment, mice were sensitized with HDM (or with PBS in the control group) daily for ten days, followed by a resolution period from day 11 to day 29. From day 30, animals were challenged with HDM three times a week for 8 weeks, until day 81, and then euthanized on day 85 for analysis. Mice were divided into six experimental groups as follows:

(1) Non-Sensitized, not Treated:

PBS was applied intra-nasally during the sensitization and challenge periods. Mice were not treated with antibodies (IL-4$^{hu/hu}$ IL-4Rα$^{hu/hu}$ mice n=9; wild type littermates n=5);

(2) HDM-Sensitized, not Treated:

HDM was applied intra-nasally during the sensitization and challenge periods. Mice were not treated with antibodies (IL-4$^{hu/hu}$ IL-4Rα$^{hu/hu}$ mice n=7; wild type littermates n=5);

(3) HDM-Sensitized, Treated with Anti-mIL-4Rα:

HDM was applied intra-nasally during the sensitization and challenge periods. Mice were injected i.p. with anti-mIL-4Rα at dose 50 mg/kg, twice a week, from week 7 to week 12, for a total of 12 doses during a 6 week period (wild type littermates n=5);

(4) HDM-Sensitized, Treated with Anti-Human mAb1:

HDM was applied intra-nasally during the sensitization and challenge periods. Mice were injected i.p. with mAb1 at dose 50 mg/kg, twice a week, from week 7 to week 12, for a total of 12 doses during a 6 week period (IL-4$^{hu/hu}$ IL-4Rα$^{hu/hu}$ mice n=12);

(5) HDM-Sensitized, Treated with Mouse IL-13Ra2-mFc Fusion Protein:

HDM was applied intra-nasally during the sensitization and challenge periods. Mice were injected i.p. with the IL-13Rα2-mFc at dose 25 mg/kg, twice a week, from week 7 to week 12, for total of 12 doses during a 6 week period (IL-4$^{hu/hu}$ IL-4Rα$^{hu/hu}$ mice n=7; wild type littermates n=5);

(6) HDM-Sensitized, Treated with Isotype Control Antibody:

HDM was applied intra-nasally during the sensitization and challenge periods. Mice were injected i.p. with the isotype control Ab at dose 50 mg/kg, twice a week, from week 7 to week 12, for total of 12 doses during a 6 week period (IL-4$^{hu/hu}$ IL-4Rα$^{hu/hu}$ mice n=7).

Mice were euthanized on day 85, blood was collected for serum immunoglobulin level assays, and lung (one lobe) was used to generate either i) bronchoalveolar lavage (BAL) fluid, ii) a digested single-cell suspension sample for flow cytometric analysis, iii) a fixed formalin specimen for staining and histology analysis, or iv) a sample for analysis using the Sircol™ Collagen Assay (Biocolor Ltd, UK) to quantify the collagen content per lung lobe.

BAL fluid was obtained from euthanized animals by first exposing the trachea and introducing a 23 G lavage tube through a small incision in the tracheal wall. Sterile PBS (1 mL) was then injected into the lungs, and BAL fluid was recovered through the lavage tube using a syringe. 100 µL of BAL was loaded onto a Cytospin that was spun for 5 minutes at 500 rpm to extract the cells onto microscope slides. The slides were dried and H & E stained to visualize eosinophils.

Serum level of IgE was quantified using a commercially available ELISA kit. Briefly, serially diluted serum samples were incubated with anti-IgE capture antibody on 96-well plates and the IgE was detected by biotinylated anti-mouse IgE secondary antibody. Purified mouse IgE that was HRP-labeled was used as a standard.

HDM-specific IgG1 serum levels were quantified by ELISA. Briefly, HDM-coated plates were incubated with serially diluted serum samples, following by incubation with anti-mouse IgG1-HRP conjugated antibody. The relative levels of IgG1 serum levels were represented as titer units (OD450 was multiplied by a dilution factor required to achieve OD450≤0.5). Collected lung lobes were flash frozen in liquid nitrogen and stored at −80° C. until the extraction step. To extract the collagen, lungs were homogenized in ice-cold NaCl/NaHCO$_3$ solution and centrifuged at 9000×g for 10 min. This step was repeated three times, and resulting pellet was digested by pepsin in acetic acid for 18 hours at 4° C. Samples were centrifuged, and the supernatant was collected and mixed with Sircol™ Dye Reagent (Biocolor Ltd, UK) to stain for collagen content. Samples were washed with Acid-Salt Wash Reagent to remove unbound Sircol™ Dye (Biocolor Ltd, UK) and then mixed with Alkali Reagent. 200 µL of each sample was transferred into a 96-well plate, and OD at 555 nm was measured. A collagen standard was used for final quantification of collagen content in each sample.

Lungs were collected from euthanized mice and kept in complete DMEM medium on ice until digesting with a mixture of collagenase and DNAse in HBSS buffer for 20 minutes at 37° C. Collagenase activity was quenched by addition of 0.5M EDTA, samples were centrifuged, and red cells were lysed with ACK buffer. The cell suspensions obtained for each sample were divided into three separate pools and stained with antibody mix 1 (anti-CD11c-APC Ab, anti-SiglecF-PE Ab, anti-F4/80-FITC Ab, anti-CD45-PerCp-Cy5.5 Ab), or mix 2 (anti-CD11c-APC Ab, anti-CD11b-PerCp-Cy5.5 Ab, anti-CD103-FITC Ab, anti-MHCII-PE Ab), or mix 3 (anti-CD19-PE Ab, anti-Ly6G-APC Ab, anti-CD3-FITC, anti-CD11b-PerCp-Cy5.5 Ab) for 25 minutes at 4° C. Stained cells were fixed in Cytofix/Cytoperm solution for 30 minutes in 4° C., and stored in PBS until flow cytometry analysis by FACSCanto (BD Biosciences).

From the HDM-induced chronic model of eosinophilic asthma (EA), left lung lobes were collected from 4 mice per group for microarray analysis of gene expression using GeneChip® technology. Gene expression levels in the mice that were sensitized and challenged with HDM and then treated with an isotype control Ab were compared to gene expression levels in mice that were mock (PBS) sensitized and challenged and did not undergo antibody treatment. The threshold for a change in gene expression was set at >1.5-fold. The population of genes identified as being differentially expressed in mice that were sensitized and challenged with HDM were then further analyzed in the anti-IL-4Rα-treated group relative to the isotype control-treated group. The threshold for a change in gene expression in the IL-4Rα-Ab treated group relative to the isotype control-treated group was set at >2-fold.

Results

Figure 27:
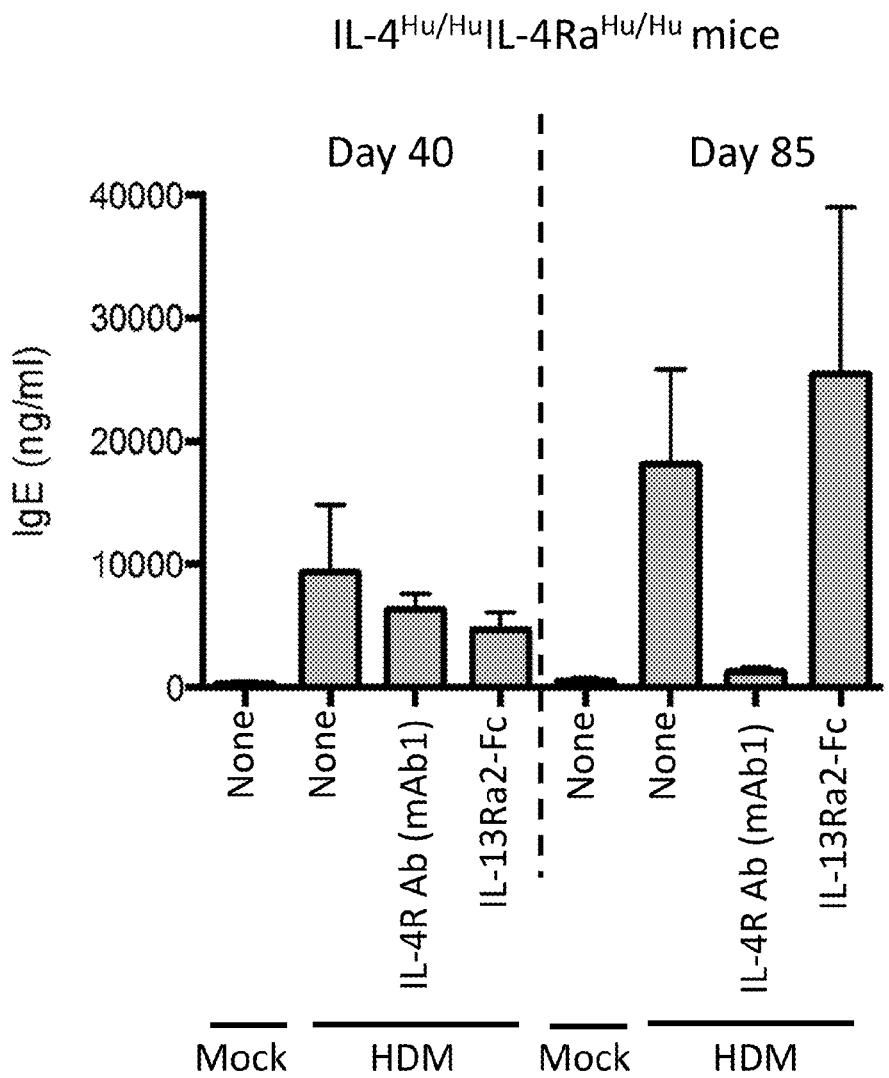
FIG. 27 is a graph showing the serum IgE levels in humanized IL-4/IL-4R mice (IL-4$^{hu/hu}$ IL-4R$\alpha^{hu/hu}$) following house dust mite (HDM) challenge and treatment with either anti-IL-4R antibody or an IL-13Ra2-Fc decoy receptor molecule, or mock treatment. Measurements were made on samples taken at Day 40 (24 hours prior to first dose of treatment) and at the end of the experiment on Day 85.

HDM sensitization and challenge resulted in increased levels of IgE and HDM-specific IgG1. IgE increase was completely blocked by both anti-IL-4Rα Abs but not by IL-13Ra2-Fc treatment (FIGS. 27A and 27B); HDM-specific IgG1 levels were not affected by any treatment (data not shown).

Figure 28:
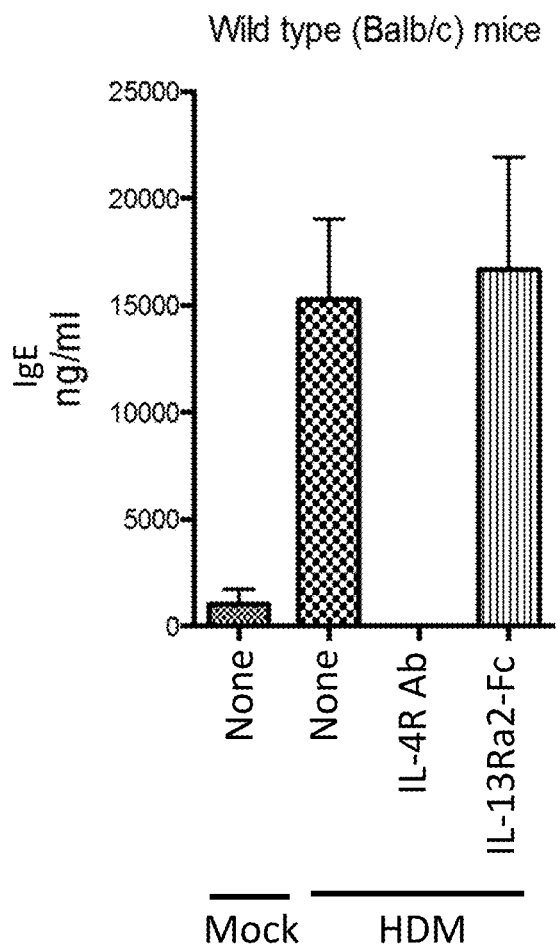
FIG. 28 is a graph showing the serum IgE levels in wild-type (Balb/c) mice following house dust mite (HDM) challenge and treatment with either isotype control, anti-IL-4R antibody or an IL-13Ra2-Fc decoy receptor molecule, or mock treatment.

HDM sensitization and challenge also caused an increase in collagen content in the lungs of the mice. Collagen content in the lungs of mice treated with both IL-4Rα Abs and IL-13Rα2-Fc protein was reduced to levels observed in mock sensitized & challenged mice (FIGS. 28A and 28B).

Figure 29:
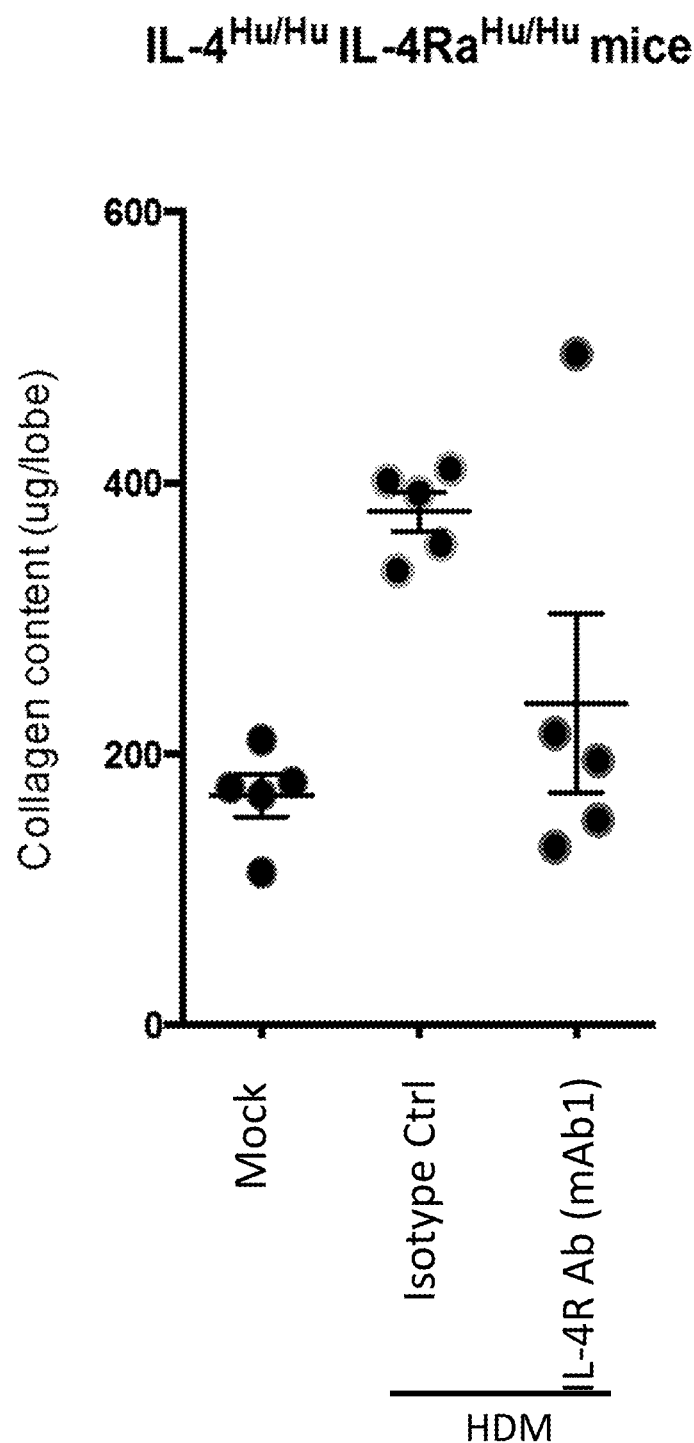
FIG. 29 is a graph showing the collagen content (expressed in terms of μg/lobe) of the lungs of humanized IL-4/IL-4R mice following HDM challenge and indicated treatment.
Figure 30:
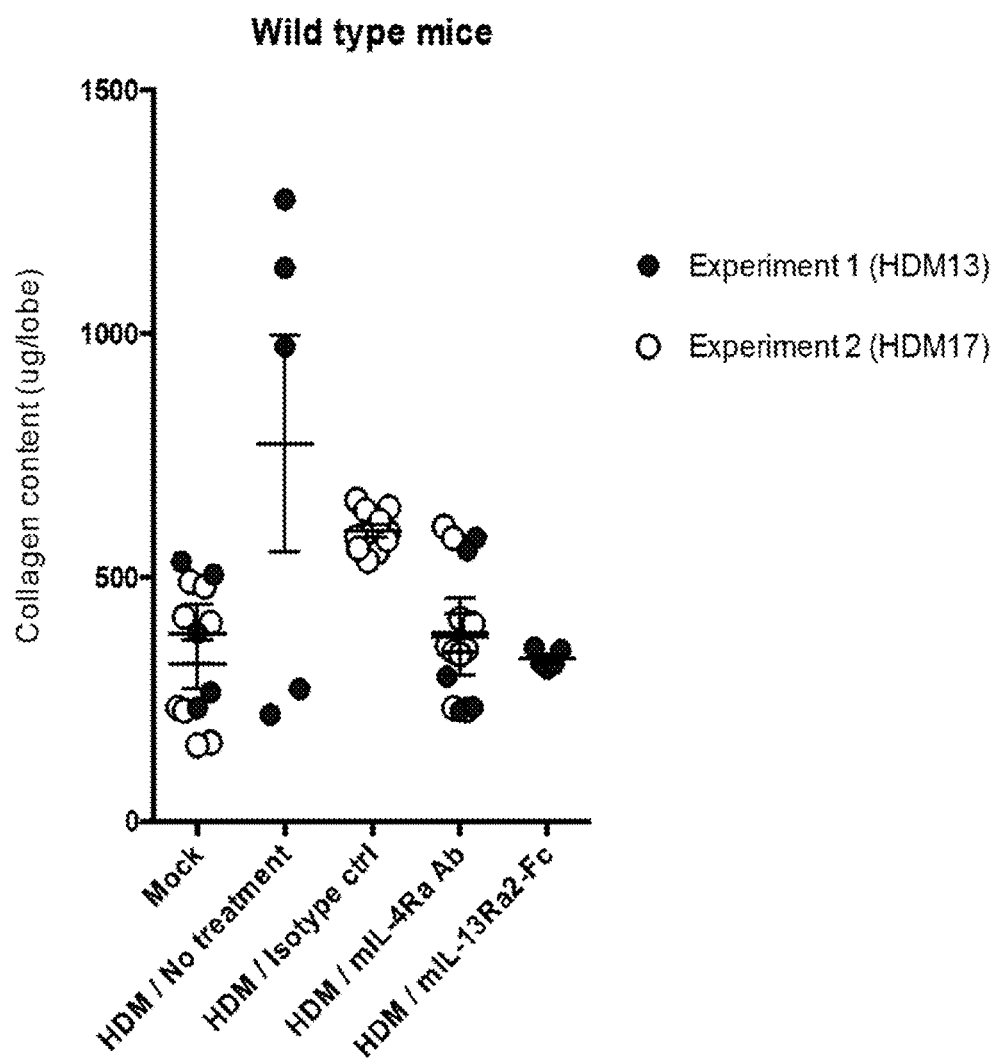
FIG. 30 is a graph showing the collagen content (expressed in terms of μg/lobe) of the lungs of wild-type mice following HDM challenge and indicated treatment.
Figure 31A:
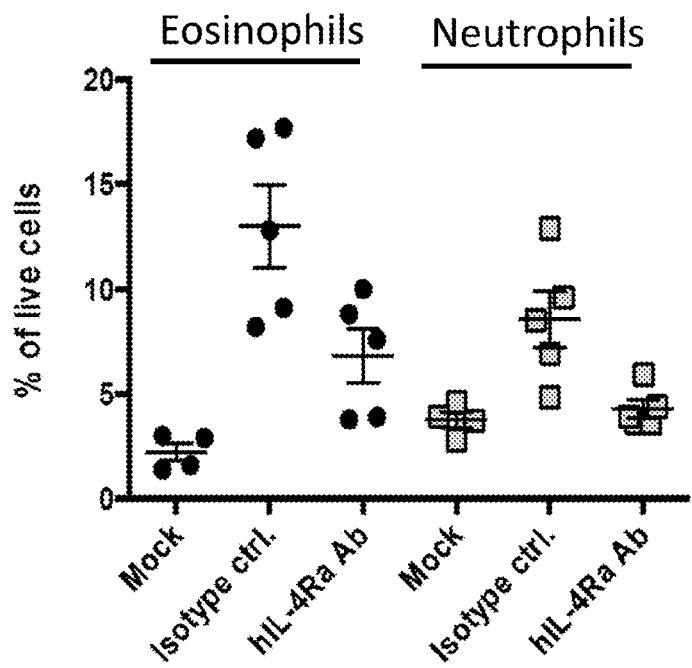
FIG. 31A is a graph showing the levels of eosinophils and neutrophils in humanized IL-4/IL-4R mice following HDM challenge and indicated treatment.
Figure 31B:
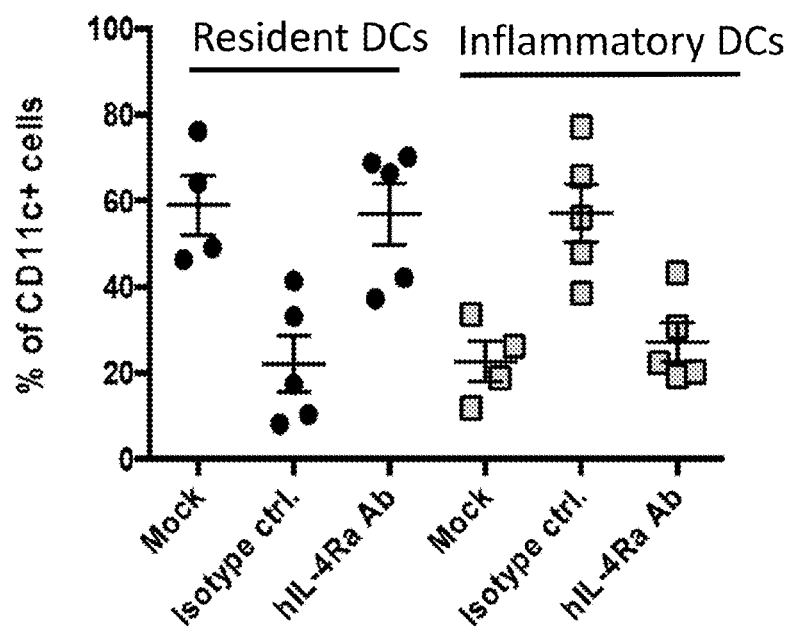
FIG. 31B is a graph showing the levels of resident dendritic cells and inflammatory dendritic cells, in humanized IL-4/IL-4R mice following HDM challenge and indicated treatment.

In addition, mAb1 treatment prevented influx of eosinophils, neutrophils, and inflammatory dendritic cells into lung (FIG. 29, Panels A and B).

Microarray analysis of mRNA isolated from lung tissue of HDM-induced IL-4$^{hu/hu}$ IL-4Rα$^{hu/hu}$ mice that were treated with an isotype control antibody revealed differential expression of 1468 genes (826 up-regulated and 642 down-regulated genes) as compared to mock sensitized and mock challenged mice. mAb1 treatment of HDM-induced IL-4$^{hu/hu}$ IL-4Rα$^{hu/hu}$ mice resulted in expression changes in only 521 genes (as compared to mock sensitized/challenged mice), effectively blocking about 65% genes affected by HDM sensitization/challenge (>1.5 fold change, p<0.05). Of particular interest is the finding that mAb1 mediated down-regulation of gene expression of several members of IL-1 cytokine family, specifically IL-1α (2.9-fold), IL-33 (2.6-fold) and IL-18 binding protein (1.5-fold). IL-1β gene expression did not increase in the HDM-induced, isotype control treated group (as compared to mock sensitized mice), but was decreased (1.5-fold) in the mAb1-treated groups. Gene expression of Th1 inflammatory cytokines IL-12β and IFN-γ was also downregulated by mAb1 as compared to the isotype control treated group. Notably, eight genes coding chemokine ligands involved in cell homing and trafficking were downregulated in the mAb1-treated group when compared to the isotype control treated group: Ccl11 (~9-fold reduction), Ccl8 and Cxcl2 (both ~5-fold reduction), Cxcl1, Ccl7, Ccl6 (all ~3-fold reduction), Ccl2 and Ccl9 (about 2-fold reduction).

Conclusions

This Example shows that blockade of IL-4 signaling via Type I and Type II receptors by anti-IL-4Rα antibodies suppresses inflammatory and fibrotic changes in lungs of HDM-challenged mice as well as gene signature changes driven by HDM.

Other embodiments are in the claims.

What is claimed is:

1. A method for the treatment of persistent asthma that reduces the incidence of asthma exacerbations or improves one or more asthma-associated parameter(s) in a subject with persistent asthma comprising sequentially administering to the subject a single initial dose of a pharmaceutical composition comprising an antibody or an antigen-binding fragment thereof, wherein the antibody or antigen-binding fragment thereof specifically binds an interleukin-4 receptor (IL-4R), and wherein administration of the single initial dose is followed by one or more secondary doses of the pharmaceutical composition comprising the antibody or antigen-binding fragment thereof, wherein the antibody or antigen-binding fragment thereof comprises heavy chain and light chain complementarity determining region (CDR) sequences from a heavy chain variable region (HCVR)/light chain variable region (LCVR) sequence pair of SEQ ID NOs: 162/164.

2. The method of claim 1, wherein the antibody or antigen binding fragment thereof comprises a heavy chain comprising heavy chain complementarity determining region (HCDR) sequences of SEQ ID NOs:148, 150, and 152, respectively, and a light chain comprising light chain complementarity determining region (LCDR) sequences of SEQ ID NOs:156, 158, and 160, respectively.

3. The method of claim 1, wherein each of the initial dose and the secondary doses comprise 75 mg to 600 mg of the antibody or antigen-binding fragment thereof.

4. The method of claim 1, wherein the pharmaceutical composition is administered to the subject systemically, subcutaneously, intravenously, or intranasally.

5. The method of claim 1, wherein the pharmaceutical composition comprising an antibody or antigen-binding fragment thereof is an add-on treatment to medium-to-high dose inhaled corticosteroid (ICS) and a second controller medication.

6. The method of claim 5, wherein the second controller medication is selected from the group consisting of: a Tumor Necrosis Factor (TNF) inhibitor, an interleukin-1 (IL-1) inhibitor, an interleukin 5 (IL-5) inhibitor, an interleukin-1 (IL-8) inhibitor, an immunoglobulin E (IgE) inhibitor, a leukotriene inhibitor, a corticosteroid, a methylxanthine, a non-steroidal anti-inflammatory drug (NSAID), nedocromil sodium, cromolyn sodium, a long-acting beta2 agonist (LABA), an anti-fungal agent, and a combination thereof.

7. The method of claim 1, wherein each secondary dose is administered 1 to 8 weeks after the immediately preceding dose.

8. The method of claim 1, wherein at least 8 secondary doses of the antibody or antigen-binding fragment thereof that specifically binds an interleukin-4 receptor (IL-4R) are administered to the subject, and wherein each secondary dose is administered 1 week after the immediately preceding dose.

9. The method of claim 1, wherein the expression level of one or more gene products selected from the group consisting of thymus and activation-regulated chemokine (TARC), IgE, eotaxin-3, periostin, carcinoembryonic antigen (CEA), and YKL-40 is reduced in the subject relative to baseline expression.

10. A method for the treatment of persistent asthma that reduces or eliminates an asthma patient's dependence on inhaled corticosteroids (ICS) and/or long-acting beta-agonists (LABA) for the treatment of one or more asthma exacerbations comprising:
  (a) selecting a patient with persistent asthma who has moderate-to-severe asthma that is uncontrolled with a background asthma therapy comprising an ICS, a LABA, or a combination thereof;
  (b) administering to the patient a defined dose of an antibody or antigen-binding fragment thereof that specifically binds to an Interleukin-4 receptor (IL-4R) at a defined frequency for an initial treatment period while maintaining the patient's background asthma therapy for the initial treatment period; and (c) gradually reducing or eliminating the dosage of ICS and/or LABA administered to the patient over the course of a subsequent treatment period while continuing to administer the antibody or antigen-binding fragment thereof at the defined frequency and dose used during the initial treatment period, wherein the antibody or antigen-binding fragment thereof comprises heavy chain and light chain complementarity determining region (CDR) sequences from a heavy chain variable region (HCVR)/light chain variable region (LCVR) sequence pair of SEQ ID NOs: 162/164.

11. The method of claim 10, wherein the ICS is fluticasone, budesonide, or mometasone.

12. The method of claim 10, wherein the LABA is salmeterol or formoterol.

13. The method of claim 10, wherein the ICS/LABA combination is fluticasone/salmeterol, budesonide/formoterol, or mometasone/formoterol.

14. The method of claim 10, wherein the dosage of LABA is eliminated at the end of the initial treatment period.

15. The method of claim 10, wherein the dosage of LABA and/or ICS is gradually reduced or eliminated over the course of 2 to 8 weeks.

16. The method of claim 10, wherein the antibody or antigen binding fragment thereof comprises a heavy chain comprising heavy chain complementarity determining region (HCDR) sequences of SEQ ID NOs:148, 150, and 152, respectively, and a light chain comprising light chain complementarity determining region (LCDR) sequences of SEQ ID NOs:156, 158, and 160, respectively.

17. The method of claim 10, wherein each of the doses comprises 75 mg to 600 mg of the antibody or antigen-binding fragment thereof.

18. The method of claim 10, wherein the pharmaceutical composition is administered to the subject systemically, subcutaneously, intravenously, or intranasally.

19. The method of claim 10, wherein the expression level of one or more gene products selected from the group consisting of thymus and activation-regulated chemokine (TARC), IgE, eotaxin-3, periostin, carcinoembryonic antigen (CEA), and YKL-40 is reduced in the subject relative to baseline expression.

* * * * *

UNITED STATES PATENT AND TRADEMARK OFFICE
CERTIFICATE OF CORRECTION

| | |
|---|---|
| PATENT NO. | : 9,574,004 B2 |
| APPLICATION NO. | : 13/971334 |
| DATED | : February 21, 2017 |
| INVENTOR(S) | : Marius Ardeleanu et al. |

It is certified that error appears in the above-identified patent and that said Letters Patent is hereby corrected as shown below:

In the Claims

At Column 196, Lines 34-35:
delete "an interleukin 5 (IL-5) inhibitor, interleukin-1 (IL-8) inhibitor," and insert --an interleukin-5 (IL-5) inhibitor, interleukin-8 (IL-8) inhibitor,--

At Column 197, Line 19:
delete "wherein the ICS/LAB A" and insert --wherein the ICS/LABA--

Signed and Sealed this
Eleventh Day of April, 2017

Michelle K. Lee
*Director of the United States Patent and Trademark Office*

SEQUENCE LISTING

<160> NUMBER OF SEQ ID NOS: 275

<210> SEQ ID NO 1
<211> LENGTH: 351
<212> TYPE: DNA
<213> ORGANISM: Artificial Sequence
<220> FEATURE:
<223> OTHER INFORMATION: Synthetic

<400> SEQUENCE: 1

```
caggtgcagc tggtggagtc tggggggaggc gtggtccagc ctgggaggtc cctgagactc      60
tcctgtgcag cctctggatt caccttccgc tcttatggca tgcactgggt ccgccaggct     120
ccaggcaagg ggctggagtg ggtggcggtc atatcatatg atggaagtaa taaatattat     180
atagactccg tgaagggccg attcaccatc tccagagaca attccaagaa cacgctgaat     240
ctgcaaatga acagcctgag acttgaggac acggctgtat attactgtgc gaaagagggg     300
agggggggat ttgactactg gggccaggga atcccggtca ccgtctcctc a              351
```

<210> SEQ ID NO 2
<211> LENGTH: 117
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Arg Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ile Asp Ser Val
     50                  55                  60

Lys Gly Arg Phe Thr Ile Ser Arg Asp Asn Ser Lys Asn Thr Leu Asn
 65                  70                  75                  80

Leu Gln Met Asn Ser Leu Arg Leu Glu Asp Thr Ala Val Tyr Tyr Cys
                 85                  90                  95

Ala Lys Glu Gly Arg Gly Gly Phe Asp Tyr Trp Gly Gln Gly Ile Pro
            100                 105                 110

Val Thr Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcacct tccgctctta tggc                                              24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Phe Thr Phe Arg Ser Tyr Gly
  1               5
```

<210> SEQ ID NO 5
<211> LENGTH: 24

-continued

```
<212> TYPE: DNA
<213> ORGANISM: Artificial Sequence
<220> FEATURE:
<223> OTHER INFORMATION: Synthetic

<400> SEQUENCE: 5
atatcatatg atggaagtaa taaa                                           24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Tyr Asp Gly Ser Asn Lys
 1               5

<210> SEQ ID NO 7
<211> LENGTH: 30
<212> TYPE: DNA
<213> ORGANISM: Artificial Sequence
<220> FEATURE:
<223> OTHER INFORMATION: Synthetic

<400> SEQUENCE: 7
gcgaaagagg ggagggggg atttgactac                                      30

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Ala Lys Glu Gly Arg Gly Gly Phe Asp Tyr
 1               5                   10

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcctca ctgtctgcat ctgtaggaga cagagtcacc      60
atcacttgtc gggcgagtca ggtcataaac aattatttag cctggtttca gcagaaacca     120
gggaaagtcc ctaagtccct gatccatgct gcatccagtt tacaaagtgg ggtcccatca     180
aagttcagcg gcagtggatc tgggacagat ttcactctca ccatcagcag cctgcagcct     240
gaagattttg caacttatta ctgccaacag tataatagtc acccgtggac gttcggccaa     300
gggaccaagg tggaaatcaa acga                                            324

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10
```

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Val Ile Asn Asn Tyr
                20                  25                  30

Leu Ala Trp Phe Gln Gln Lys Pro Gly Lys Val Pro Lys Ser Leu Ile
            35                  40                  45

His Ala Ala Ser Ser Leu Gln Ser Gly Val Pro Ser Lys Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser His Pro Trp
                85                  90                  95

Thr Phe Gly Gln Gly Thr Lys Val Glu Ile Lys Arg
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
caggtcataa acaattat                                                      18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Val Ile Asn Asn Tyr
 1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                                 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

```
Ala Ala Ser
 1
```

<210> SEQ ID NO 15
<211> LENGTH: 27
<212> TYPE: DNA
<213> ORGANISM: Artificial Sequence
<220> FEATURE:
<223> OTHER INFORMATION: Synthetic -continued

<400> SEQUENCE: 15
caacagtata atagtcaccc gtggacg                                27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Asn Ser His Pro Trp Thr
 1               5

<210> SEQ ID NO 17
<211> LENGTH: 351
<212> TYPE: DNA
<213> ORGANISM: Artificial Sequence
<220> FEATURE:
<223> OTHER INFORMATION: Synthetic

<400> SEQUENCE: 17
caggtgcagc tggtggagtc tgggggaggc gtggtccagc ctgggaggtc cctgagactc     60
tcctgtgcag cctctggatt caccttccgc tcttatggca tgcactgggt ccgccaggct    120
ccaggcaagg ggctggagtg ggtggcggtc atatcatatg atggaagtaa taaatattat    180
atagactccg tgaagggccg attcaccatc tccagagaca attccaagaa cacgctgaat    240
ctgcaaatga acagcctgag acttgaggac acggctgtat attactgtgc gaaagagggg    300 aggggggat tgactactg gggccaggga accctggtca ccgtctcctc a               351

<210> SEQ ID NO 18
<211> LENGTH: 117
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ile Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Leu Glu Asp Thr Ala Val Tyr Tyr Cys
                85                  90                  95

Ala Lys Glu Gly Arg Gly Gly Phe Asp Tyr Trp Gly Gln Gly Thr Leu
            100                 105                 110

Val Thr Val Ser Ser
        115

<210> SEQ ID NO 19
<211> LENGTH: 321
<212> TYPE: DNA
<213> ORGANISM: Artificial Sequence
<220> FEATURE:

<223> OTHER INFORMATION: Synthetic

<400> SEQUENCE: 19

```
gacatccaga tgacccagtc tccatcctca ctgtctgcat ctgtaggaga cagagtcacc    60
atcacttgtc gggcgagtca ggtcataaac aattatttag cctggtttca gcagaaacca   120
gggaaagtcc ctaagtccct gatccatgct gcatccagtt tacaaagtgg ggtcccatca   180
aagttcagcg gcagtggatc tgggacagat tcactctcac catcagcag cctgcagcct    240
gaagattttg caacttatta ctgccaacag tataatagtc acccgtggac gttcggccaa   300
gggaccaagg tggaaatcaa a                                             321
```

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Val Ile Asn Asn Tyr
             20                  25                  30

Leu Ala Trp Phe Gln Gln Lys Pro Gly Lys Val Pro Lys Ser Leu Ile
         35                  40                  45

His Ala Ala Ser Ser Leu Gln Ser Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser His Pro Trp
                 85                  90                  95

Thr Phe Gly Gln Gly Thr Lys Val Glu Ile Lys
            100                 105
```

<210> SEQ ID NO 21
<211> LENGTH: 351
<212> TYPE: DNA
<213> ORGANISM: Artificial Sequence
<220> FEATURE:
<223> OTHER INFORMATION: Synthetic

<400> SEQUENCE: 21

```
caggtgcagc tggtggagtc tgggggaggc gtggtccagc ctggagggtc cctgagactc    60
tcctgtgcag cctctggatt caccttccgc tcttatggca tgcactgggt ccgccaggct   120
ccaggcaagg ggctggagtg ggtggcagtt atatcatatg atggaagtaa taatactat    180
gcagactccg tgaagggccg attcaccatc tccagagaca attccaagaa cacgctgtat   240
ctgcaaatga acagcctgag agctgaggac acggctgtgt attactgtgc gaaagagggg   300
agggggggat tgactactg ggccaggga accctggtca ccgtctcctc a              351
```

<210> SEQ ID NO 22
<211> LENGTH: 117
<212> TYPE: PRT
<213> ORGANISM: Artificial Sequence
<220> FEATURE:
<223> OTHER INFORMATION: Synthetic

<400> SEQUENCE: 22

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Arg Gly Gly Phe Asp Tyr Trp Gly Gln Gly Thr Leu
            100                 105                 110

Val Thr Val Ser Ser
            115
```

```
<210> SEQ ID NO 23
<211> LENGTH: 322
<212> TYPE: DNA
<213> ORGANISM: Artificial Sequence
<220> FEATURE:
<223> OTHER INFORMATION: Synthetic

<400> SEQUENCE: 23
gacatccaga tgacccagtc tccatcctca ctgtctgcat ctgtaggaga cagagtcacc      60
atcacttgtc gggcgagtca ggtcataaac aattatttag cctggtttca gcagaaacca    120
gggaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtc acccgtggac gttcggccaa    300
gggaccaagg tggaaatcaa ac                                              322
```

```
<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Asn Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser His Pro Trp
                85                  90                  95

Thr Phe Gly Gln Gly Thr Lys Val Glu Ile Lys
            100                 105
```

```
<210> SEQ ID NO 25
```

-continued

```
<211> LENGTH: 351
<212> TYPE: DNA
<213> ORGANISM: Artificial Sequence
<220> FEATURE:
<223> OTHER INFORMATION: Synthetic

<400> SEQUENCE: 25
caggtgcagc tggtggagtc tgggggaggc gtggtccagc ctggagggtc cctgagactc    60
tcctgtgcag cctctggatt caccttcaga agctatggca tacactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacactgtat   240
ctgcaaatga acagcctgat aactgaggac acggctgtgt attattgtgt gaaagagggg   300 agggggggt tgactactg ggccaggga accacggtca ccgtctcctc a              351

<210> SEQ ID NO 26
<211> LENGTH: 117
<212> TYPE: PRT
<213> ORGANISM: Artificial Sequence
<220> FEATURE:
<223> OTHER INFORMATION: Synthetic

<400> SEQUENCE: 26

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Arg Ser Tyr
             20                  25                  30

Gly Ile His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Ile Thr Glu Asp Thr Ala Val Tyr Tyr Cys
                 85                  90                  95

Val Lys Glu Gly Arg Gly Gly Phe Asp Tyr Trp Gly Gln Gly Thr Thr
            100                 105                 110

Val Thr Val Ser Ser
        115

<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27
ggattcacct tcagaagcta tggc                                            24

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Gly Phe Thr Phe Arg Ser Tyr Gly
  1               5
```

<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29
atatcatatg atggaagtaa taaa                                           24

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Ile Ser Tyr Asp Gly Ser Asn Lys
 1               5

<210> SEQ ID NO 31
<211> LENGTH: 30
<212> TYPE: DNA
<213> ORGANISM: Artificial Sequence
<220> FEATURE:
<223> OTHER INFORMATION: Synthetic

<400> SEQUENCE: 31
gtgaaagagg ggagggggg gtttgactac                                      30

<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Val Lys Glu Gly Arg Gly Gly Phe Asp Tyr
 1               5                  10

<210> SEQ ID NO 33
<211> LENGTH: 324
<212> TYPE: DNA
<213> ORGANISM: Artificial Sequence
<220> FEATURE:
<223> OTHER INFORMATION: Synthetic

<400> SEQUENCE: 33
gacatccaga tgacccagtc tccatcctca ctgtctgcat ctgtaggaga cagagtcacc    60
atcacttgtc gggcgagtca ggtcattaat aattatttag cctggtttca gcagaaacca   120
gggaaagtcc ctaagtccct gatccatgct gcatccagtt tgcaaagagg ggtcccatca   180
aagttcagcg gcagtggatc tgggacagat ttcactctca ccatcaacag cctgcagcct   240
gaagattttg caacttatta ctgccaacaa tataatagtt acccgtggac gttcggccaa   300
gggaccaagg tggaaatcaa acga                                         324

<210> SEQ ID NO 34
<211> LENGTH: 108
<212> TYPE: PRT
<213> ORGANISM: Artificial Sequence
<220> FEATURE:
<223> OTHER INFORMATION: Synthetic -continued

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Asn Asn Tyr
            20                  25                  30

Leu Ala Trp Phe Gln Gln Lys Pro Gly Lys Val Pro Lys Ser Leu Ile
        35                  40                  45

His Ala Ala Ser Ser Leu Gln Arg Gly Val Pro Ser Lys Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys Arg
            100                 105

<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35
caggtcatta ataattat                                                18

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Gln Val Ile Asn Asn Tyr
1               5

<210> SEQ ID NO 37
<211> LENGTH: 9
<212> TYPE: DNA
<213> ORGANISM: Artificial Sequence
<220> FEATURE:
<223> OTHER INFORMATION: Synthetic

<400> SEQUENCE: 37 gctgcatcc                                                           9

<210> SEQ ID NO 38
<211> LENGTH: 3
<212> TYPE: PRT
<213> ORGANISM: Artificial Sequence
<220> FEATURE:
<223> OTHER INFORMATION: Synthetic

<400> SEQUENCE: 38

Ala Ala Ser
1

<210> SEQ ID NO 39
<211> LENGTH: 27
<212> TYPE: DNA
<213> ORGANISM: Artificial Sequence

```
<220> FEATURE:
<223> OTHER INFORMATION: Synthetic

<400> SEQUENCE: 39
caacaatata atagttaccc gtggacg                                              27

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Gln Gln Tyr Asn Ser Tyr Pro Trp Thr
 1               5

<210> SEQ ID NO 41
<211> LENGTH: 351
<212> TYPE: DNA
<213> ORGANISM: Artificial Sequence
<220> FEATURE:
<223> OTHER INFORMATION: Synthetic

<400> SEQUENCE: 41
caggtgcagc tggtggagtc tgggggaggc gtggtccagc ctggggaggtc cctgagactc          60 tcctgtgcag cctctggatt caccttcaga agctatggca tacactgggt ccgccaggct         120
ccaggcaagg ggctggagtg ggtggcagtt atatcatatg atggaagtaa taaatactat         180
gcagactccg tgaagggccg attcaccatc tccagagaca attccaagaa cacactgtat         240
ctgcaaatga acagcctgat aactgaggac acggctgtgt attattgtgt gaaagagggg         300 agggggggt tgactactg gggccaggga accctggtca ccgtctcctc a                    351

<210> SEQ ID NO 42
<211> LENGTH: 117
<212> TYPE: PRT
<213> ORGANISM: Artificial Sequence
<220> FEATURE:
<223> OTHER INFORMATION: Synthetic

<400> SEQUENCE: 42

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
                20                  25                  30

Gly Ile His Trp Val Arg Gln Ala Pro Gly Lys Gly Leu Glu Trp Val
            35                  40                  45

Ala Val Ile Ser Tyr Asp Gly Ser Asn Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Ile Thr Glu Asp Thr Ala Val Tyr Tyr Cys
                85                  90                  95

Val Lys Glu Gly Arg Gly Gly Phe Asp Tyr Trp Gly Gln Gly Thr Leu
                100                 105                 110

Val Thr Val Ser Ser
            115

<210> SEQ ID NO 43
<211> LENGTH: 321
```

<212> TYPE: DNA
<213> ORGANISM: Artificial Sequence
<220> FEATURE:
<223> OTHER INFORMATION: Synthetic

<400> SEQUENCE: 43

```
gacatccaga tgacccagtc tccatcctca ctgtctgcat ctgtaggaga cagagtcacc    60
atcacttgtc gggcgagtca ggtcattaat aattatttag cctggtttca gcagaaacca   120
gggaaagtcc ctaagtccct gatccatgct gcatccagtt tgcaaagagg ggtcccatca   180
aagttcagcg gcagtggatc tgggacagat ttcactctca ccatcaacag cctgcagcct   240
gaagattttg caacttatta ctgccaacaa tataatagtt acccgtggac gttcggccaa   300
gggaccaagg tggaaatcaa a                                              321
```

<210> SEQ ID NO 44
<211> LENGTH: 107
<212> TYPE: PRT
<213> ORGANISM: Artificial Sequence
<220> FEATURE:
<223> OTHER INFORMATION: Synthetic

<400> SEQUENCE: 44

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Val Ile Asn Asn Tyr
             20                  25                  30
Leu Ala Trp Phe Gln Gln Lys Pro Gly Lys Val Pro Lys Ser Leu Ile
         35                  40                  45
His Ala Ala Ser Ser Leu Gln Arg Gly Val Pro Ser Lys Phe Ser Gly
     50                  55                  60
Ser Gly Ser Gly Thr Asp Phe Thr Leu Thr Ile Asn Ser Leu Gln Pro
 65                  70                  75                  80
Glu Asp Phe Ala Thr Tyr Tyr Cys Gln Gln Tyr Asn Ser Tyr Pro Trp
                 85                  90                  95
Thr Phe Gly Gln Gly Thr Lys Val Glu Ile Lys
            100                 105
```

<210> SEQ ID NO 45
<211> LENGTH: 351
<212> TYPE: DNA
<213> ORGANISM: Artificial Sequence
<220> FEATURE:
<223> OTHER INFORMATION: Synthetic

<400> SEQUENCE: 45

```
caggtgcagc tggtggagtc tgggggaggc gtggtccagc ctggggggtc cctgagactc    60
tcctgtgcag cctctggatt caccttcaga agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgt gaaagagggg   300
aggggggggt tgactactg gggccaggga accctggtca ccgtctcctc a              351
```

<210> SEQ ID NO 46
<211> LENGTH: 117
<212> TYPE: PRT
<213> ORGANISM: Artificial Sequence
<220> FEATURE:
<223> OTHER INFORMATION: Synthetic

<400> SEQUENCE: 46

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Glu Gly Arg Gly Gly Phe Asp Tyr Trp Gly Gln Gly Thr Leu
            100                 105                 110

Val Thr Val Ser Ser
        115

<210> SEQ ID NO 47
<211> LENGTH: 322
<212> TYPE: DNA
<213> ORGANISM: Artificial Sequence
<220> FEATURE:
<223> OTHER INFORMATION: Synthetic

<400> SEQUENCE: 47
gacatccaga tgacccagtc tccatcctca ctgtctgcat ctgtaggaga cagagtcacc     60
atcacttgtc gggcgagtca ggtcattaat aattatttag cctggtttca gcagaaacca    120
gggaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacaa tataatagtt acccgtggac gttcggccaa    300
gggaccaagg tggaaatcaa ac                                              322

<210> SEQ ID NO 48
<211> LENGTH: 107
<212> TYPE: PRT
<213> ORGANISM: Artificial Sequence
<220> FEATURE:
<223> OTHER INFORMATION: Synthetic

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Asn Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105

<210> SEQ ID NO 49
<211> LENGTH: 375
<212> TYPE: DNA
<213> ORGANISM: Artificial Sequence
<220> FEATURE:
<223> OTHER INFORMATION: Synthetic

<400> SEQUENCE: 49

```
caggtgcagc tggtggagtc tgggggaggc ttggaacagc cggggggggtc cttgagactc    60 tcctgtgcag gctctggatt cacgtttaga gactatgcca tgacctgggt ccgccaggct   120
ccagggaagg ggctggagtg ggtcgcatcg attagtggtt ccggtggtaa cacatacttc   180
gcagactccg tgaagggccg gttcaccatc tccagagaca attccaagaa cacgctgtat   240
ctgcaaatga acagcctgag agccgaggac acggccgtat attactgtgc gaaagatcga   300
ctctctataa caattcgccc acgctattat ggtttggacg tctggggcca agggtccacg   360
gtcaccgtct cctca                                                    375
```

<210> SEQ ID NO 50
<211> LENGTH: 125
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Val Glu Ser Gly Gly Gly Leu Glu Gln Pro Gly Gly
  1               5                  10                  15

Ser Leu Arg Leu Ser Cys Ala Gly Ser Gly Phe Thr Phe Arg Asp Tyr
             20                  25                  30

Ala Met Thr Trp Val Arg Gln Ala Pro Gly Lys Gly Leu Glu Trp Val
         35                  40                  45

Ala Ser Ile Ser Gly Ser Gly Gly Asn Thr Tyr Phe Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
            100                 105                 110

Asp Val Trp Gly Gln Gly Ser Thr Val Thr Val Ser Ser
        115                 120                 125
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggattcacgt ttagagacta tgcc                                           24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

```
<400> SEQUENCE: 52

Gly Phe Thr Phe Arg Asp Tyr Ala
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
attagtggtt ccggtggtaa caca                                          24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Gly Ser Gly Gly Asn Thr
1               5

<210> SEQ ID NO 55
<211> LENGTH: 54
<212> TYPE: DNA
<213> ORGANISM: Artificial Sequence
<220> FEATURE:
<223> OTHER INFORMATION: Synthetic

<400> SEQUENCE: 55
gcgaaagatc gactctctat aacaattcgc ccacgctatt atggtttgga cgtc         54

<210> SEQ ID NO 56
<211> LENGTH: 18
<212> TYPE: PRT
<213> ORGANISM: Artificial Sequence
<220> FEATURE:
<223> OTHER INFORMATION: Synthetic

<400> SEQUENCE: 56

Ala Lys Asp Arg Leu Ser Ile Thr Ile Arg Pro Arg Tyr Tyr Gly Leu
1               5                   10                  15

Asp Val

<210> SEQ ID NO 57
<211> LENGTH: 324
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcctca ctgtctgcat ctgttggaga cagagtcacc    60
atcacttgtc gggcgagtca ggccattaac aatcatttag cctggtttca gcagaaacca   120
gggaaagccc ctaagtccct gatctttgct gtatccagtt tgcaaagtgg ggtcccatca   180
aagttcagcg gcagtggatc tgggacagac ttcactctca ccatcagcag cctgcagcct   240
gaagattttg caacttatta ctgccaacag tataatagtt acccgtggac gttcggccaa   300
gggaccaagg tggaaatcaa acga                                         324
```

<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

```
Asp Ile Gln Met Thr Gln Ser Pro Ser Leu Ser Ala Ser Val Gly
 1               5                  10                  15

Asp Arg Val Thr Ile Thr Cys Arg Ala Ser Gln Ala Ile Asn Asn His
             20                  25                  30

Leu Ala Trp Phe Gln Gln Lys Pro Gly Lys Ala Pro Lys Ser Leu Ile
         35                  40                  45

Phe Ala Val Ser Ser Leu Gln Ser Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Trp
                 85                  90                  95

Thr Phe Gly Gln Gly Thr Lys Val Glu Ile Lys Arg
            100                 105
```

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
caggccatta acaatcat                                                    18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

```
Gln Ala Ile Asn Asn His
 1               5
```

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgtatcc                                                               9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Val Ser

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtata atagttaccc gtggacg                                27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Ser Tyr Pro Trp Thr
 1               5

<210> SEQ ID NO 65
<211> LENGTH: 372
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggaacagc cggggggtc cttgagactc    60 tcctgtgcag gctctggatt cacgtttaga gactatgcca tgacctgggt ccgccaggct   120
ccagggaagg ggctggagtg ggtcgcatcg attagtggtt ccggtggtaa cacatacttc   180
gcagactccg tgaagggccg gttcaccatc tccagagaca attccaagaa cacgctgtat   240
ctgcaaatga acagcctgag agccgaggac acggccgtat attactgtgc gaaagatcga   300
ctctctataa caattcgccc acgctattat ggtttggacg tctggggcca agggaccacg   360
gtcaccgtct cc                                                      372

<210> SEQ ID NO 66
<211> LENGTH: 124
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Leu Glu Gln Pro Gly Gly
 1               5                  10                  15

Ser Leu Arg Leu Ser Cys Ala Gly Ser Gly Phe Thr Phe Arg Asp Tyr
             20                  25                  30

Ala Met Thr Trp Val Arg Gln Ala Pro Gly Lys Gly Leu Glu Trp Val
         35                  40                  45

Ala Ser Ile Ser Gly Ser Gly Gly Asn Thr Tyr Phe Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 67
<211> LENGTH: 321
<212> TYPE: DNA
<213> ORGANISM: Artificial Sequence
<220> FEATURE:
<223> OTHER INFORMATION: Synthetic

<400> SEQUENCE: 67
gacatccaga tgacccagtc tccatcctca ctgtctgcat ctgttggaga cagagtcacc      60
atcacttgtc gggcgagtca ggccattaac aatcatttag cctggtttca gcagaaacca     120
gggaaagccc ctaagtccct gatctttgct gtatccagtt tgcaaagtgg ggtcccatca     180
aagttcagcg gcagtggatc tgggacagac ttcactctca ccatcagcag cctgcagcct     240
gaagattttg caacttatta ctgccaacag tataatagtt acccgtggac gttcggccaa     300
gggaccaagg tggaaatcaa a                                               321

<210> SEQ ID NO 68
<211> LENGTH: 107
<212> TYPE: PRT
<213> ORGANISM: Artificial Sequence
<220> FEATURE:
<223> OTHER INFORMATION: Synthetic

<400> SEQUENCE: 68

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ala Ile Asn Asn His
            20                  25                  30

Leu Ala Trp Phe Gln Gln Lys Pro Gly Lys Ala Pro Lys Ser Leu Ile
        35                  40                  45

Phe Ala Val Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105

<210> SEQ ID NO 69
<211> LENGTH: 373
<212> TYPE: DNA
<213> ORGANISM: Artificial Sequence
<220> FEATURE:
<223> OTHER INFORMATION: Synthetic

<400> SEQUENCE: 69
gaggtgcagc tggtggagtc tgggggaggc ttggtacagc ctgggggtc cctgagactc       60 tcctgtgcag cctctggatt cacgtttaga gactatgcca tgagctgggt ccgccaggct     120
ccagggaagg gctggagtg gtctcagct attagtggtt ccgtggtaa cacatactac        180 gcagactccg tgaagggccg gttcaccatc tccagagaca attccaagaa cacgctgtat     240
ctgcaaatga acagcctgag agccgaggac acggccgtat attactgtgc gaaagatcga     300

```
ctctctataa caattcgccc acgctattat ggtttggacg tctggggcca agggaccacg    360
gtcaccgtct cct                                                       373
```

<210> SEQ ID NO 70
<211> LENGTH: 124
<212> TYPE: PRT
<213> ORGANISM: Artificial Sequence
<220> FEATURE:
<223> OTHER INFORMATION: Synthetic

<400> SEQUENCE: 70

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Asp Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120
```

<210> SEQ ID NO 71
<211> LENGTH: 322
<212> TYPE: DNA
<213> ORGANISM: Artificial Sequence
<220> FEATURE:
<223> OTHER INFORMATION: Synthetic

<400> SEQUENCE: 71

```
gacatccaga tgacccagtc tccatcctca ctgtctgcat ctgtaggaga cagagtcacc     60
atcacttgtc gggcgagtca ggccattaac aatcatttag cctggtttca gcagaaacca    120
gggaaagccc ctaagtccct gatctatgct gtatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtt acccgtggac gttcggccaa    300
gggaccaagg tggaaatcaa ac                                             322
```

<210> SEQ ID NO 72
<211> LENGTH: 107
<212> TYPE: PRT
<213> ORGANISM: Artificial Sequence
<220> FEATURE:
<223> OTHER INFORMATION: Synthetic

<400> SEQUENCE: 72

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Asn Asn His
            20                  25                  30

Leu Ala Trp Phe Gln Gln Lys Pro Gly Lys Ala Pro Lys Ser Leu Ile
        35                  40                  45
```

Tyr Ala Val Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Trp
                 85                  90                  95

Thr Phe Gly Gln Gly Thr Lys Val Glu Ile Lys
            100                 105

<210> SEQ ID NO 73
<211> LENGTH: 375
<212> TYPE: DNA
<213> ORGANISM: Artificial Sequence
<220> FEATURE:
<223> OTHER INFORMATION: Synthetic

<400> SEQUENCE: 73
caggtgcagc tggtggagtc tgggggaggc ttggaacagc cggggggtc cttgagactc        60 tcctgtgcag gctctggatt cacgtttaga gactatgcca tgacctgggt ccgccaggct      120
ccagggaagg gctggagtg gtcgcatcg attagtggtt ccggtggtaa cacatacttc        180
gcagactccg tgaagggccg gttcaccatc tccagagaca attccaagaa cacgctgtat      240
ctgcaaatga acagcctgag agccgaggac acggccgtat attactgtgc gaaagatcga      300
ctctctataa caattcgccc acgctattat ggtttggacg tctggggcca agggtccacg      360
gtcaccgtct cctca                                                        375

<210> SEQ ID NO 74
<211> LENGTH: 125
<212> TYPE: PRT
<213> ORGANISM: Artificial Sequence
<220> FEATURE:
<223> OTHER INFORMATION: Synthetic

<400> SEQUENCE: 74

Gln Val Gln Leu Val Glu Ser Gly Gly Gly Leu Glu Gln Pro Gly Gly
  1               5                  10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ala Ser Ile Ser Gly Ser Gly Gly Asn Thr Tyr Phe Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
            100                 105                 110

Asp Val Trp Gly Gln Gly Ser Thr Val Thr Val Ser Ser
        115                 120                 125

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75

```
ggattcacgt ttagagacta tgcc                                              24
```

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Gly Phe Thr Phe Arg Asp Tyr Ala
 1               5

<210> SEQ ID NO 77
<211> LENGTH: 24
<212> TYPE: DNA
<213> ORGANISM: Artificial Sequence
<220> FEATURE:
<223> OTHER INFORMATION: Synthetic

<400> SEQUENCE: 77

```
attagtggtt ccggtggtaa caca                                              24
```

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Ile Ser Gly Ser Gly Gly Asn Thr
 1               5

<210> SEQ ID NO 79
<211> LENGTH: 54
<212> TYPE: DNA
<213> ORGANISM: Artificial Sequence
<220> FEATURE:
<223> OTHER INFORMATION: Synthetic

<400> SEQUENCE: 79

```
gcgaaagatc gactctctat aacaattcgc ccacgctatt atggtttgga cgtc             54
```

<210> SEQ ID NO 80
<211> LENGTH: 18
<212> TYPE: PRT
<213> ORGANISM: Artificial Sequence
<220> FEATURE:
<223> OTHER INFORMATION: Synthetic

<400> SEQUENCE: 80

Ala Lys Asp Arg Leu Ser Ile Thr Ile Arg Pro Arg Tyr Tyr Gly Leu
 1               5                  10                  15

Asp Val

<210> SEQ ID NO 81
<211> LENGTH: 339
<212> TYPE: DNA
<213> ORGANISM: Artificial Sequence
<220> FEATURE:
<223> OTHER INFORMATION: Synthetic

<400> SEQUENCE: 81

```
gaaatagtgt tgacgcagtc tccactctcc ctgcccgtca cccctggaga gccggcctcc       60
```

```
atctcctgca ggtctagtca gagcctcctg tatagtattg gatacaacta tttggattgg    120
tacctgcaga agtcagggca gtctccacag ctccttatct atttgggttc taatcgggcc    180
tccggggtcc ctgacaggtt cagtggcagt ggatcaggca cagattttac actgaaaatc    240
agcagagtgg aggctgagga tgttgggttt tattactgca tgcaagctct acaaactccg    300 tacactttg gcccggggac caagctggag atcaaacga                            339
```

<210> SEQ ID NO 82
<211> LENGTH: 113
<212> TYPE: PRT
<213> ORGANISM: Artificial Sequence
<220> FEATURE:
<223> OTHER INFORMATION: Synthetic

<400> SEQUENCE: 82

```
Glu Ile Val Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Pro Gly Thr Lys Leu Glu Ile Lys
            100                 105                 110

Arg
```

<210> SEQ ID NO 83
<211> LENGTH: 33
<212> TYPE: DNA
<213> ORGANISM: Artificial Sequence
<220> FEATURE:
<223> OTHER INFORMATION: Synthetic

<400> SEQUENCE: 83

```
cagagcctcc tgtatagtat tggatacaac tat                                 33
```

<210> SEQ ID NO 84
<211> LENGTH: 11
<212> TYPE: PRT
<213> ORGANISM: Artificial Sequence
<220> FEATURE:
<223> OTHER INFORMATION: Synthetic

<400> SEQUENCE: 84

```
Gln Ser Leu Leu Tyr Ser Ile Gly Tyr Asn Tyr
 1               5                  10
```

<210> SEQ ID NO 85
<211> LENGTH: 9
<212> TYPE: DNA
<213> ORGANISM: Artificial Sequence
<220> FEATURE:
<223> OTHER INFORMATION: Synthetic

<400> SEQUENCE: 85 ttgggttct                                                                    9

<210> SEQ ID NO 86
<211> LENGTH: 3
<212> TYPE: PRT
<213> ORGANISM: Artificial Sequence
<220> FEATURE:
<223> OTHER INFORMATION: Synthetic

<400> SEQUENCE: 86

Leu Gly Ser
 1

<210> SEQ ID NO 87
<211> LENGTH: 27
<212> TYPE: DNA
<213> ORGANISM: Artificial Sequence
<220> FEATURE:
<223> OTHER INFORMATION: Synthetic

<400> SEQUENCE: 87
atgcaagctc tacaaactcc gtacact                                               27

<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Met Gln Ala Leu Gln Thr Pro Tyr Thr
 1               5

<210> SEQ ID NO 89
<211> LENGTH: 372
<212> TYPE: DNA
<213> ORGANISM: Artificial Sequence
<220> FEATURE:
<223> OTHER INFORMATION: Synthetic

<400> SEQUENCE: 89
gaggtgcagc tggtggagtc tgggggaggc ttggaacagc cggggggggtc cttgagactc           60 tcctgtgcag gctctggatt cacgtttaga gactatgcca tgacctgggt ccgccaggct          120
ccagggaagg ggctggagtg ggtcgcatcg attagtggtt ccggtggtaa cacatacttc          180
gcagactccg tgaagggccg gttcaccatc tccagagaca attccaagaa cacgctgtat          240
ctgcaaatga acagcctgag agccgaggac acggccgtat attactgtgc gaaagatcga          300
ctctctataa caattcgccc acgctattat ggtttggacg tctggggcca agggaccacg          360
gtcaccgtct cc                                                              372

<210> SEQ ID NO 90
<211> LENGTH: 124
<212> TYPE: PRT
<213> ORGANISM: Artificial Sequence
<220> FEATURE:
<223> OTHER INFORMATION: Synthetic

<400> SEQUENCE: 90

Glu Val Gln Leu Val Glu Ser Gly Gly Gly Leu Glu Gln Pro Gly Gly
 1               5                  10                  15

Ser Leu Arg Leu Ser Cys Ala Gly Ser Gly Phe Thr Phe Arg Asp Tyr
             20                  25                  30

Ala Met Thr Trp Val Arg Gln Ala Pro Gly Lys Gly Leu Glu Trp Val
         35                  40                  45

Ala Ser Ile Ser Gly Ser Gly Gly Asn Thr Tyr Phe Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
                100                 105                 110

Asp Val Trp Gly Gln Gly Thr Thr Val Thr Val Ser
            115                 120

<210> SEQ ID NO 91
<211> LENGTH: 336
<212> TYPE: DNA
<213> ORGANISM: Artificial Sequence
<220> FEATURE:
<223> OTHER INFORMATION: Synthetic

<400> SEQUENCE: 91
gatattgtga tgactcagtc tccactctcc ctgcccgtca cccctggaga gccggcctcc     60
atctcctgca ggtctagtca gagcctcctg tatagtattg atacaacta tttggattgg    120 tacctgcaga agtcagggca gtctccacag ctccttatct atttgggttc taatcgggcc   180
tccggggtcc ctgacaggtt cagtggcagt ggatcaggca cagattttac actgaaaatc   240
agcagagtgg aggctgagga tgttgggttt tattactgca tgcaagctct acaaactccg   300
tacacttttg gccgggggac caagctggag atcaaa                             336

<210> SEQ ID NO 92
<211> LENGTH: 112
<212> TYPE: PRT
<213> ORGANISM: Artificial Sequence
<220> FEATURE:
<223> OTHER INFORMATION: Synthetic

<400> SEQUENCE: 92

Asp Ile Val Met Thr Gln Ser Pro Leu Ser Leu Pro Val Thr Pro Gly
 1                5                  10                  15

Glu Pro Ala Ser Ile Ser Cys Arg Ser Ser Gln Ser Leu Leu Tyr Ser
                 20                  25                  30

Ile Gly Tyr Asn Tyr Leu Asp Trp Tyr Leu Gln Lys Ser Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Phe Tyr Tyr Cys Met Gln Ala
                 85                  90                  95

Leu Gln Thr Pro Tyr Thr Phe Gly Pro Gly Thr Lys Leu Glu Ile Lys
            100                 105                 110

<210> SEQ ID NO 93
<211> LENGTH: 373
<212> TYPE: DNA
<213> ORGANISM: Artificial Sequence
<220> FEATURE:
<223> OTHER INFORMATION: Synthetic

<400> SEQUENCE: 93

```
gaggtgcagc tggtggagtc tgggggaggc ttggtacagc ctggggggtc cctgagactc    60
tcctgtgcag cctctggatt cacgtttaga gactatgcca tgagctgggt ccgccaggct   120
ccagggaagg ggctggagtg ggtctcagct attagtggtt ccggtggtaa cacatactac   180
gcagactccg tgaagggccg gttcaccatc tccagagaca attccaagaa cacgctgtat   240
ctgcaaatga acagcctgag agccgaggac acggccgtat attactgtgc gaaagatcga   300
ctctctataa caattcgccc acgctattat ggtttggacg tctggggcca agggaccacg   360
gtcaccgtct cct                                                      373
```

<210> SEQ ID NO 94
<211> LENGTH: 124
<212> TYPE: PRT
<213> ORGANISM: Artificial Sequence
<220> FEATURE:
<223> OTHER INFORMATION: Synthetic

<400> SEQUENCE: 94

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Arg Asp Tyr
             20                  25                  30
Ala Met Ser Trp Val Arg Gln Ala Pro Gly Lys Gly Leu Glu Trp Val
         35                  40                  45
Ser Ala Ile Ser Gly Ser Gly Gly Asn Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Arg Leu Ser Ile Thr Ile Arg Pro Arg Tyr Tyr Gly Leu
            100                 105                 110
Asp Val Trp Gly Gln Gly Thr Thr Val Thr Val Ser
        115                 120
```

<210> SEQ ID NO 95
<211> LENGTH: 337
<212> TYPE: DNA
<213> ORGANISM: Artificial Sequence
<220> FEATURE:
<223> OTHER INFORMATION: Synthetic

<400> SEQUENCE: 95

```
gatattgtga tgactcagtc tccactctcc ctgcccgtca cccctggaga gccggcctcc    60
atctcctgca ggtctagtca gagcctcctg tatagtattg atacaacta tttggattgg   120
tacctgcaga agccagggca gtctccacag ctcctgatct atttgggttc taatcgggcc   180
tccggggtcc ctgacaggtt cagtggcagt ggatcaggca cagatttac actgaaaatc   240
agcagagtgg aggctgagga tgttggggtt tattactgca tgcaagctct acaaactccg   300
tacacttttg gccagggac caagctggag atcaaac                             337
```

<210> SEQ ID NO 96
<211> LENGTH: 112
<212> TYPE: PRT
<213> ORGANISM: Artificial Sequence
<220> FEATURE:

<223> OTHER INFORMATION: Synthetic

<400> SEQUENCE: 96

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 97
<211> LENGTH: 375
<212> TYPE: DNA
<213> ORGANISM: Artificial Sequence
<220> FEATURE:
<223> OTHER INFORMATION: Synthetic

<400> SEQUENCE: 97
caggtgcagc tggtggagtc tgagggactc ttggaacagc ctgggggtc cctgagactc      60
tcctgtgcag cctctggatt caactttaga gactttgcca tgacctgggt ccgccaggct    120
ccagggaagg ggctggagtg gtctcatct attagtggta gtggtagtaa tacatactac    180
gcagactccg tgaagggccg gttcaccatc tccagagaca attccaacca cacgctgtat    240
ctgcgaatga acagcctgag agccgaagac acggccgtgt attactgtgc gaaagatcga    300
ctctctataa caattcgccc acgctattac ggtctggacg tctggggcca agggtccacg    360
gtcaccgtct cctca                                                     375

<210> SEQ ID NO 98
<211> LENGTH: 125
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Glu Ser Glu Gly Leu Leu Glu Gln Pro Gly Gly
1               5                   10                  15

Ser Leu Arg Leu Ser Cys Ala Ala Ser Gly Phe Asn Phe Arg Asp Phe
            20                  25                  30

Ala Met Thr Trp Val Arg Gln Ala Pro Gly Lys Gly Leu Glu Trp Val
        35                  40                  45

Ser Ser Ile Ser Gly Ser Gly Ser Asn Thr Tyr Tyr Ala Asp Ser Val
    50                  55                  60

Lys Gly Arg Phe Thr Ile Ser Arg Asp Asn Ser Asn His Thr Leu Tyr
65                  70                  75                  80

Leu Arg Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Ser Thr Val Thr Val Ser Ser
        115                 120                 125

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcaact ttagagactt tgcc                                    24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Asn Phe Arg Asp Phe Ala
1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
attagtggta gtggtagtaa taca                                    24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Gly Ser Gly Ser Asn Thr
1               5

<210> SEQ ID NO 103
<211> LENGTH: 54
<212> TYPE: DNA
<213> ORGANISM: Artificial Sequence
<220> FEATURE:
<223> OTHER INFORMATION: Synthetic

<400> SEQUENCE: 103
gcgaaagatc gactctctat aacaattcgc ccacgctatt acggtctgga cgtc       54

<210> SEQ ID NO 104
<211> LENGTH: 18
<212> TYPE: PRT
<213> ORGANISM: Artificial Sequence
<220> FEATURE:
<223> OTHER INFORMATION: Synthetic

<400> SEQUENCE: 104

Ala Lys Asp Arg Leu Ser Ile Thr Ile Arg Pro Arg Tyr Tyr Gly Leu
1               5                   10                  15

Asp Val

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105

```
gacatccaga tgacccagtc tccatcctcc ctgtctgcat ctgtaggaga cagagtcacc    60
atcacttgcc gggcgagtca ggacattagc aattattttg cctggtatca gcagaagcca   120
gggaaagttc ctaagctcct gatctttgct gcatccactt tgcatccagg ggtcccatct   180
cggttcagtg gcagtggatc tgggacagat ttcactctca ccattcgcag cctgcagcct   240
gaagatgttg caacttatta ctgtcaaaaa tatgacagtg ccccgtacac ttttggccag   300
gggaccaagg tggaaatcaa acga                                          324
```

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Asn Tyr
            20                  25                  30
Phe Ala Trp Tyr Gln Gln Lys Pro Gly Lys Val Pro Lys Leu Leu Ile
        35                  40                  45
Phe Ala Ala Ser Thr Leu His Pro Gly Val Pro Ser Arg Phe Ser Gly
    50                  55                  60
Ser Gly Ser Gly Thr Asp Phe Thr Leu Thr Ile Arg Ser Leu Gln Pro
65                  70                  75                  80
Glu Asp Val Ala Thr Tyr Tyr Cys Gln Lys Tyr Asp Ser Ala Pro Tyr
                85                  90                  95
Thr Phe Gly Gln Gly Thr Lys Val Glu Ile Lys Arg
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107

```
caggacatta gcaattat                                                  18
```

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Asp Ile Ser Asn Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                                9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caaaaatatg acagtgcccc gtacact                                           27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Lys Tyr Asp Ser Ala Pro Tyr Thr
 1               5

<210> SEQ ID NO 113
<211> LENGTH: 372
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgagggactc ttggaacagc ctgggggtc cctgagactc         60 tcctgtgcag cctctggatt caactttaga gactttgcca tgacctgggt ccgccaggct       120
ccagggaagg gctggagtg gtctcatct attagtggta gtggtagtaa tacatactac         180
gcagactccg tgaagggccg gttcaccatc tccagagaca attccaacca cacgctgtat       240
ctgcgaatga acagcctgag agccgaagac acggccgtgt attactgtgc gaaagatcga       300
ctctctataa caattcgccc acgctattac ggtctggacg tctggggcca agggaccacg       360
gtcaccgtct cc                                                          372

<210> SEQ ID NO 114
<211> LENGTH: 124
<212> TYPE: PRT

<213> ORGANISM: Artificial Sequence
<220> FEATURE:
<223> OTHER INFORMATION: Synthetic

<400> SEQUENCE: 114

```
Glu Val Gln Leu Val Glu Ser Glu Gly Leu Leu Glu Gln Pro Gly Gly
  1               5                  10                  15

Ser Leu Arg Leu Ser Cys Ala Ala Ser Gly Phe Asn Phe Arg Asp Phe
             20                  25                  30

Ala Met Thr Trp Val Arg Gln Ala Pro Gly Lys Gly Leu Glu Trp Val
         35                  40                  45

Ser Ser Ile Ser Gly Ser Gly Ser Asn Thr Tyr Tyr Ala Asp Ser Val
 50                  55                  60

Lys Gly Arg Phe Thr Ile Ser Arg Asp Asn Ser Asn His Thr Leu Tyr
 65                  70                  75                  80

Leu Arg Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120
```

<210> SEQ ID NO 115
<211> LENGTH: 321
<212> TYPE: DNA
<213> ORGANISM: Artificial Sequence
<220> FEATURE:
<223> OTHER INFORMATION: Synthetic

<400> SEQUENCE: 115

```
gacatccaga tgacccagtc tccatcctcc ctgtctgcat ctgtaggaga cagagtcacc    60
atcacttgcc gggcgagtca ggacattagc aattattttg cctggtatca gcagaagcca   120
gggaaagttc ctaagctcct gatctttgct gcatccactt tgcatccagg ggtcccatct   180
cggttcagtg gcagtggatc tgggacagat ttcactctca ccattcgcag cctgcagcct   240
gaagatgttg caacttatta ctgtcaaaaa tatgacagtg ccccgtacac ttttggccag   300
gggaccaagc tggagatcaa a                                             321
```

<210> SEQ ID NO 116
<211> LENGTH: 107
<212> TYPE: PRT
<213> ORGANISM: Artificial Sequence
<220> FEATURE:
<223> OTHER INFORMATION: Synthetic

<400> SEQUENCE: 116

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
             20                  25                  30

Phe Ala Trp Tyr Gln Gln Lys Pro Gly Lys Val Pro Lys Leu Leu Ile
         35                  40                  45

Phe Ala Ala Ser Thr Leu His Pro Gly Val Pro Ser Arg Phe Ser Gly
 50                  55                  60

Ser Gly Ser Gly Thr Asp Phe Thr Leu Thr Ile Arg Ser Leu Gln Pro
 65                  70                  75                  80

Glu Asp Val Ala Thr Tyr Tyr Cys Gln Lys Tyr Asp Ser Ala Pro Tyr
                 85                  90                  95
```

Thr Phe Gly Gln Gly Thr Lys Leu Glu Ile Lys
            100                 105

<210> SEQ ID NO 117
<211> LENGTH: 373
<212> TYPE: DNA
<213> ORGANISM: Artificial Sequence
<220> FEATURE:
<223> OTHER INFORMATION: Synthetic

<400> SEQUENCE: 117
gaggtgcagc tggtggagtc tgggggaggc ttggtacagc ctgggggtc cctgagactc      60 tcctgtgcag cctctggatt caactttaga ctttgcca tgagctgggt ccgccaggct     120
ccagggaagg gctggagtg gtctcagct attagtggta gtggtagtaa tacatactac     180
gcagactccg tgaagggccg gttcaccatc tccagagaca attccaagaa cacgctgtat     240
ctgcaaatga acagcctgag agccgaggac acggccgtat attactgtgc gaaagatcga     300
ctctctataa caattcgccc acgctattac ggtctggacg tctggggcca agggaccacg     360
gtcaccgtct cct                                                        373

<210> SEQ ID NO 118
<211> LENGTH: 124
<212> TYPE: PRT
<213> ORGANISM: Artificial Sequence
<220> FEATURE:
<223> OTHER INFORMATION: Synthetic

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Arg Asp Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 119
<211> LENGTH: 322
<212> TYPE: DNA
<213> ORGANISM: Artificial Sequence
<220> FEATURE:
<223> OTHER INFORMATION: Synthetic

<400> SEQUENCE: 119
gacatccaga tgacccagtc tccatcctcc ctgtctgcat ctgtaggaga cagagtcacc      60
atcacttgcc gggcgagtca ggacattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240

-continued

```
gaagatgttg caacttatta ctgtcaaaaa tatgacagtg ccccgtacac ttttggccag      300
gggaccaagc tggagatcaa ac                                              322
```

<210> SEQ ID NO 120
<211> LENGTH: 107
<212> TYPE: PRT
<213> ORGANISM: Artificial Sequence
<220> FEATURE:
<223> OTHER INFORMATION: Synthetic

<400> SEQUENCE: 120

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Tyr
                85                  90                  95

Thr Phe Gly Gln Gly Thr Lys Leu Glu Ile Lys
            100                 105
```

<210> SEQ ID NO 121
<211> LENGTH: 357
<212> TYPE: DNA
<213> ORGANISM: Artificial Sequence
<220> FEATURE:
<223> OTHER INFORMATION: Synthetic

<400> SEQUENCE: 121

```
caggtgcagc tggtggagtc tgggggaggc ttggtacagc ctggggggtc cctgagactc      60
tcctgtgtag cttctggatt cacccttaac aactttgtca tgaactgggt ccgccaggtt     120
ccagggaagg gactggagtg gtctcttttt attagtgcta gtggtggtag tatatactac     180
gcagactccg tgaagggccg gttcaccatc tccagagaca cttccaagaa cacattatat     240
ctgcaaatga acagcctgag agccgacgac acggccgtct attactgtgc gaaatccccg     300
tataactgga ccccttttga ctattggggc cagggaacca cggtcaccgt ctcctca       357
```

<210> SEQ ID NO 122
<211> LENGTH: 119
<212> TYPE: PRT
<213> ORGANISM: Artificial Sequence
<220> FEATURE:
<223> OTHER INFORMATION: Synthetic

<400> SEQUENCE: 122

```
Gln Val Gln Leu Val Glu Ser Gly Gly Gly Leu Val Gln Pro Gly Gly
 1               5                  10                  15

Ser Leu Arg Leu Ser Cys Val Ala Ser Gly Phe Thr Leu Asn Asn Phe
            20                  25                  30

Val Met Asn Trp Val Arg Gln Val Pro Gly Lys Gly Leu Glu Trp Val
        35                  40                  45

Ser Phe Ile Ser Ala Ser Gly Gly Ser Ile Tyr Tyr Ala Asp Ser Val
    50                  55                  60
```

Lys Gly Arg Phe Thr Ile Ser Arg Asp Thr Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Lys Ser Pro Tyr Asn Trp Asn Pro Phe Asp Tyr Trp Gly Gln Gly
            100                 105                 110

Thr Thr Val Thr Val Ser Ser
        115

<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123
ggattcaccc ttaacaactt tgtc                                          24

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Gly Phe Thr Leu Asn Asn Phe Val
1               5

<210> SEQ ID NO 125
<211> LENGTH: 24
<212> TYPE: DNA
<213> ORGANISM: Artificial Sequence
<220> FEATURE:
<223> OTHER INFORMATION: Synthetic

<400> SEQUENCE: 125
attagtgcta gtggtggtag tata                                          24

<210> SEQ ID NO 126
<211> LENGTH: 8
<212> TYPE: PRT
<213> ORGANISM: Artificial Sequence
<220> FEATURE:
<223> OTHER INFORMATION: Synthetic

<400> SEQUENCE: 126

Ile Ser Ala Ser Gly Gly Ser Ile
1               5

<210> SEQ ID NO 127
<211> LENGTH: 36
<212> TYPE: DNA
<213> ORGANISM: Artificial Sequence
<220> FEATURE:
<223> OTHER INFORMATION: Synthetic

<400> SEQUENCE: 127
gcgaaatccc cgtataactg gaaccccttt gactat                             36

<210> SEQ ID NO 128
<211> LENGTH: 12
<212> TYPE: PRT

<213> ORGANISM: Artificial Sequence
<220> FEATURE:
<223> OTHER INFORMATION: Synthetic

<400> SEQUENCE: 128

Ala Lys Ser Pro Tyr Asn Trp Asn Pro Phe Asp Tyr
1               5                   10

<210> SEQ ID NO 129
<211> LENGTH: 327
<212> TYPE: DNA
<213> ORGANISM: Artificial Sequence
<220> FEATURE:
<223> OTHER INFORMATION: Synthetic

<400> SEQUENCE: 129

```
gacatccagt tgacccagtc tccagccacc ctgtctgtgt ctccagggga acgagccacc      60
ctctcctgca gggccagtct gagtgttagc agcaaattag cctggtacca gcagacacct     120
ggccaggctc ccagactcct catctatagt gcctccaccc gggccactgg tatcccagtc     180
aggttcagtg gcagtgggtc tgggacagag ttcactctca ccatcagcag cctgcagtct     240
gaagattttg cggtttatta ctgtcagcag tataatcatt ggcctccgta cacttttggc     300
caggggacca aggtggagat caaacga                                         327
```

<210> SEQ ID NO 130
<211> LENGTH: 109
<212> TYPE: PRT
<213> ORGANISM: Artificial Sequence
<220> FEATURE:
<223> OTHER INFORMATION: Synthetic

<400> SEQUENCE: 130

Asp Ile Gln Leu Thr Gln Ser Pro Ala Thr Leu Ser Val Ser Pro Gly
1               5                   10                  15

Glu Arg Ala Thr Leu Ser Cys Arg Ala Ser Leu Ser Val Ser Ser Lys
                20                  25                  30

Leu Ala Trp Tyr Gln Gln Thr Pro Gly Gln Ala Pro Arg Leu Leu Ile
            35                  40                  45

Tyr Ser Ala Ser Thr Arg Ala Thr Gly Ile Pro Val Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn His Trp Pro Pro
                85                  90                  95

Tyr Thr Phe Gly Gln Gly Thr Lys Val Glu Ile Lys Arg
            100                 105

<210> SEQ ID NO 131
<211> LENGTH: 18
<212> TYPE: DNA
<213> ORGANISM: Artificial Sequence
<220> FEATURE:
<223> OTHER INFORMATION: Synthetic

<400> SEQUENCE: 131

```
ctgagtgtta gcagcaaa                                                    18
```

<210> SEQ ID NO 132
<211> LENGTH: 6
<212> TYPE: PRT
<213> ORGANISM: Artificial Sequence

```
<220> FEATURE:
<223> OTHER INFORMATION: Synthetic

<400> SEQUENCE: 132

Leu Ser Val Ser Ser Lys
 1               5

<210> SEQ ID NO 133
<211> LENGTH: 9
<212> TYPE: DNA
<213> ORGANISM: Artificial Sequence
<220> FEATURE:
<223> OTHER INFORMATION: Synthetic

<400> SEQUENCE: 133 agtgcctcc                                                                  9

<210> SEQ ID NO 134
<211> LENGTH: 3
<212> TYPE: PRT
<213> ORGANISM: Artificial Sequence
<220> FEATURE:
<223> OTHER INFORMATION: Synthetic

<400> SEQUENCE: 134

Ser Ala Ser
 1

<210> SEQ ID NO 135
<211> LENGTH: 30
<212> TYPE: DNA
<213> ORGANISM: Artificial Sequence
<220> FEATURE:
<223> OTHER INFORMATION: Synthetic

<400> SEQUENCE: 135
cagcagtata atcattggcc tccgtacact                                           30

<210> SEQ ID NO 136
<211> LENGTH: 10
<212> TYPE: PRT
<213> ORGANISM: Artificial Sequence
<220> FEATURE:
<223> OTHER INFORMATION: Synthetic

<400> SEQUENCE: 136

Gln Gln Tyr Asn His Trp Pro Pro Tyr Thr
 1               5                  10

<210> SEQ ID NO 137
<211> LENGTH: 357
<212> TYPE: DNA
<213> ORGANISM: Artificial Sequence
<220> FEATURE:
<223> OTHER INFORMATION: Synthetic

<400> SEQUENCE: 137
gaggtgcagc tggtggagtc tgggggaggc ttggtacagc ctggggggtc cctgagactc          60
tcctgtgtag cttctggatt caccttaac aactttgtca tgaactgggt ccgccaggtt         120
ccagggaagg gactggagtg ggtctctttt attagtgcta gtggtggtag tatatactac        180
gcagactccg tgaagggccg gttcaccatc tccagagaca cttccaagaa cacattatat        240
ctgcaaatga acagcctgag agccgacgac acggccgtct attactgtgc gaaatccccg        300
tataactgga ccccctttga ctattggggc cagggaaccc tggtcaccgt ctcctca           357
```

<210> SEQ ID NO 138
<211> LENGTH: 119
<212> TYPE: PRT
<213> ORGANISM: Artificial Sequence
<220> FEATURE:
<223> OTHER INFORMATION: Synthetic

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Leu Asn Asn Phe
            20                  25                  30

Val Met Asn Trp Val Arg Gln Val Pro Gly Lys Gly Leu Glu Trp Val
        35                  40                  45

Ser Phe Ile Ser Ala Ser Gly Gly Ser Ile Tyr Tyr Ala Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Lys Ser Pro Tyr Asn Trp Asn Pro Phe Asp Tyr Trp Gly Gln Gly
            100                 105                 110

Thr Leu Val Thr Val Ser Ser
        115

<210> SEQ ID NO 139
<211> LENGTH: 324
<212> TYPE: DNA
<213> ORGANISM: Artificial Sequence
<220> FEATURE:
<223> OTHER INFORMATION: Synthetic

<400> SEQUENCE: 139
gaaatagtga tgacgcagtc tccagccacc ctgtctgtgt ctccagggga acgagccacc      60
ctctcctgca gggccagtct gagtgttagc agcaaattag cctggtacca gcagacacct     120
ggccaggctc ccagactcct catctatagt gcctccaccc gggccactgg tatcccagtc     180
aggttcagtg gcagtgggtc tgggacagag ttcactctca ccatcagcag cctgcagtct     240
gaagattttg cggtttatta ctgtcagcag tataatcatt ggcctccgta cacttttggc     300
caggggacca agctggagat caaa                                            324

<210> SEQ ID NO 140
<211> LENGTH: 108
<212> TYPE: PRT
<213> ORGANISM: Artificial Sequence
<220> FEATURE:
<223> OTHER INFORMATION: Synthetic

<400> SEQUENCE: 140

Glu Ile Val Met Thr Gln Ser Pro Ala Thr Leu Ser Val Ser Pro Gly
1               5                   10                  15

Glu Arg Ala Thr Leu Ser Cys Arg Ala Ser Leu Ser Val Ser Ser Lys
            20                  25                  30

Leu Ala Trp Tyr Gln Gln Thr Pro Gly Gln Ala Pro Arg Leu Leu Ile
        35                  40                  45

Tyr Ser Ala Ser Thr Arg Ala Thr Gly Ile Pro Val Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn His Trp Pro Pro
                85                  90                  95

Tyr Thr Phe Gly Gln Gly Thr Lys Leu Glu Ile Lys
            100                 105

<210> SEQ ID NO 141
<211> LENGTH: 357
<212> TYPE: DNA
<213> ORGANISM: Artificial Sequence
<220> FEATURE:
<223> OTHER INFORMATION: Synthetic

<400> SEQUENCE: 141
gaggtgcagc tggtggagtc tgggggaggc ttggtacagc ctgggggtc cctgagactc        60 tcctgtgcag cctctggatt caccctaac aactttgtca tgagctgggt ccgccaggct       120
ccagggaagg gctggagtg gtctcagct attagtgcta gtggtggtag tatatactac        180
gcagactccg tgaagggccg gttcaccatc tccagagaca attccaagaa cacgctgtat      240
ctgcaaatga acagcctgag agccgaggac acggccgtat attactgtgc gaaatccccg      300
tataactgga accccttga ctattgggc cagggaaccc tggtcaccgt ctcctca          357

<210> SEQ ID NO 142
<211> LENGTH: 119
<212> TYPE: PRT
<213> ORGANISM: Artificial Sequence
<220> FEATURE:
<223> OTHER INFORMATION: Synthetic

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asn Asn Phe
            20                  25                  30

Val Met Ser Trp Val Arg Gln Ala Pro Gly Lys Gly Leu Glu Trp Val
        35                  40                  45

Ser Ala Ile Ser Ala Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Tyr Asn Trp Asn Pro Phe Asp Tyr Trp Gly Gln Gly
            100                 105                 110

Thr Leu Val Thr Val Ser Ser
        115

<210> SEQ ID NO 143
<211> LENGTH: 325
<212> TYPE: DNA
<213> ORGANISM: Artificial Sequence
<220> FEATURE:
<223> OTHER INFORMATION: Synthetic

<400> SEQUENCE: 143
gaaatagtga tgacgcagtc tccagccacc ctgtctgtgt ctccagggga aagagccacc        60
ctctcctgca gggccagtct gagtgttagc agcaaattag cctggtacca gcagaaacct      120

```
ggccaggctc ccaggctcct catctatagt gcctccacca gggccactgg tatcccagcc      180
aggttcagtg gcagtgggtc tgggacagag ttcactctca ccatcagcag cctgcagtct      240
gaagattttg cagtttatta ctgtcagcag tataatcatt ggcctccgta cacttttggc      300
caggggacca agctggagat caaac                                            325
```

<210> SEQ ID NO 144
<211> LENGTH: 108
<212> TYPE: PRT
<213> ORGANISM: Artificial Sequence
<220> FEATURE:
<223> OTHER INFORMATION: Synthetic

<400> SEQUENCE: 144

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Leu Ser Val Ser Ser Lys
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn His Trp Pro Pro
                85                  90                  95

Tyr Thr Phe Gly Gln Gly Thr Lys Leu Glu Ile Lys
            100                 105
```

<210> SEQ ID NO 145
<211> LENGTH: 375
<212> TYPE: DNA
<213> ORGANISM: Artificial Sequence
<220> FEATURE:
<223> OTHER INFORMATION: Synthetic

<400> SEQUENCE: 145

```
caggtgcagc tggtggagtc tgggggaggc ttgaacagc ggggggggtc cctgagactc       60
tcctgtgcag gctctggatt cacctttaga gactatgcca tgacctgggt ccgccaggct     120
ccagggaagg gactggagtg gtctcatct attagtggtt ccgtggtaa cacatactac      180 gcagactccg tgaagggccg gttcaccatc tccagagaca attccaagaa cacgctgtat     240
ctgcaaatga acagcctgag agccgaggac acggccgtat attactgtgc gaaagatcga     300
ctctctataa caattcgccc acgctattat ggtttggacg tctggggcca agggtccacg     360
gtcaccgtct cctca                                                      375
```

<210> SEQ ID NO 146
<211> LENGTH: 125
<212> TYPE: PRT
<213> ORGANISM: Artificial Sequence
<220> FEATURE:
<223> OTHER INFORMATION: Synthetic

<400> SEQUENCE: 146

```
Gln Val Gln Leu Val Glu Ser Gly Gly Gly Leu Glu Gln Pro Gly Gly
 1               5                  10                  15

Ser Leu Arg Leu Ser Cys Ala Gly Ser Gly Phe Thr Phe Arg Asp Tyr
            20                  25                  30
```

```
Ala Met Thr Trp Val Arg Gln Ala Pro Gly Lys Gly Leu Glu Trp Val
         35                  40                  45
Ser Ser Ile Ser Gly Ser Gly Gly Asn Thr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Arg Leu Ser Ile Thr Ile Arg Pro Arg Tyr Tyr Gly Leu
             100                 105                 110
Asp Val Trp Gly Gln Gly Ser Thr Val Thr Val Ser Ser
         115                 120                 125
```

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct ttagagacta tgcc                                          24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

```
Gly Phe Thr Phe Arg Asp Tyr Ala
 1               5
```

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attagtggtt ccggtggtaa caca                                          24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

```
Ile Ser Gly Ser Gly Gly Asn Thr
 1               5
```

<210> SEQ ID NO 151
<211> LENGTH: 54
<212> TYPE: DNA
<213> ORGANISM: Artificial Sequence
<220> FEATURE:
<223> OTHER INFORMATION: Synthetic

<400> SEQUENCE: 151
gcgaaagatc gactctctat aacaattcgc ccacgctatt atggtttgga cgtc         54

<210> SEQ ID NO 152
<211> LENGTH: 18
<212> TYPE: PRT
<213> ORGANISM: Artificial Sequence
<220> FEATURE:
<223> OTHER INFORMATION: Synthetic

<400> SEQUENCE: 152

Ala Lys Asp Arg Leu Ser Ile Thr Ile Arg Pro Arg Tyr Tyr Gly Leu
 1               5                  10                  15

Asp Val

<210> SEQ ID NO 153
<211> LENGTH: 339
<212> TYPE: DNA
<213> ORGANISM: Artificial Sequence
<220> FEATURE:
<223> OTHER INFORMATION: Synthetic

<400> SEQUENCE: 153
gacatcgtgt tgacccagtc tccactctcc ctgcccgtca cccctggaga gccggcctcc      60
atctcctgca ggtctagtca gagcctcctg tatagtattg gatacaacta tttggattgg     120
tacctgcaga agtcaggggca gtctccacag ctccttatct atttgggttc taatcgggcc    180
tccggggtcc ctgacaggtt cagtggcagt ggatcaggca cagattttac actgaaaatc     240
agcagagtgg aggctgagga tgttgggttt tattactgca tgcaagctct acaaactccg     300
tacacttttg gccaggggac caagctggag atcaaacga                            339

<210> SEQ ID NO 154
<211> LENGTH: 113
<212> TYPE: PRT
<213> ORGANISM: Artificial Sequence
<220> FEATURE:
<223> OTHER INFORMATION: Synthetic

<400> SEQUENCE: 154

Asp Ile Val Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
                20                  25                  30

Ile Gly Tyr Asn Tyr Leu Asp Trp Tyr Leu Gln Lys Ser Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg

<210> SEQ ID NO 155
<211> LENGTH: 33
<212> TYPE: DNA
<213> ORGANISM: Artificial Sequence
<220> FEATURE:
<223> OTHER INFORMATION: Synthetic

<400> SEQUENCE: 155
cagagcctcc tgtatagtat tggatacaac tat         33

<210> SEQ ID NO 156
<211> LENGTH: 11
<212> TYPE: PRT
<213> ORGANISM: Artificial Sequence
<220> FEATURE:
<223> OTHER INFORMATION: Synthetic

<400> SEQUENCE: 156

Gln Ser Leu Leu Tyr Ser Ile Gly Tyr Asn Tyr
 1               5                  10

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 ttgggttct         9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Leu Gly Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
atgcaagctc tacaaactcc gtacact         27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Met Gln Ala Leu Gln Thr Pro Tyr Thr
 1               5

<210> SEQ ID NO 161
<211> LENGTH: 372
<212> TYPE: DNA
<213> ORGANISM: Artificial Sequence
<220> FEATURE:
<223> OTHER INFORMATION: Synthetic

<400> SEQUENCE: 161
gaggtgcagc tggtggagtc tgggggaggc ttggaacagc cggggggtc cctgagactc         60

```
tcctgtgcag gctctggatt cacctttaga gactatgcca tgacctgggt ccgccaggct      120
ccagggaagg gactggagtg ggtctcatct attagtggtt ccggtggtaa cacatactac      180
gcagactccg tgaagggccg gttcaccatc tccagagaca attccaagaa cacgctgtat      240
ctgcaaatga acagcctgag agccgaggac acggccgtat attactgtgc gaaagatcga      300
ctctctataa caattcgccc acgctattat ggtttggacg tctggggcca agggaccacg      360
gtcaccgtct cc                                                         372
```

<210> SEQ ID NO 162
<211> LENGTH: 124
<212> TYPE: PRT
<213> ORGANISM: Artificial Sequence
<220> FEATURE:
<223> OTHER INFORMATION: Synthetic

<400> SEQUENCE: 162

```
Glu Val Gln Leu Val Glu Ser Gly Gly Gly Leu Glu Gln Pro Gly Gly
 1               5                  10                  15

Ser Leu Arg Leu Ser Cys Ala Gly Ser Gly Phe Thr Phe Arg Asp Tyr
             20                  25                  30

Ala Met Thr Trp Val Arg Gln Ala Pro Gly Lys Gly Leu Glu Trp Val
         35                  40                  45

Ser Ser Ile Ser Gly Ser Gly Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120
```

<210> SEQ ID NO 163
<211> LENGTH: 336
<212> TYPE: DNA
<213> ORGANISM: Artificial Sequence
<220> FEATURE:
<223> OTHER INFORMATION: Synthetic

<400> SEQUENCE: 163

```
gacatcgtga tgacccagtc tccactctcc ctgcccgtca cccctggaga gccggcctcc      60
atctcctgca ggtctagtca gagcctcctg tatagtattg atacaacta tttggattgg      120 tacctgcaga agtcagggca gtctccacag ctcctgatct atttgggttc taatcgggcc      180
tccggggtcc ctgacaggtt cagtggcagt ggatcaggca cagattttac actgaaaatc      240
agcagagtgg aggctgagga tgttgggttt tattactgca tgcaagctct acaaactccg      300
tacacttttg gccaggggac caagctggag atcaaa                               336
```

<210> SEQ ID NO 164
<211> LENGTH: 112
<212> TYPE: PRT
<213> ORGANISM: Artificial Sequence
<220> FEATURE:
<223> OTHER INFORMATION: Synthetic

<400> SEQUENCE: 164

Asp Ile Val Met Thr Gln Ser Pro Leu Ser Leu Pro Val Thr Pro Gly

```
            1               5                  10                 15
         Glu Pro Ala Ser Ile Ser Cys Arg Ser Ser Gln Ser Leu Leu Tyr Ser
                         20                  25                  30

Ile Gly Tyr Asn Tyr Leu Asp Trp Tyr Leu Gln Lys Ser Gly Gln Ser
                         35                  40                  45

Pro Gln Leu Leu Ile Tyr Leu Gly Ser Asn Arg Ala Ser Gly Val Pro
                 50                  55                  60

Asp Arg Phe Ser Gly Ser Gly Ser Gly Thr Asp Phe Thr Leu Lys Ile
          65                  70                  75                  80

Ser Arg Val Glu Ala Glu Asp Val Gly Phe Tyr Tyr Cys Met Gln Ala
                         85                  90                  95

Leu Gln Thr Pro Tyr Thr Phe Gly Gln Gly Thr Lys Leu Glu Ile Lys
                    100                 105                 110
```

<210> SEQ ID NO 165
<211> LENGTH: 373
<212> TYPE: DNA
<213> ORGANISM: Artificial Sequence
<220> FEATURE:
<223> OTHER INFORMATION: Synthetic

<400> SEQUENCE: 165

```
gaggtgcagc tggtggagtc tgggggaggc ttggtacagc ctggggggtc cctgagactc     60
tcctgtgcag cctctggatt cacctttaga gactatgcca tgagctgggt ccgccaggct    120
ccagggaagg ggctggagtg ggtctcagct attagtggtt ccggtggtaa cacatactac    180
gcagactccg tgaagggccg gttcaccatc tccagagaca attccaagaa cacgctgtat    240
ctgcaaatga acagcctgag agccgaggac acggccgtat attactgtgc gaaagatcga    300
ctctctataa caattcgccc acgctattat ggtttggacg tctggggcca agggaccacg    360
gtcaccgtct cct                                                       373
```

<210> SEQ ID NO 166
<211> LENGTH: 124
<212> TYPE: PRT
<213> ORGANISM: Artificial Sequence
<220> FEATURE:
<223> OTHER INFORMATION: Synthetic

<400> SEQUENCE: 166

```
         Glu Val Gln Leu Val Glu Ser Gly Gly Gly Leu Val Gln Pro Gly Gly
          1               5                  10                  15

Ser Leu Arg Leu Ser Cys Ala Ala Ser Gly Phe Thr Phe Arg Asp Tyr
                         20                  25                  30

Ala Met Ser Trp Val Arg Gln Ala Pro Gly Lys Gly Leu Glu Trp Val
                         35                  40                  45

Ser Ala Ile Ser Gly Ser Gly Gly Asn Thr Tyr Tyr Ala Asp Ser Val
                 50                  55                  60

Lys Gly Arg Phe Thr Ile Ser Arg Asp Asn Ser Lys Asn Thr Leu Tyr
          65                  70                  75                  80

Leu Gln Met Asn Ser Leu Arg Ala Glu Asp Thr Ala Val Tyr Tyr Cys
                         85                  90                  95

Ala Lys Asp Arg Leu Ser Ile Thr Ile Arg Pro Arg Tyr Tyr Gly Leu
                    100                 105                 110

Asp Val Trp Gly Gln Gly Thr Thr Val Thr Val Ser
                    115                 120
```

<210> SEQ ID NO 167
<211> LENGTH: 337
<212> TYPE: DNA
<213> ORGANISM: Artificial Sequence
<220> FEATURE:
<223> OTHER INFORMATION: Synthetic

<400> SEQUENCE: 167

```
gatattgtga tgactcagtc tccactctcc ctgcccgtca cccctggaga gccggcctcc      60
atctcctgca ggtctagtca gagcctcctg tatagtattg atacaacta tttggattgg     120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccg    300
tacactttg gccaggggac caagctggag atcaaac                              337
```

<210> SEQ ID NO 168
<211> LENGTH: 112
<212> TYPE: PRT
<213> ORGANISM: Artificial Sequence
<220> FEATURE:
<223> OTHER INFORMATION: Synthetic

<400> SEQUENCE: 168

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu Tyr Ser
            20                  25                  30
Ile Gly Tyr Asn Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Tyr Thr Phe Gly Gln Gly Thr Lys Leu Glu Ile Lys
            100                 105                 110

<210> SEQ ID NO 169
<211> LENGTH: 375
<212> TYPE: DNA
<213> ORGANISM: Artificial Sequence
<220> FEATURE:
<223> OTHER INFORMATION: Synthetic

<400> SEQUENCE: 169

```
caggtgcagc tggtggagtc tgggggagtc ttggagcagc tgggggggtc cctgagactc      60
tcctgtacag cctctggatt cacctttaga gactatgcca tgacctgggt ccgccaggct    120
ccagggaagg ggctggagtg ggtctcatct attagtggta gtggtggtaa tacatactac    180
gcagactccg tgaggggccg gttcaccatc tccagagaca actccaacca cgctgtat      240
ctgcaaatga acagcctgag agccgaagac acggccgtat attactgtgc gaaagatcga    300
ctctccataa caattcgccc acgctattac ggtttggacg tctggggcca aggtccacg     360
gtcaccgtct cctca                                                    375
```

<210> SEQ ID NO 170
<211> LENGTH: 125

<212> TYPE: PRT
<213> ORGANISM: Artificial Sequence
<220> FEATURE:
<223> OTHER INFORMATION: Synthetic

<400> SEQUENCE: 170

Gln Val Gln Leu Val Glu Ser Gly Gly Val Leu Glu Gln Pro Gly Gly
 1               5                  10                  15

Ser Leu Arg Leu Ser Cys Thr Ala Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Arg Gly Arg Phe Thr Ile Ser Arg Asp Asn Ser Asn His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Ser Thr Val Thr Val Ser Ser
        115                 120                 125

<210> SEQ ID NO 171
<211> LENGTH: 24
<212> TYPE: DNA
<213> ORGANISM: Artificial Sequence
<220> FEATURE:
<223> OTHER INFORMATION: Synthetic

<400> SEQUENCE: 171
ggattcacct ttagagacta tgcc                                          24

<210> SEQ ID NO 172
<211> LENGTH: 8
<212> TYPE: PRT
<213> ORGANISM: Artificial Sequence
<220> FEATURE:
<223> OTHER INFORMATION: Synthetic

<400> SEQUENCE: 172

Gly Phe Thr Phe Arg Asp Tyr Ala
 1               5

<210> SEQ ID NO 173
<211> LENGTH: 24
<212> TYPE: DNA
<213> ORGANISM: Artificial Sequence
<220> FEATURE:
<223> OTHER INFORMATION: Synthetic

<400> SEQUENCE: 173
attagtggta gtggtggtaa taca                                          24

<210> SEQ ID NO 174
<211> LENGTH: 8
<212> TYPE: PRT
<213> ORGANISM: Artificial Sequence
<220> FEATURE:
<223> OTHER INFORMATION: Synthetic

<400> SEQUENCE: 174

Ile Ser Gly Ser Gly Gly Asn Thr

<210> SEQ ID NO 175
<211> LENGTH: 54
<212> TYPE: DNA
<213> ORGANISM: Artificial Sequence
<220> FEATURE:
<223> OTHER INFORMATION: Synthetic

<400> SEQUENCE: 175
gcgaaagatc gactctccat aacaattcgc ccacgctatt acggtttgga cgtc                54

<210> SEQ ID NO 176
<211> LENGTH: 18
<212> TYPE: PRT
<213> ORGANISM: Artificial Sequence
<220> FEATURE:
<223> OTHER INFORMATION: Synthetic

<400> SEQUENCE: 176

Ala Lys Asp Arg Leu Ser Ile Thr Ile Arg Pro Arg Tyr Tyr Gly Leu
 1               5                  10                  15

Asp Val

<210> SEQ ID NO 177
<211> LENGTH: 324
<212> TYPE: DNA
<213> ORGANISM: Artificial Sequence
<220> FEATURE:
<223> OTHER INFORMATION: Synthetic

<400> SEQUENCE: 177
gatattgtga tgacccagtc tccatcctcc ctgtctgcat ctgtaggaga cagagtcacc         60
attacttgcc gggcgagtca ggacattagc aattattttg cctggtatca gcagaagcca        120
gggaaagttc ctaaactcct gatctttgct gcatccactt tgcatccagg ggtcccatct        180
cggttcagtg gcagtggatc tgggacagat ttcactctca ccattagtag cctgcagcct        240
gaagatgttg caacttatta ctgtcaaaag tataacagtg ccccgtacac ttttggccag        300
gggaccaagg tggaaatcaa acga                                              324

<210> SEQ ID NO 178
<211> LENGTH: 108
<212> TYPE: PRT
<213> ORGANISM: Artificial Sequence
<220> FEATURE:
<223> OTHER INFORMATION: Synthetic

<400> SEQUENCE: 178

Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Phe Ala Trp Tyr Gln Gln Lys Pro Gly Lys Val Pro Lys Leu Leu Ile
        35                  40                  45

Phe Ala Ala Ser Thr Leu His Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Val Glu Ile Lys Arg
            100                 105

<210> SEQ ID NO 179
<211> LENGTH: 18
<212> TYPE: DNA
<213> ORGANISM: Artificial Sequence
<220> FEATURE:
<223> OTHER INFORMATION: Synthetic

<400> SEQUENCE: 179
caggacatta gcaattat                                                   18

<210> SEQ ID NO 180
<211> LENGTH: 6
<212> TYPE: PRT
<213> ORGANISM: Artificial Sequence
<220> FEATURE:
<223> OTHER INFORMATION: Synthetic

<400> SEQUENCE: 180

Gln Asp Ile Ser Asn Tyr
 1               5

<210> SEQ ID NO 181
<211> LENGTH: 9
<212> TYPE: DNA
<213> ORGANISM: Artificial Sequence
<220> FEATURE:
<223> OTHER INFORMATION: Synthetic

<400> SEQUENCE: 181 gctgcatcc                                                              9

<210> SEQ ID NO 182
<211> LENGTH: 3
<212> TYPE: PRT
<213> ORGANISM: Artificial Sequence
<220> FEATURE:
<223> OTHER INFORMATION: Synthetic

<400> SEQUENCE: 182

Ala Ala Ser
 1

<210> SEQ ID NO 183
<211> LENGTH: 27
<212> TYPE: DNA
<213> ORGANISM: Artificial Sequence
<220> FEATURE:
<223> OTHER INFORMATION: Synthetic

<400> SEQUENCE: 183
caaaagtata acagtgcccc gtacact                                         27

<210> SEQ ID NO 184
<211> LENGTH: 9
<212> TYPE: PRT
<213> ORGANISM: Artificial Sequence
<220> FEATURE:
<223> OTHER INFORMATION: Synthetic

<400> SEQUENCE: 184

Gln Lys Tyr Asn Ser Ala Pro Tyr Thr
 1               5

<210> SEQ ID NO 185
<211> LENGTH: 372
<212> TYPE: DNA
<213> ORGANISM: Artificial Sequence
<220> FEATURE:
<223> OTHER INFORMATION: Synthetic

<400> SEQUENCE: 185

```
gaggtgcagc tggtggagtc tggggggagtc ttggagcagc ctgggggtc cctgagactc      60 tcctgtacag cctctggatt caccttaga gactatgcca tgacctgggt ccgccaggct     120
ccagggaagg gctggagtg gtctcatct attagtggta gtggtggtaa tacatactac      180
gcagactccg tgagggggccg gttcaccatc tccagagaca actccaacca cacgctgtat   240
ctgcaaatga acagcctgag agccgaagac acggccgtat attactgtgc gaaagatcga   300
ctctccataa caattcgccc acgctattac ggtttggacg tctggggcca agggaccacg   360
gtcaccgtct cc                                                        372
```

<210> SEQ ID NO 186
<211> LENGTH: 124
<212> TYPE: PRT
<213> ORGANISM: Artificial Sequence
<220> FEATURE:
<223> OTHER INFORMATION: Synthetic

<400> SEQUENCE: 186

```
Glu Val Gln Leu Val Glu Ser Gly Gly Val Leu Glu Gln Pro Gly Gly
 1               5                  10                  15

Ser Leu Arg Leu Ser Cys Thr Ala Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Arg Gly Arg Phe Thr Ile Ser Arg Asp Asn Ser Asn His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120
```

<210> SEQ ID NO 187
<211> LENGTH: 321
<212> TYPE: DNA
<213> ORGANISM: Artificial Sequence
<220> FEATURE:
<223> OTHER INFORMATION: Synthetic

<400> SEQUENCE: 187

```
gacatccaga tgacccagtc tccatcctcc ctgtctgcat ctgtaggaga cagagtcacc      60
attacttgcc gggcgagtca ggacattagc aattattttg cctggtatca gcagaagcca   120
gggaaagttc ctaaactcct gatctttgct gcatccactt tgcatccagg ggtcccatct   180
cggttcagtg gcagtggatc tgggacagat ttcactctca ccattagtag cctgcagcct   240
gaagatgttg caacttatta ctgtcaaaag tataacagtg ccccgtacac ttttggccag   300
gggaccaagc tggagatcaa a                                              321
```

<210> SEQ ID NO 188
<211> LENGTH: 107
<212> TYPE: PRT
<213> ORGANISM: Artificial Sequence
<220> FEATURE:
<223> OTHER INFORMATION: Synthetic

<400> SEQUENCE: 188

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Phe Ala Trp Tyr Gln Gln Lys Pro Gly Lys Val Pro Lys Leu Leu Ile
         35                  40                  45

Phe Ala Ala Ser Thr Leu His Pro Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Tyr
                 85                  90                  95

Thr Phe Gly Gln Gly Thr Lys Leu Glu Ile Lys
            100                 105
```

<210> SEQ ID NO 189
<211> LENGTH: 373
<212> TYPE: DNA
<213> ORGANISM: Artificial Sequence
<220> FEATURE:
<223> OTHER INFORMATION: Synthetic

<400> SEQUENCE: 189

```
gaggtgcagc tggtggagtc tgggggaggc ttggtacagc ctggggggtc cctgagactc      60
tcctgtgcag cctctggatt cacctttaga gactatgcca tgagctgggt ccgccaggct     120
ccagggaagg ggctggagtg ggtctcagct attagtggta gtggtggtaa tacatactac     180
gcagactccg tgaagggccg gttcaccatc tccagagaca attccaagaa cacgctgtat     240
ctgcaaatga acagcctgag agccgaggac acggccgtat attactgtgc gaaagatcga     300
ctctccataa caattcgccc acgctattac ggtttggacg tctggggcca agggaccacg     360
gtcaccgtct cct                                                        373
```

<210> SEQ ID NO 190
<211> LENGTH: 124
<212> TYPE: PRT
<213> ORGANISM: Artificial Sequence
<220> FEATURE:
<223> OTHER INFORMATION: Synthetic

<400> SEQUENCE: 190

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Asp Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120
```

```
<210> SEQ ID NO 191
<211> LENGTH: 322
<212> TYPE: DNA
<213> ORGANISM: Artificial Sequence
<220> FEATURE:
<223> OTHER INFORMATION: Synthetic

<400> SEQUENCE: 191
gacatccaga tgacccagtc tccatcctcc ctgtctgcat ctgtaggaga cagagtcacc      60
atcacttgcc gggcgagtca ggacattagc aattatttag cctggtatca gcagaaacca     120
gggaaagttc ctaagctcct gatctatgct gcatccactt tgcaatcagg ggtcccatct     180
cggttcagtg gcagtggatc tgggacagat ttcactctca ccatcagcag cctgcagcct     240
gaagatgttg caacttatta ctgtcaaaag tataacagtg ccccgtacac ttttggccag     300
gggaccaagc tggagatcaa ac                                              322
```

```
<210> SEQ ID NO 192
<211> LENGTH: 107
<212> TYPE: PRT
<213> ORGANISM: Artificial Sequence
<220> FEATURE:
<223> OTHER INFORMATION: Synthetic

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Leu Glu Ile Lys
            100                 105
```

```
<210> SEQ ID NO 193
<211> LENGTH: 355
<212> TYPE: DNA
<213> ORGANISM: Artificial Sequence
<220> FEATURE:
<223> OTHER INFORMATION: Synthetic

<400> SEQUENCE: 193
gaagtgcacc tggtggaatc tggggaggc ttggtacagc ctggcaggtc cctgagactc       60
tcctgtgagg cctctggatt cacctttgat gattatgcca tgcactgggt ccggcaagct    120
ccggggaagg gcctggaatg ggtctcaggt cttagtcgga caagtgtcag tataggctat    180
```

```
gcggactctg tgaagggccg attcaccatc tccagagaca acgccaagaa ctccctttat    240
ttggaaatga acagtctgag acctgaggac acggccttat attactgtgc aaaatggggg    300
acccgggggt attttgacta ctggggccag ggaaccctgg tcaccgtctc ctcag         355
```

<210> SEQ ID NO 194
<211> LENGTH: 118
<212> TYPE: PRT
<213> ORGANISM: Artificial Sequence
<220> FEATURE:
<223> OTHER INFORMATION: Synthetic

<400> SEQUENCE: 194

Glu Val His Leu Val Glu Ser Gly Gly Gly Leu Val Gln Pro Gly Arg
 1               5                  10                  15

Ser Leu Arg Leu Ser Cys Glu Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Leu Ser Arg Thr Ser Val Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Pro Glu Asp Thr Ala Leu Tyr Tyr Cys
                85                  90                  95

Ala Lys Trp Gly Thr Arg Gly Tyr Phe Asp Tyr Trp Gly Gln Gly Thr
           100                 105                 110

Leu Val Thr Val Ser Ser
       115

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggattcacct ttgatgatta tgcc                                            24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Phe Thr Phe Asp Asp Tyr Ala
 1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
cttagtcgga caagtgtcag tata                                            24

<210> SEQ ID NO 198

```
<211> LENGTH: 8
<212> TYPE: PRT
<213> ORGANISM: Artificial Sequence
<220> FEATURE:
<223> OTHER INFORMATION: Synthetic

<400> SEQUENCE: 198

Leu Ser Arg Thr Ser Val Ser Ile
1               5

<210> SEQ ID NO 199
<211> LENGTH: 33
<212> TYPE: DNA
<213> ORGANISM: Artificial Sequence
<220> FEATURE:
<223> OTHER INFORMATION: Synthetic

<400> SEQUENCE: 199
gcaaaatggg ggacccgggg gtattttgac tac                                33

<210> SEQ ID NO 200
<211> LENGTH: 11
<212> TYPE: PRT
<213> ORGANISM: Artificial Sequence
<220> FEATURE:
<223> OTHER INFORMATION: Synthetic

<400> SEQUENCE: 200

Ala Lys Trp Gly Thr Arg Gly Tyr Phe Asp Tyr
1               5                   10

<210> SEQ ID NO 201
<211> LENGTH: 322
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccatcttcc gtgtctgcat ctgtgggaga cagagtcacc    60
atcacttgtc gggcgagtca ggatattagt atttggttag cctggtatca gcagagtcca   120
gggaaagccc ctaaactcct gatcaatgtt gcatcccgtt tgcaaagtgg ggtcccatca   180
aggttcagcg gcagtggatc tgggacagat ttcactctca ccatcaacag tctgcagcct   240
gaagattttg taacttacta ttgtcaacag gctaacagtt tcccgatcac cttcggccaa   300
gggacacgac tggcgaccaa ac                                           322

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ile Trp
            20                  25                  30

Leu Ala Trp Tyr Gln Gln Ser Pro Gly Lys Ala Pro Lys Leu Leu Ile
        35                  40                  45

Asn Val Ala Ser Arg Leu Gln Ser Gly Val Pro Ser Arg Phe Ser Gly
    50                  55                  60
```

Ser Gly Ser Gly Thr Asp Phe Thr Leu Thr Ile Asn Ser Leu Gln Pro
65                  70                  75                  80

Glu Asp Phe Val Thr Tyr Tyr Cys Gln Gln Ala Asn Ser Phe Pro Ile
            85                  90                  95

Thr Phe Gly Gln Gly Thr Arg Leu Ala Thr Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
caggatatta gtatttgg                                                    18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Asp Ile Ser Ile Trp
1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 gttgcatcc                                                               9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Val Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacaggcta acagtttccc gatcacc                                          27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Ala Asn Ser Phe Pro Ile Thr
 1               5

<210> SEQ ID NO 209
<211> LENGTH: 355
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc tgggggaggc ttggtacagc ctggcaggtc cctgagactc      60
tcctgtgagg cctctggatt cacctttgat gattatgcca tgcactgggt ccggcaagct     120
ccggggaagg gcctggaatg ggtctcaggt cttagtcgga caagtgtcag tataggctat     180
gcggactctg tgaagggccg attcaccatc tccagagaca acgccaagaa ctcccttat     240 ttggaaatga acagtctgag acctgaggac acggccttat attactgtgc aaaatggggg     300
acccgggggt attttgacta ctggggccag ggaaccctgg tcaccgtctc ctcag         355

<210> SEQ ID NO 210
<211> LENGTH: 118
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Gly Leu Val Gln Pro Gly Arg
 1               5                  10                  15

Ser Leu Arg Leu Ser Cys Glu Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Leu Ser Arg Thr Ser Val Ser Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Glu Met Asn Ser Leu Arg Pro Glu Asp Thr Ala Leu Tyr Tyr Cys
                 85                  90                  95

Ala Lys Trp Gly Thr Arg Gly Tyr Phe Asp Tyr Trp Gly Gln Gly Thr
            100                 105                 110

Leu Val Thr Val Ser Ser
        115

<210> SEQ ID NO 211
<211> LENGTH: 322
<212> TYPE: DNA
<213> ORGANISM: Artificial Sequence
<220> FEATURE:
<223> OTHER INFORMATION: Synthetic

<400> SEQUENCE: 211
gacatccaga tgacccagtc tccatcttcc gtgtctgcat ctgtgggaga cagagtcacc      60
atcacttgtc gggcgagtca ggatattagt atttggttag cctggtatca gcagagtcca     120
gggaaagccc ctaaactcct gatcaatgtt gcatcccgtt tgcaaagtgg ggtcccatca     180
aggttcagcg gcagtggatc tgggacagat ttcactctca ccatcaacag tctgcagcct     240

```
gaagattttg taacttacta ttgtcaacag gctaacagtt tcccgatcac cttcggccaa    300
gggacacgac tggagattaa ac                                             322
```

<210> SEQ ID NO 212
<211> LENGTH: 107
<212> TYPE: PRT
<213> ORGANISM: Artificial Sequence
<220> FEATURE:
<223> OTHER INFORMATION: Synthetic

<400> SEQUENCE: 212

```
Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Asp Ile Ser Ile Trp
             20                  25                  30

Leu Ala Trp Tyr Gln Gln Ser Pro Gly Lys Ala Pro Lys Leu Leu Ile
         35                  40                  45

Asn Val Ala Ser Arg Leu Gln Ser Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Glu Asp Phe Val Thr Tyr Tyr Cys Gln Gln Ala Asn Ser Phe Pro Ile
                 85                  90                  95

Thr Phe Gly Gln Gly Thr Arg Leu Glu Ile Lys
            100                 105
```

<210> SEQ ID NO 213
<211> LENGTH: 355
<212> TYPE: DNA
<213> ORGANISM: Artificial Sequence
<220> FEATURE:
<223> OTHER INFORMATION: Synthetic

<400> SEQUENCE: 213

```
gaagtgcagc tggtggagtc tgggggaggc ttggtacagc ctggcaggtc cctgagactc     60
tcctgtgcag cctctggatt cacctttgat gattatgcca tgcactgggt ccggcaagct    120
ccagggaagg gcctggagtg ggtctcaggt cttagtcgga caagtgtcag tataggctat    180
gcggactctg tgaagggccg attcaccatc tccagagaca cgccaagaa ctccctgtat     240 ctgcaaatga acagtctgag agctgaggac acggccttgt attactgtgc aaaatggggg    300
acccgggggt attttgacta ctggggccaa ggaaccctgg tcaccgtctc ctcag         355
```

<210> SEQ ID NO 214
<211> LENGTH: 118
<212> TYPE: PRT
<213> ORGANISM: Artificial Sequence
<220> FEATURE:
<223> OTHER INFORMATION: Synthetic

<400> SEQUENCE: 214

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Leu Ser Arg Thr Ser Val Ser Ile Gly Tyr Ala Asp Ser Val
 50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Trp Gly Thr Arg Gly Tyr Phe Asp Tyr Trp Gly Gln Gly Thr
            100                 105                 110

Leu Val Thr Val Ser Ser
        115

<210> SEQ ID NO 215
<211> LENGTH: 322
<212> TYPE: DNA
<213> ORGANISM: Artificial Sequence
<220> FEATURE:
<223> OTHER INFORMATION: Synthetic

<400> SEQUENCE: 215
gacatccaga tgacccagtc tccatcttcc gtgtctgcat ctgtaggaga cagagtcacc      60
atcacttgtc gggcgagtca ggatattagt atttggttag cctggtatca gcagaaacca     120
gggaaagccc ctaagctcct gatctatgtt gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt tcccgatcac cttcggccaa     300
gggacacgac tggagattaa ac                                              322

<210> SEQ ID NO 216
<211> LENGTH: 107
<212> TYPE: PRT
<213> ORGANISM: Artificial Sequence
<220> FEATURE:
<223> OTHER INFORMATION: Synthetic

<400> SEQUENCE: 216

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Asp Ile Ser Ile Trp
             20                  25                  30

Leu Ala Trp Tyr Gln Gln Lys Pro Gly Lys Ala Pro Lys Leu Leu Ile
         35                  40                  45

Tyr Val Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                 85                  90                  95

Thr Phe Gly Gln Gly Thr Arg Leu Glu Ile Lys
            100                 105

<210> SEQ ID NO 217
<211> LENGTH: 363
<212> TYPE: DNA
<213> ORGANISM: Artificial Sequence
<220> FEATURE:
<223> OTHER INFORMATION: Synthetic

<400> SEQUENCE: 217
gaggtgcagc tgttggagtc tgggggaggc ttgctacagc cggggggtc cctgagactc       60 tcctgtgcag cctctggaat caccttagc acctatgcca tgagctgggt ccgtcaggct      120
```

```
ccagggaggg ggctggagtg ggtctcagct attagtggta gtggtgatag cacatcctac    180
gcagactccg tgaagggccg gttcaccagc tccagagaca attccaagaa cacgctgtat    240
ctgcaaatga acagcctgag agccgaggac acggccgtat attactgtgc gaaagtcata    300
gcagctcgtc ctcactggaa cttcgatctc tggggccgtg caccctggt cactgtctcc    360 tca                                                                 363
```

<210> SEQ ID NO 218
<211> LENGTH: 121
<212> TYPE: PRT
<213> ORGANISM: Artificial Sequence
<220> FEATURE:
<223> OTHER INFORMATION: Synthetic
<400> SEQUENCE: 218

```
Glu Val Gln Leu Leu Glu Ser Gly Gly Gly Leu Leu Gln Pro Gly Gly
 1               5                  10                  15

Ser Leu Arg Leu Ser Cys Ala Ala Ser Gly Ile Thr Phe Ser Thr Tyr
            20                  25                  30

Ala Met Ser Trp Val Arg Gln Ala Pro Gly Arg Gly Leu Glu Trp Val
        35                  40                  45

Ser Ala Ile Ser Gly Ser Gly Asp Ser Thr Tyr Ala Asp Ser Val
    50                  55                  60

Lys Gly Arg Phe Thr Ser Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Val Ile Ala Ala Arg Pro His Trp Asn Phe Asp Leu Trp Gly
            100                 105                 110

Arg Gly Thr Leu Val Thr Val Ser Ser
        115                 120
```

<210> SEQ ID NO 219
<211> LENGTH: 24
<212> TYPE: DNA
<213> ORGANISM: Artificial Sequence
<220> FEATURE:
<223> OTHER INFORMATION: Synthetic
<400> SEQUENCE: 219

```
ggaatcacct ttagcaccta tgcc                                           24
```

<210> SEQ ID NO 220
<211> LENGTH: 8
<212> TYPE: PRT
<213> ORGANISM: Artificial Sequence
<220> FEATURE:
<223> OTHER INFORMATION: Synthetic
<400> SEQUENCE: 220

```
Gly Ile Thr Phe Ser Thr Tyr Ala
 1               5
```

<210> SEQ ID NO 221
<211> LENGTH: 24
<212> TYPE: DNA
<213> ORGANISM: Artificial Sequence
<220> FEATURE:
<223> OTHER INFORMATION: Synthetic
<400> SEQUENCE: 221
attagtggta gtggtgatag caca                                              24

<210> SEQ ID NO 222
<211> LENGTH: 8
<212> TYPE: PRT
<213> ORGANISM: Artificial Sequence
<220> FEATURE:
<223> OTHER INFORMATION: Synthetic

<400> SEQUENCE: 222

Ile Ser Gly Ser Gly Asp Ser Thr
1               5

<210> SEQ ID NO 223
<211> LENGTH: 42
<212> TYPE: DNA
<213> ORGANISM: Artificial Sequence
<220> FEATURE:
<223> OTHER INFORMATION: Synthetic

<400> SEQUENCE: 223
gcgaaagtca tagcagctcg tcctcactgg aacttcgatc tc                          42

<210> SEQ ID NO 224
<211> LENGTH: 14
<212> TYPE: PRT
<213> ORGANISM: Artificial Sequence
<220> FEATURE:
<223> OTHER INFORMATION: Synthetic

<400> SEQUENCE: 224

Ala Lys Val Ile Ala Ala Arg Pro His Trp Asn Phe Asp Leu
1               5                   10

<210> SEQ ID NO 225
<211> LENGTH: 324
<212> TYPE: DNA
<213> ORGANISM: Artificial Sequence
<220> FEATURE:
<223> OTHER INFORMATION: Synthetic

<400> SEQUENCE: 225
gaaattgtgt tgacacagtc tccagccacc ctgtctttgt ctccagggga aagagccacc        60
ctctcctgca gggccagtca gagtgttagt agatatttag cctggtatca acagaaacct       120
ggccaggctc ccaggctcct catctatgat gcatccaaca gggccactgg catcccagcc       180
aggttcagtg gcagtgggtc tgggacagac ttcactctca ccatcagcag cctagagcct       240
gaagattttg gagtttatta ctgtcagcag cgtagtgact ggccgctcac tttcggcgga       300
gggaccaagg tggagatcaa acgg                                              324

<210> SEQ ID NO 226
<211> LENGTH: 107
<212> TYPE: PRT
<213> ORGANISM: Artificial Sequence
<220> FEATURE:
<223> OTHER INFORMATION: Synthetic

<400> SEQUENCE: 226

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

```
Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Gly Val Tyr Tyr Cys Gln Gln Arg Ser Asp Trp Pro Leu
                 85                  90                  95

Thr Phe Gly Gly Gly Thr Lys Val Glu Ile Lys
            100                 105
```

```
<210> SEQ ID NO 227
<211> LENGTH: 18
<212> TYPE: DNA
<213> ORGANISM: Artificial Sequence
<220> FEATURE:
<223> OTHER INFORMATION: Synthetic

<400> SEQUENCE: 227
cagagtgtta gtagatat                                                 18

<210> SEQ ID NO 228
<211> LENGTH: 6
<212> TYPE: PRT
<213> ORGANISM: Artificial Sequence
<220> FEATURE:
<223> OTHER INFORMATION: Synthetic

<400> SEQUENCE: 228

Gln Ser Val Ser Arg Tyr
 1               5

<210> SEQ ID NO 229
<211> LENGTH: 9
<212> TYPE: DNA
<213> ORGANISM: Artificial Sequence
<220> FEATURE:
<223> OTHER INFORMATION: Synthetic

<400> SEQUENCE: 229 gatgcatcc                                                            9

<210> SEQ ID NO 230
<211> LENGTH: 3
<212> TYPE: PRT
<213> ORGANISM: Artificial Sequence
<220> FEATURE:
<223> OTHER INFORMATION: Synthetic

<400> SEQUENCE: 230

Asp Ala Ser
 1

<210> SEQ ID NO 231
<211> LENGTH: 27
<212> TYPE: DNA
<213> ORGANISM: Artificial Sequence
<220> FEATURE:
<223> OTHER INFORMATION: Synthetic

<400> SEQUENCE: 231
cagcagcgta gtgactggcc gctcact                                       27

<210> SEQ ID NO 232
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 232

Gln Gln Arg Ser Asp Trp Pro Leu Thr
1               5

<210> SEQ ID NO 233
<211> LENGTH: 363
<212> TYPE: DNA
<213> ORGANISM: Artificial Sequence
<220> FEATURE:
<223> OTHER INFORMATION: Synthetic

<400> SEQUENCE: 233
gaggtgcagc tgttggagtc tgggggaggc ttgctacagc cggggggtc cctgagactc     60 tcctgtgcag cctctggaat caccttagc acctatgcca tgagctgggt ccgtcaggct    120
ccagggaggg ggctggagtg ggtctcagct attagtggta gtggtgatag cacatcctac   180
gcagactccg tgaagggccg gttcaccagc tccagagaca attccaagaa cacgctgtat   240
ctgcaaatga acagcctgag agccgaggac acggccgtat attactgtgc gaaagtcata   300
gcagctcgtc ctcactggaa cttcgatctc tggggccgtg gcaccctggt cactgtctcc   360
tca                                                                 363

<210> SEQ ID NO 234
<211> LENGTH: 121
<212> TYPE: PRT
<213> ORGANISM: Artificial Sequence
<220> FEATURE:
<223> OTHER INFORMATION: Synthetic

<400> SEQUENCE: 234

Glu Val Gln Leu Leu Glu Ser Gly Gly Gly Leu Leu Gln Pro Gly Gly
1               5                   10                  15

Ser Leu Arg Leu Ser Cys Ala Ala Ser Gly Ile Thr Phe Ser Thr Tyr
            20                  25                  30

Ala Met Ser Trp Val Arg Gln Ala Pro Gly Arg Gly Leu Glu Trp Val
        35                  40                  45

Ser Ala Ile Ser Gly Ser Gly Asp Ser Thr Ser Tyr Ala Asp Ser Val
    50                  55                  60

Lys Gly Arg Phe Thr Ser Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ile Ala Ala Arg Pro His Trp Asn Phe Asp Leu Trp Gly
            100                 105                 110

Arg Gly Thr Leu Val Thr Val Ser Ser
        115                 120

<210> SEQ ID NO 235
<211> LENGTH: 324
<212> TYPE: DNA
<213> ORGANISM: Artificial Sequence
<220> FEATURE:
<223> OTHER INFORMATION: Synthetic

<400> SEQUENCE: 235
```

```
gaaattgtgt tgacacagtc tccagccacc ctgtctttgt ctccagggga aagagccacc    60
ctctcctgca gggccagtca gagtgttagt agatatttag cctggtatca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg gagtttatta ctgtcagcag cgtagtgact ggccgctcac tttcggcgga   300
gggaccaagg tggagatcaa acgg                                          324
```

<210> SEQ ID NO 236
<211> LENGTH: 107
<212> TYPE: PRT
<213> ORGANISM: Artificial Sequence
<220> FEATURE:
<223> OTHER INFORMATION: Synthetic

<400> SEQUENCE: 236

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Gly Val Tyr Tyr Cys Gln Gln Arg Ser Asp Trp Pro Leu
                85                  90                  95

Thr Phe Gly Gly Gly Thr Lys Val Glu Ile Lys
            100                 105
```

<210> SEQ ID NO 237
<211> LENGTH: 363
<212> TYPE: DNA
<213> ORGANISM: Artificial Sequence
<220> FEATURE:
<223> OTHER INFORMATION: Synthetic

<400> SEQUENCE: 237

```
gaggtgcagc tgttggagtc tgggggaggc ttggtacagc cggggggggtc cctgagactc    60 tcctgtgcag cctctggaat cacctttagc acctatgcca tgagctgggt ccgtcaggct   120
ccagggaagg ggctggagtg ggtctcagct attagtggta gtggtgatag cacatactac   180
gcagactccg tgaagggccg gttcaccatc tccagagaca attccaagaa cacgctgtat   240
ctgcaaatga acagcctgag agccgaggac acggccgtat attactgtgc gaaagtcata   300
gcagctcgtc ctcactggaa cttcgatctc tggggccgtg gcaccctggt cactgtctcc   360
tca                                                                 363
```

<210> SEQ ID NO 238
<211> LENGTH: 121
<212> TYPE: PRT
<213> ORGANISM: Artificial Sequence
<220> FEATURE:
<223> OTHER INFORMATION: Synthetic

<400> SEQUENCE: 238

```
Glu Val Gln Leu Leu Glu Ser Gly Gly Gly Leu Val Gln Pro Gly Gly
 1               5                  10                  15
```

Ser Leu Arg Leu Ser Cys Ala Ala Ser Gly Ile Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ile Ala Ala Arg Pro His Trp Asn Phe Asp Leu Trp Gly
            100                 105                 110

Arg Gly Thr Leu Val Thr Val Ser Ser
            115                 120

<210> SEQ ID NO 239
<211> LENGTH: 324
<212> TYPE: DNA
<213> ORGANISM: Artificial Sequence
<220> FEATURE:
<223> OTHER INFORMATION: Synthetic

<400> SEQUENCE: 239
gaaattgtgt tgacacagtc tccagccacc ctgtctttgt ctccagggga aagagccacc    60
ctctcctgca gggccagtca gagtgttagt agatatttag cctggtatca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagtgact ggccgctcac tttcggcgga   300
gggaccaagg tggagatcaa acgg                                          324

<210> SEQ ID NO 240
<211> LENGTH: 108
<212> TYPE: PRT
<213> ORGANISM: Artificial Sequence
<220> FEATURE:
<223> OTHER INFORMATION: Synthetic

<400> SEQUENCE: 240

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys Arg
            100                 105

<210> SEQ ID NO 241
<211> LENGTH: 366
<212> TYPE: DNA

<213> ORGANISM: Artificial Sequence
<220> FEATURE:
<223> OTHER INFORMATION: Synthetic

<400> SEQUENCE: 241

```
caggtgcagc tggtggagtc tgggggaggc gtggtccagc ctggagggtc cctgagactc    60
acctgtgcag cctctggatt caccttcagt agtaatggca tgcactgggt ccgccaggct   120
ccaggcaagg ggctggagtg ggtggcaatt atatcatatg atggaaataa tcaatactat   180
gcagactccg tgaagggccg attcaccatc tccagagaca attccaagca cacgctgtat   240
ctggaaatga acagcctgag agctgaggac acggctgtgt attactgtac aaaagccatc   300
tctataagtg gaacttacaa ctggttcgat tcctggggcc agggaaccct ggtcaccgtc   360
tcctca                                                              366
```

<210> SEQ ID NO 242
<211> LENGTH: 122
<212> TYPE: PRT
<213> ORGANISM: Artificial Sequence
<220> FEATURE:
<223> OTHER INFORMATION: Synthetic

<400> SEQUENCE: 242

```
Gln Val Gln Leu Val Glu Ser Gly Gly Gly Val Val Gln Pro Gly Arg
 1               5                  10                  15

Ser Leu Arg Leu Thr Cys Ala Ala Ser Gly Phe Thr Phe Ser Ser Asn
                20                  25                  30

Gly Met His Trp Val Arg Gln Ala Pro Gly Lys Gly Leu Glu Trp Val
            35                  40                  45

Ala Ile Ile Ser Tyr Asp Gly Asn Asn Gln Tyr Tyr Ala Asp Ser Val
        50                  55                  60

Lys Gly Arg Phe Thr Ile Ser Arg Asp Asn Ser Lys His Thr Leu Tyr
 65                  70                  75                  80

Leu Glu Met Asn Ser Leu Arg Ala Glu Asp Thr Ala Val Tyr Tyr Cys
                85                  90                  95

Thr Lys Ala Ile Ser Ile Ser Gly Thr Tyr Asn Trp Phe Asp Ser Trp
            100                 105                 110

Gly Gln Gly Thr Leu Val Thr Val Ser Ser
        115                 120
```

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243

```
ggattcacct tcagtagtaa tggc                                           24
```

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

```
Gly Phe Thr Phe Ser Ser Asn Gly
 1               5
```

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
atatcatatg atggaaataa tcaa                                              24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Tyr Asp Gly Asn Asn Gln
 1               5

<210> SEQ ID NO 247
<211> LENGTH: 45
<212> TYPE: DNA
<213> ORGANISM: Artificial Sequence
<220> FEATURE:
<223> OTHER INFORMATION: Synthetic

<400> SEQUENCE: 247
acaaaagcca tctctataag tggaacttac aactggttcg attcc                       45

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Thr Lys Ala Ile Ser Ile Ser Gly Thr Tyr Asn Trp Phe Asp Ser
 1               5                  10                  15

<210> SEQ ID NO 249
<211> LENGTH: 324
<212> TYPE: DNA
<213> ORGANISM: Artificial Sequence
<220> FEATURE:
<223> OTHER INFORMATION: Synthetic

<400> SEQUENCE: 249
gaaattgtat tgacacagtc tccagccatc ctgtctttgt ctccagggga aagagccacc       60
ctctcctgca gggccagtca gagtgttagc aggtacttag cctggtacca acagaaacct      120
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg cagttttatta ctgtcaacag cgtagcaact ggccgctcac tttcggcgga      300
gggaccaagg tggagatcaa acgg                                             324

<210> SEQ ID NO 250
<211> LENGTH: 107
<212> TYPE: PRT
<213> ORGANISM: Artificial Sequence
<220> FEATURE:
<223> OTHER INFORMATION: Synthetic

<400> SEQUENCE: 250

Glu Ile Val Leu Thr Gln Ser Pro Ala Ile Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
cagagtgtta gcaggtac                                                18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Ser Val Ser Arg Tyr
1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 gatgcatcc                                                           9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Asp Ala Ser
1

<210> SEQ ID NO 255
<211> LENGTH: 27
<212> TYPE: DNA
<213> ORGANISM: Artificial Sequence

```
<220> FEATURE:
<223> OTHER INFORMATION: Synthetic

<400> SEQUENCE: 255
caacagcgta gcaactggcc gctcact                                              27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256
```

Gln Gln Arg Ser Asn Trp Pro Leu Thr
 1               5

```
<210> SEQ ID NO 257
<211> LENGTH: 366
<212> TYPE: DNA
<213> ORGANISM: Artificial Sequence
<220> FEATURE:
<223> OTHER INFORMATION: Synthetic

<400> SEQUENCE: 257
caggtgcagc tggtggagtc tgggggaggc gtggtccagc ctggggaggtc cctgagactc          60 acctgtgcag cctctggatt caccttcagt agtaatggca tgcactgggt ccgccaggct         120
ccaggcaagg ggctggagtg ggtggcaatt atatcatatg atggaaataa tcaatactat         180
gcagactccg tgaagggccg attcaccatc tccagagaca attccaagca cacgctgtat         240
ctggaaatga acagcctgag agctgaggac acggctgtgt attactgtac aaaagccatc         300
tctataagtg gaacttacaa ctggttcgat tcctggggcc agggaaccct ggtcaccgtc         360
tcctca                                                                   366

<210> SEQ ID NO 258
<211> LENGTH: 122
<212> TYPE: PRT
<213> ORGANISM: Artificial Sequence
<220> FEATURE:
<223> OTHER INFORMATION: Synthetic

<400> SEQUENCE: 258
```

Gln Val Gln Leu Val Glu Ser Gly Gly Gly Val Val Gln Pro Gly Arg
 1               5                  10                  15

Ser Leu Arg Leu Thr Cys Ala Ala Ser Gly Phe Thr Phe Ser Ser Asn
                20                  25                  30

Gly Met His Trp Val Arg Gln Ala Pro Gly Lys Gly Leu Glu Trp Val
            35                  40                  45

Ala Ile Ile Ser Tyr Asp Gly Asn Asn Gln Tyr Tyr Ala Asp Ser Val
        50                  55                  60

Lys Gly Arg Phe Thr Ile Ser Arg Asp Asn Ser Lys His Thr Leu Tyr
 65                 70                  75                  80

Leu Glu Met Asn Ser Leu Arg Ala Glu Asp Thr Ala Val Tyr Tyr Cys
                85                  90                  95

Thr Lys Ala Ile Ser Ile Ser Gly Thr Tyr Asn Trp Phe Asp Ser Trp
            100                 105                 110

Gly Gln Gly Thr Leu Val Thr Val Ser Ser
        115                 120

<210> SEQ ID NO 259
<211> LENGTH: 324
<212> TYPE: DNA
<213> ORGANISM: Artificial Sequence
<220> FEATURE:
<223> OTHER INFORMATION: Synthetic

<400> SEQUENCE: 259

```
gaaattgtat tgacacagtc tccagccatc ctgtctttgt ctccagggga aagagccacc      60
ctctcctgca gggccagtca gagtgttagc aggtacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcaacag cgtagcaact ggccgctcac tttcggcgga     300
gggaccaagg tggagatcaa acgg                                            324
```

<210> SEQ ID NO 260
<211> LENGTH: 107
<212> TYPE: PRT
<213> ORGANISM: Artificial Sequence
<220> FEATURE:
<223> OTHER INFORMATION: Synthetic

<400> SEQUENCE: 260

```
Glu Ile Val Leu Thr Gln Ser Pro Ala Ile Leu Ser Leu Ser Pro Gly
  1               5                  10                  15
Glu Arg Ala Thr Leu Ser Cys Arg Ala Ser Gln Ser Val Ser Arg Tyr
             20                  25                  30
Leu Ala Trp Tyr Gln Gln Lys Pro Gly Gln Ala Pro Arg Leu Leu Ile
         35                  40                  45
Tyr Asp Ala Ser Asn Arg Ala Thr Gly Ile Pro Ala Arg Phe Ser Gly
     50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Leu
                 85                  90                  95
Thr Phe Gly Gly Gly Thr Lys Val Glu Ile Lys
            100                 105
```

<210> SEQ ID NO 261
<211> LENGTH: 366
<212> TYPE: DNA
<213> ORGANISM: Artificial Sequence
<220> FEATURE:
<223> OTHER INFORMATION: Synthetic

<400> SEQUENCE: 261

```
caggtgcagc tggtggagtc tgggggaggc gtggtccagc ctggagggtc cctgagactc      60
tcctgtgcag cctctggatt caccttcagt agtaatggca tgcactgggt ccgccaggct     120
ccaggcaagg ggctggagtg gtggcagtt atatcatatg atggaaataa tcaatactat     180
gcagactccg tgaagggccg attcaccatc tccagagaca attccaagaa cacgctgtat     240
ctgcaaatga acagcctgag agctgaggac acggctgtgt attactgtac aaaagccatc     300
tctataagtg gaacttacaa ctggttcgat tcctggggcc agggaaccct ggtcaccgtc     360
tcctca                                                                366
```

<210> SEQ ID NO 262
<211> LENGTH: 122

```
<212> TYPE: PRT
<213> ORGANISM: Artificial Sequence
<220> FEATURE:
<223> OTHER INFORMATION: Synthetic

<400> SEQUENCE: 262

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Asn
            20                  25                  30

Gly Met His Trp Val Arg Gln Ala Pro Gly Lys Gly Leu Glu Trp Val
        35                  40                  45

Ala Val Ile Ser Tyr Asp Gly Asn Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Lys Ala Ile Ser Ile Ser Gly Thr Tyr Asn Trp Phe Asp Ser Trp
            100                 105                 110

Gly Gln Gly Thr Leu Val Thr Val Ser Ser
        115                 120

<210> SEQ ID NO 263
<211> LENGTH: 324
<212> TYPE: DNA
<213> ORGANISM: Artificial Sequence
<220> FEATURE:
<223> OTHER INFORMATION: Synthetic

<400> SEQUENCE: 263
gaaattgtat tgacacagtc tccagccacc ctgtctttgt ctccagggga aagagccacc    60
ctctcctgca gggccagtca gagtgttagc aggtacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcaacag cgtagcaact ggccgctcac tttcggcgga   300
gggaccaagg tggagatcaa acgg                                          324

<210> SEQ ID NO 264
<211> LENGTH: 108
<212> TYPE: PRT
<213> ORGANISM: Artificial Sequence
<220> FEATURE:
<223> OTHER INFORMATION: Synthetic

<400> SEQUENCE: 264

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
```

```
                    85                  90                  95

Thr Phe Gly Gly Gly Thr Lys Val Glu Ile Lys Arg
            100                 105

<210> SEQ ID NO 265
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any amino acid

<400> SEQUENCE: 265

Xaa Xaa Xaa Xaa Xaa Xaa Xaa Xaa
 1               5

<210> SEQ ID NO 266
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any amino acid

<400> SEQUENCE: 266

Xaa Xaa Xaa Xaa Xaa Xaa Xaa Xaa
 1               5

<210> SEQ ID NO 267
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(18)
<223> OTHER INFORMATION: Xaa = Any amino acid

<400> SEQUENCE: 267

Xaa Xaa Xaa Xaa Xaa Xaa Xaa Xaa Xaa Xaa Xaa Xaa Xaa Xaa Xaa Xaa
 1               5                  10                  15

Xaa Xaa

<210> SEQ ID NO 268
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(11)
<223> OTHER INFORMATION: Xaa = Any amino acid

<400> SEQUENCE: 268

Xaa Xaa Xaa Xaa Xaa Xaa Xaa Xaa Xaa Xaa Xaa
 1               5                  10

<210> SEQ ID NO 269
<211> LENGTH: 3
<212> TYPE: PRT
```

```
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(3)
<223> OTHER INFORMATION: Xaa = Any amino acid

<400> SEQUENCE: 269

Xaa Xaa Xaa
 1

<210> SEQ ID NO 270
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(9)
<223> OTHER INFORMATION: Xaa = Any amino acid

<400> SEQUENCE: 270

Xaa Xaa Xaa Xaa Xaa Xaa Xaa Xaa Xaa
 1               5

<210> SEQ ID NO 271
<211> LENGTH: 330
<212> TYPE: PRT
<213> ORGANISM: Artificial Sequence
<220> FEATURE:
<223> OTHER INFORMATION: Synthetic

<400> SEQUENCE: 271

Ala Ser Thr Lys Gly Pro Ser Val Phe Pro Leu Ala Pro Ser Ser Lys
 1               5                   10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 272
<211> LENGTH: 327
<212> TYPE: PRT
<213> ORGANISM: Artificial Sequence
<220> FEATURE:
<223> OTHER INFORMATION: Synthetic

<400> SEQUENCE: 272

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 273
<211> LENGTH: 327
<212> TYPE: PRT
<213> ORGANISM: Artificial Sequence
<220> FEATURE:
<223> OTHER INFORMATION: Synthetic

<400> SEQUENCE: 273

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 274
<211> LENGTH: 207
<212> TYPE: PRT
<213> ORGANISM: Homo sapiens

<400> SEQUENCE: 274

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
    130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205

<210> SEQ ID NO 275
<211> LENGTH: 231
<212> TYPE: PRT
<213> ORGANISM: Macaca fasicularis

<400> SEQUENCE: 275

Met Gly Trp Leu Cys Ser Gly Leu Leu Phe Pro Val Ser Cys Leu Val
1               5                   10                  15

Leu Leu Gln Val Ala Ser Ser Gly Ser Met Lys Val Leu Gln Glu Pro
            20                  25                  30

Thr Cys Val Ser Asp Tyr Met Ser Ile Ser Thr Cys Glu Trp Lys Met
        35                  40                  45

Gly Gly Pro Thr Asn Cys Ser Ala Glu Leu Arg Leu Leu Tyr Gln Leu
    50                  55                  60
```

```
Val Phe Gln Ser Ser Glu Thr His Thr Cys Val Pro Glu Asn Asn Gly
65                  70                  75                  80

Gly Val Gly Cys Val Cys His Leu Leu Met Asp Asp Val Val Ser Met
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr His Thr Asn Val Ser Asp Thr Val Leu Leu Thr Trp Ser
    130                 135                 140

Asn Pro Tyr Pro Pro Asp Asn Tyr Leu Tyr Asn Asp Leu Thr Tyr Ala
145             150                 155                 160

Val Asn Ile Trp Ser Glu Asn Asp Pro Ala Tyr Ser Arg Ile His Asn
                165                 170                 175

Val Thr Tyr Leu Lys Pro Thr Leu Arg Ile Pro Ala Ser Thr Leu Lys
            180                 185                 190

Ser Gly Ile Ser Tyr Arg Ala Arg Val Arg Ala Trp Ala Gln His Tyr
        195                 200                 205

Asn Thr Thr Trp Ser Glu Trp Ser Pro Ser Thr Lys Trp Tyr Asn Ser
    210                 215                 220

Tyr Arg Glu Pro Phe Glu Gln
225             230
```